US012760272B2

(12) United States Patent
Liu et al.

(10) Patent No.: US 12,760,272 B2
(45) Date of Patent: Oct. 13, 2026

(54) CULTURE MEDIUM FOR ESOPHAGEAL SQUAMOUS CELL CARCINOMA EPITHELIAL CELLS, CULTURE METHOD, AND APPLICATION THEREOF

(71) Applicant: PRECEDO PHARMACEUTICALS CO., LTD, Hefei (CN)

(72) Inventors: Qingsong Liu, Hefei (CN); Jie Hu, Hefei (CN); Wenchao Wang, Hefei (CN); Cheng Chen, Hefei (CN); Tao Ren, Hefei (CN); Li Wang, Hefei (CN)

(73) Assignee: PRECEDO PHARMACEUTICALS CO., LTD, Hefei (CN)

( * ) Notice: Subject to any disclaimer, the term of this patent is extended or adjusted under 35 U.S.C. 154(b) by 949 days.

(21) Appl. No.: 17/918,971

(22) PCT Filed: Apr. 23, 2020

(86) PCT No.: PCT/CN2020/086374
§ 371 (c)(1),
(2) Date: Oct. 14, 2022

(87) PCT Pub. No.: WO2021/208130
PCT Pub. Date: Oct. 21, 2021

(65) Prior Publication Data

US 2023/0235283 A1 Jul. 27, 2023

(30) Foreign Application Priority Data

Apr. 15, 2020 (CN) ......................... 202010293661.3

(51) Int. Cl.
*C12N 5/071* (2010.01)
*C12N 5/09* (2010.01)

(52) U.S. Cl.
CPC ......... *C12N 5/0625* (2013.01); *C12N 5/0693* (2013.01); *C12N 2500/25* (2013.01); *C12N 2501/11* (2013.01); *C12N 2501/12* (2013.01); *C12N 2501/15* (2013.01); *C12N 2501/727* (2013.01); *C12N 2503/02* (2013.01)

(58) Field of Classification Search
None
See application file for complete search history.

(56) References Cited

U.S. PATENT DOCUMENTS

2014/0315911 A1 10/2014 Jin et al.

FOREIGN PATENT DOCUMENTS

| | | | |
|---|---|---|---|
| CN | 102787094 A | 11/2012 | |
| CN | 105801582 A | 7/2016 | |
| CN | 111039944 A | 4/2020 | |
| WO | 2019126696 A1 | 6/2019 | |
| WO | WO-2020073906 A1 * | 4/2020 | A61P 1/04 |
| WO | 2021/088119 A1 | 5/2021 | |
| WO | 2021/208129 A1 | 10/2021 | |

OTHER PUBLICATIONS

Triastuti et al. Pharmacological inhibition of Hippo pathway, with the novel kinase inhibitor XMU-MP-1, protects the heart against adverse effects during pressure overload. Br J Pharmacol. Oct. 8, 2019; 176(20):3956-3971. (Year: 2019).*

Watanabe et al. A ROCK inhibitor permits survival of dissociated human embryonic stem cells. Nat Biotechnol. Jun. 2007;25(6):681-6. Epub May 27, 2007. (Year: 2007).*

Watanabe et al. A ROCK inhibitor permits survival of dissociated human embryonic stem cells. Nat Biotechnol. Jun. 2007;25(6):681-6. (Year: 2007).*

Kitta et al. Hepatocyte growth factor protects cardiac myocytes against oxidative stress-induced apoptosis. Free Radic Biol Med. Oct. 1, 2001;31(7):902-10. (Year: 2001).*

Interanational Search Report dated Jan. 8, 2021 issued in PCT/CN2020/086374.

Remillard, David et al., "Dual Inhibition of Taf 1 and Bet Bromodomains From the BI-2536 Kinase Inhibitor Scaffold", ACS Medicinal Chemistry Letters (Sep. 13, 2019), vol. 10, No. 10, pp. 1443-1449.

Zhan, Meimiao et al., "Design, Synthesis, and Biological Evaluation of Novel Highly Selective Polo-like Kinase 2 Inhibitors Based on the Tetrahydropteridin Chemical Scaffold", European Journal of Medicinal Chemistry (Nov. 23, 2017), vol. 143, pp. 724-731 (Abstract only).

Chapman S. et al., "The Effect of Rho Kinase Inhibition on Long-Term Keratinocyte Proliferation is Rapid and Conditional", Stem Cell Research & Therapy 5(60):1-11 (2014).

Liu X. et al., "Conditional Reprogramming and Long-Term Expansion of Normal and Tumor Cells from Human Biospecimens", Nature Protocols 12(2):439-451 (2017).

Liu X. et al., "ROCK Inhibitor and Feeder Cells Induce the Conditional Reprogramming of Epithelial Cells", The American Journal of Pathology 180(2):599-607 (Feb. 2012).

Palechor-Ceron N. et al., "Radiation Induces Diffusible Feeder Cell Factor(s) that Cooperate with ROCK Inhibitor to Conditionally Reprogram and Immortalize Epithelial Cells", The American Journal of Pathology 183(6):1862-1870 (Dec. 2013).

(Continued)

*Primary Examiner* — Valarie E Bertoglio
*Assistant Examiner* — Briana N Ebbinghaus
(74) *Attorney, Agent, or Firm* — Scully, Scott, Murphy & Presser, P.C.

(57) ABSTRACT

Provided are a primary cell culture medium that contains a combination of an MST1/2 kinase inhibitor and a ROCK kinase inhibitor and is used for culturing primary esophageal squamous cell carcinoma epithelial cells, and a culture method using the primary cell culture medium. In the culture method, the primary cell culture medium is used to culture primary cells on a culture vessel coated with an extracellular matrix glue, so that the primary cells prolilferate rapidly. A cell model obtained by using the primary cell culture medium and the primary cell culture method of the present invention can be used for the efficacy evaluation and screening of drugs.

13 Claims, 15 Drawing Sheets
(2 of 15 Drawing Sheet(s) Filed in Color)

(56) References Cited

OTHER PUBLICATIONS

Purdie K.J. et al., "Isolation and Culture of Squamous Cell Carcinoma Lines", Cancer Cell Culture: Methods and Protocols, Second Edition, Methods in Molecular Biology 731:151-159 (2011).
Sachs N. et al., "A Living Biobank of Breast Cancer Organoids Captures Disease Heterogeneity", Cell 172:373-386 (Jan. 11, 2018).
Extended European Search Report dated Aug. 13, 2024 received in European Application No. 20 930 874.1.

* cited by examiner

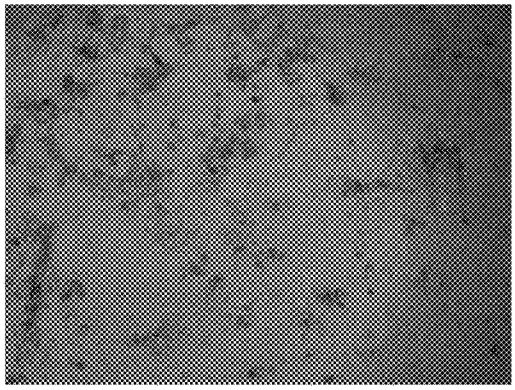
FIG. 4A
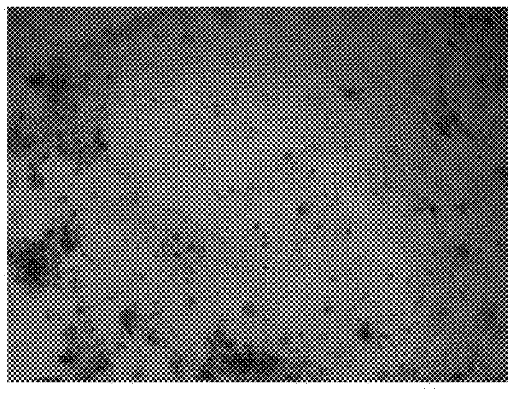
FIG. 4B
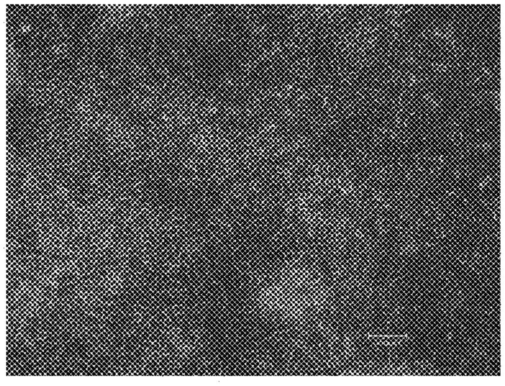
FIG. 5A
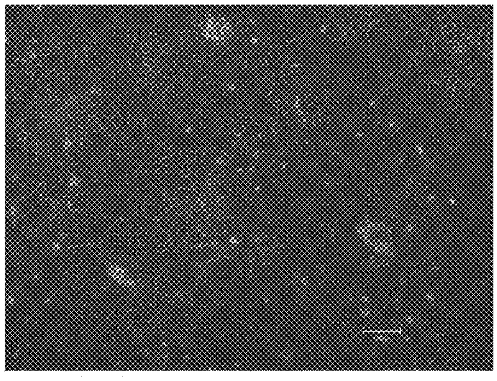
FIG. 5B
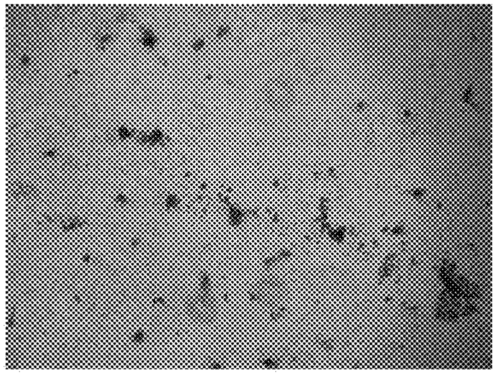
FIG. 6A (BM)
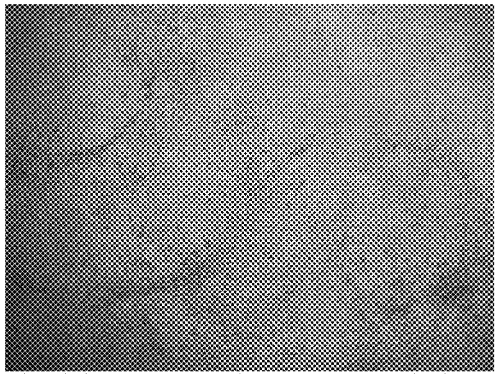
FIG. 6B (FEM)

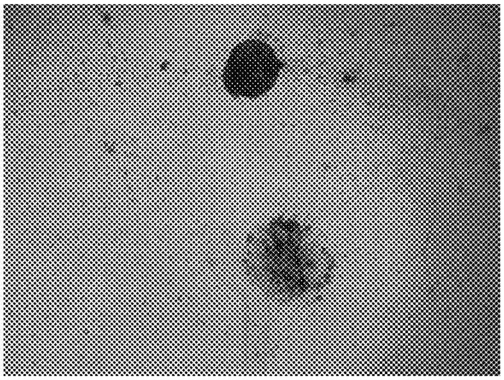
FIG. 6C (KM)
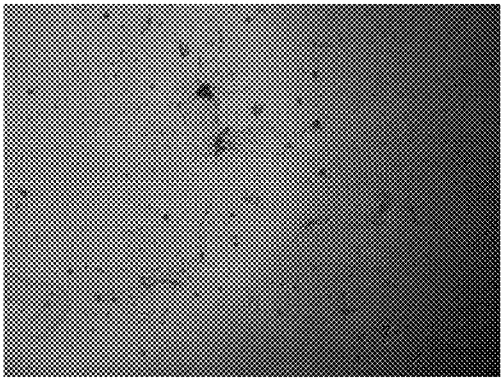
FIG. 6D (EPI)
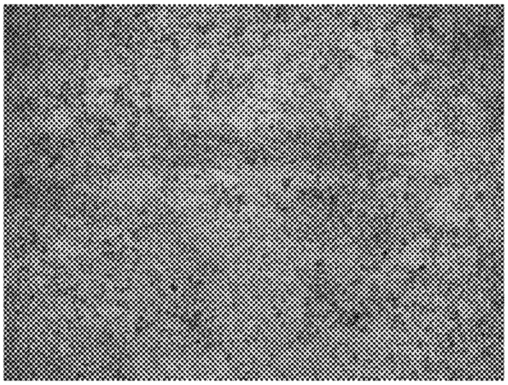
FIG. 6E (FM)
| Different mediums | Sample No. 0F0056 | Sample No. 0F0060 | Sample No. 0F0061 | Sample No. 0F0062 | Sample No. 0F0071 | Sample No. 0F0075 |
|---|---|---|---|---|---|---|
| Basic medium BM | × | × | × | √ | √ | √ |
| Medium of invention FEM | √ | √√ | √√ | √√ | √√ | √√ |
| Literature Medium KM | √ | × | × | × | × | √ |
| Commercial medium EPI | √ | × | × | √√ | √ | √ |
| Conditional reprogramming medium FM | NT | √√ | √√ | √√ | √√ | √ |
FIG. 7

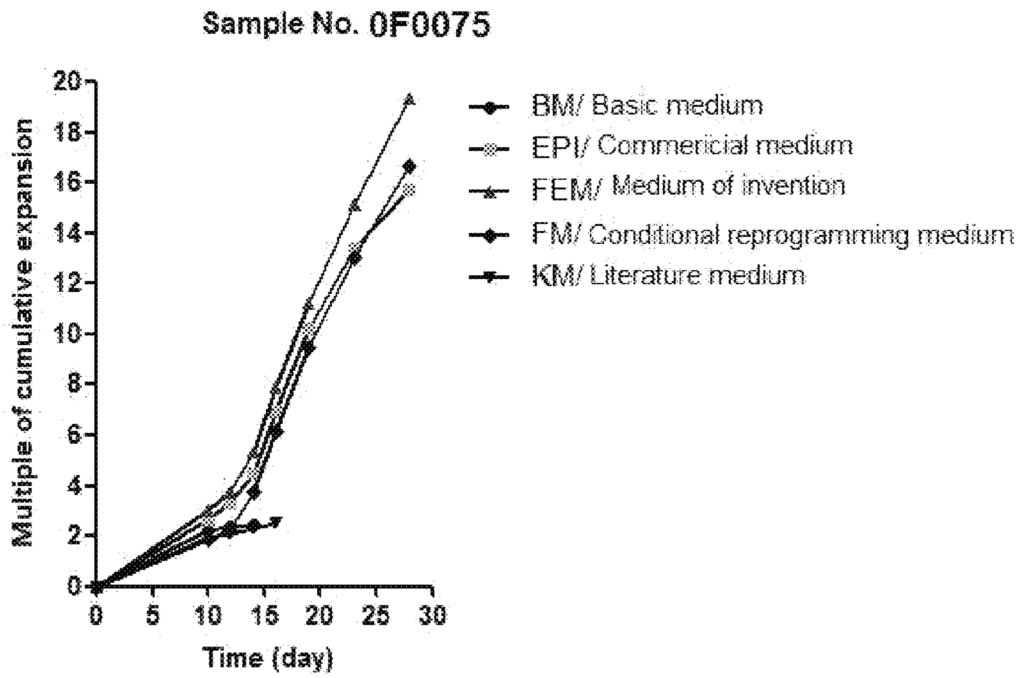
FIG. 8
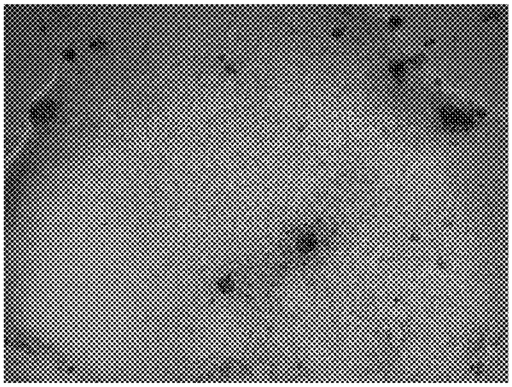
FIG. 9A (0F0075-P1 FEM)
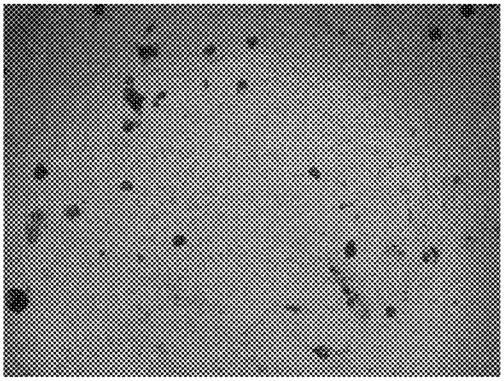
FIG. 9B (0F0075-P9 FEM)
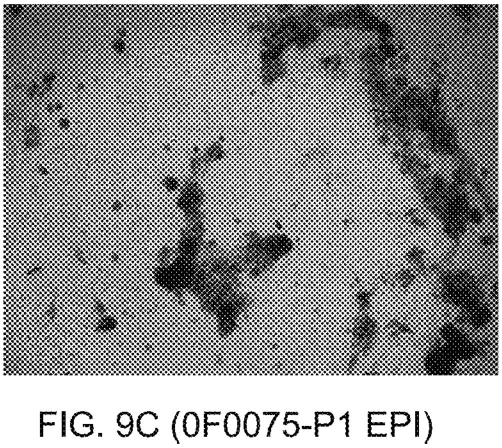
FIG. 9C (0F0075-P1 EPI)
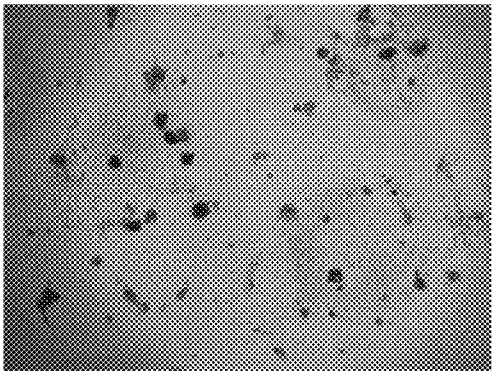
FIG. 9D (0F0075-P9 EPI)

Pathological result of Sample No. 0F0053 tissue

Diagnosis opinion:

(Esophageal) squamous cell carcinoma
Results of immunohistochemical marker: cancer cell CK(+), P63(+), P53(+, >95%), Ki-67(+, 70%)
This case was diagnosed by expert group

FIG. 10A

Pathological result of Sample No. 0F0053 cells expended to the 6th passage by using the culture medium of invention

Diagnosis opinion:

(Esophageal) squamous cell carcinoma was found
Results of immunohistochemical marker: epithelial cells CK(+), P63(+), P53(+, weak), Ki-67(+, 60%)
This case was diagnosed by expert group

FIG. 10B

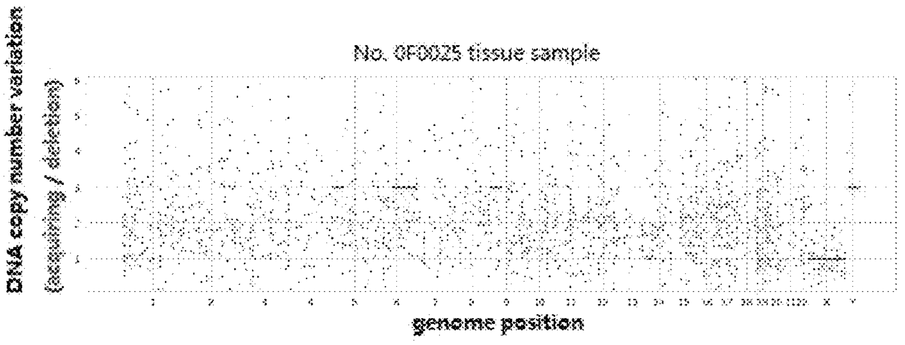

FIG. 11A

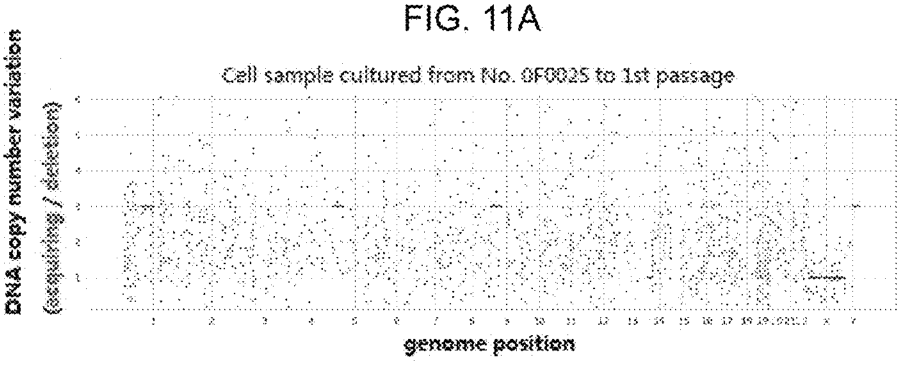

FIG. 11B

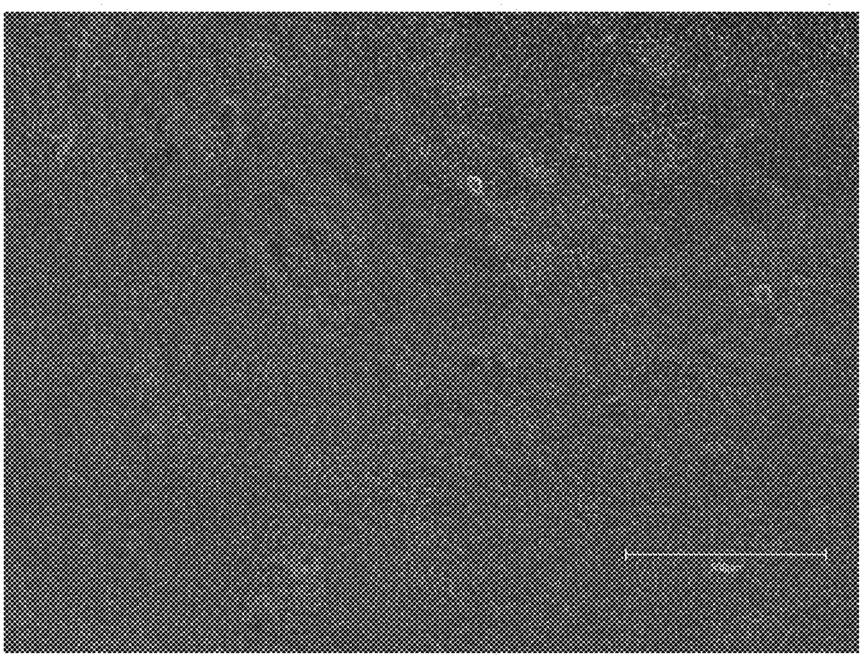
FIG. 13A (Microscopic photo of cells cultured with medium of invention FEM)
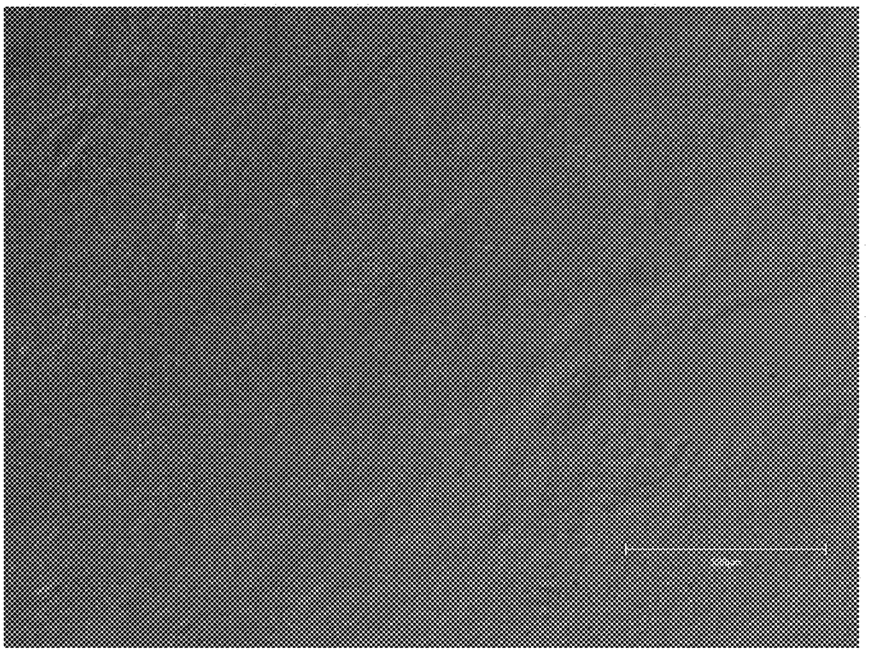
FIG. 13B (Microscopic photo of cells cultured with FEM without Compound 1)

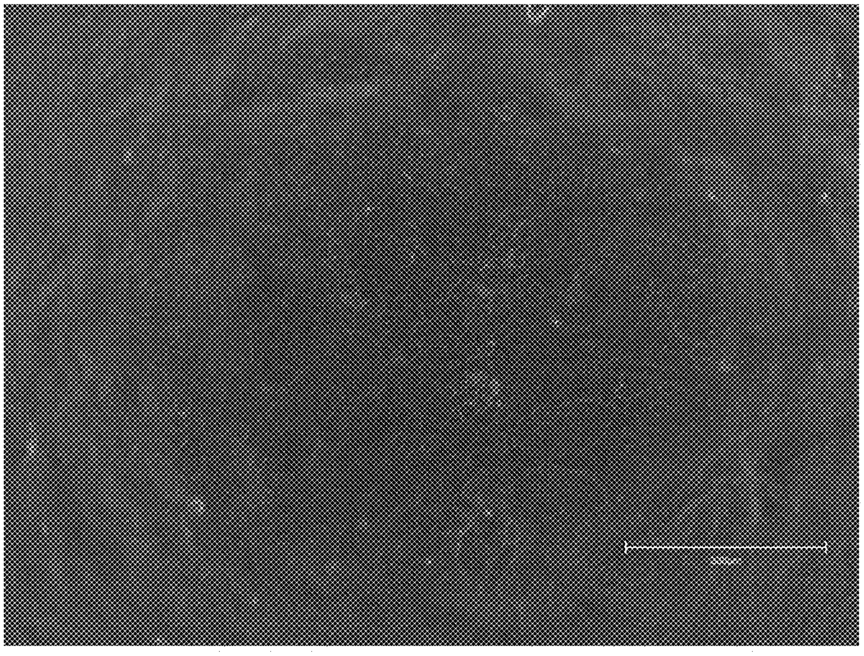
FIG. 13C (Microscopic photo of cells cultured with FEM without A83-01)
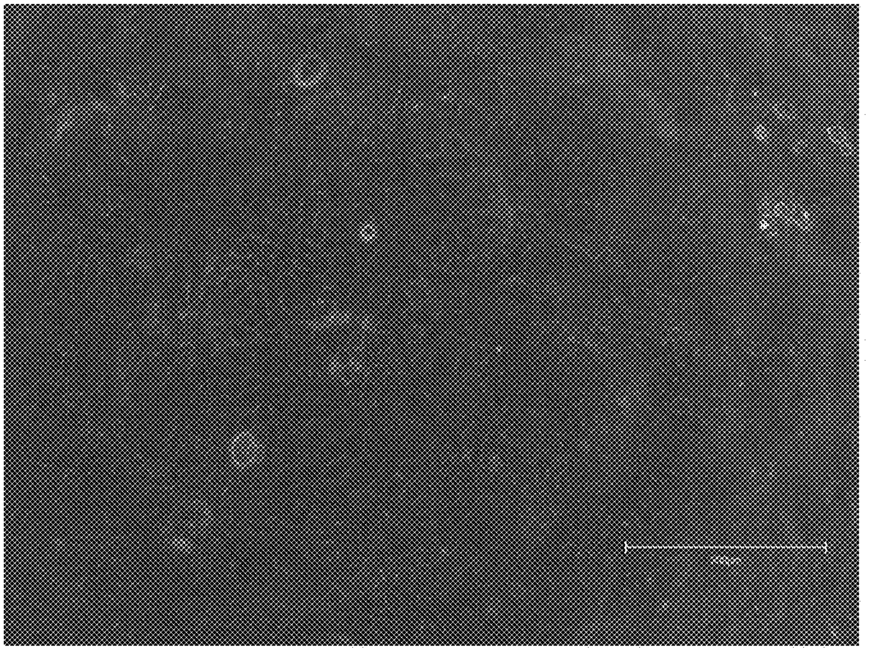
FIG. 13D (Microscopic photo of cells cultured with FEM without Y27632)

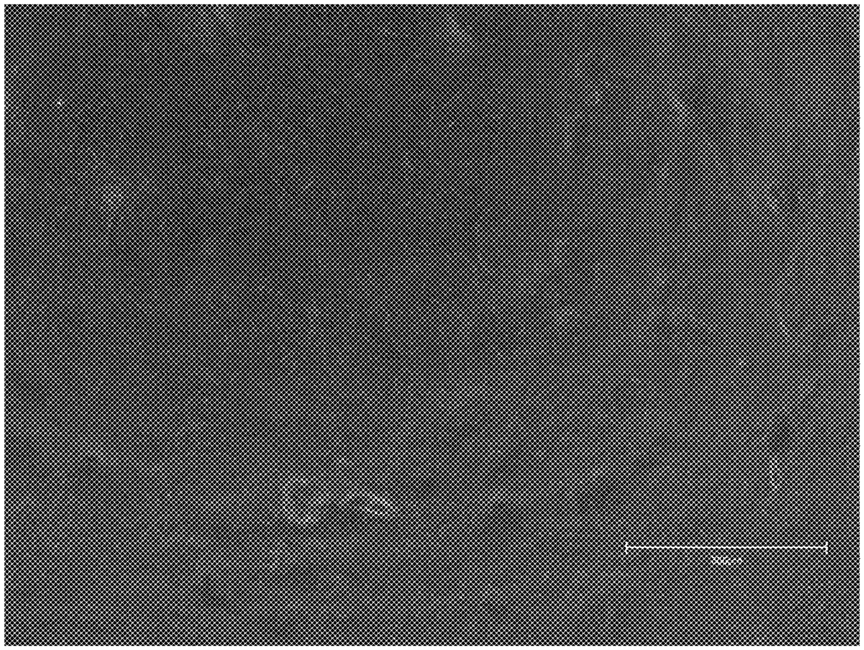
FIG. 13E (Microscopic photo of cells cultured with FEM without SB202190)
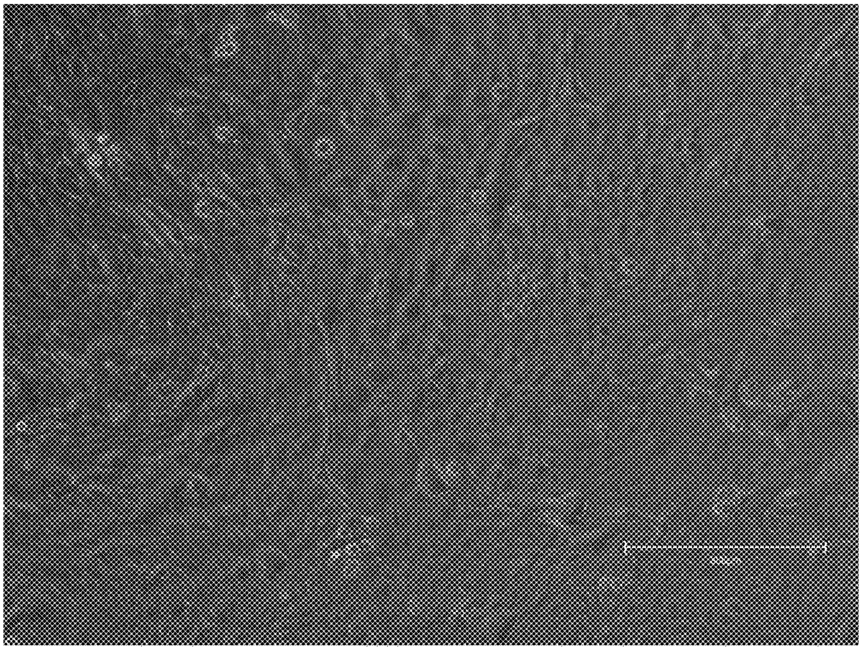
FIG. 13F (Microscopic photo of cells cultured with FEM without A83-01 and SB202190)

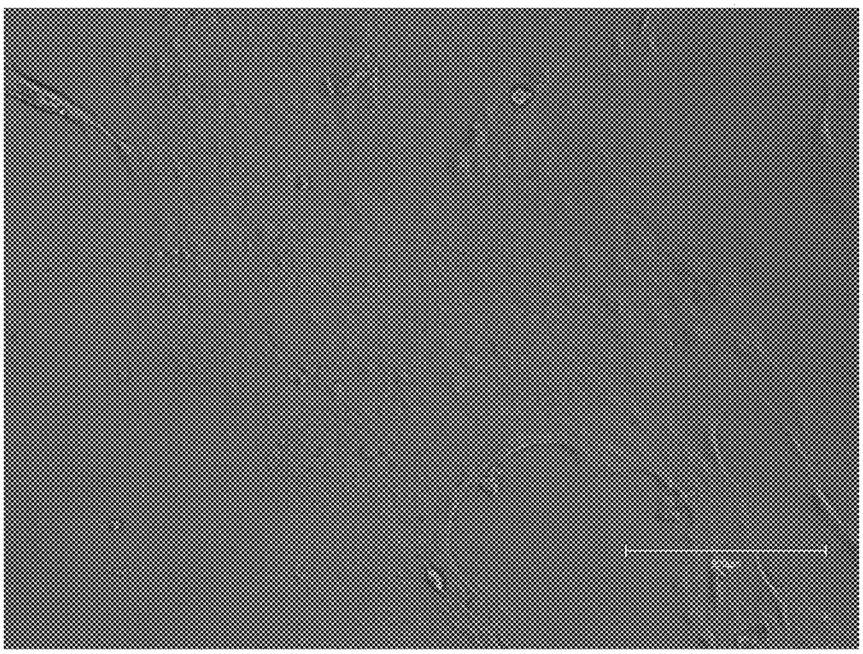
FIG. 13G (Microscopic photo of cells cultured with FEM without Compound 1 and Y27632)
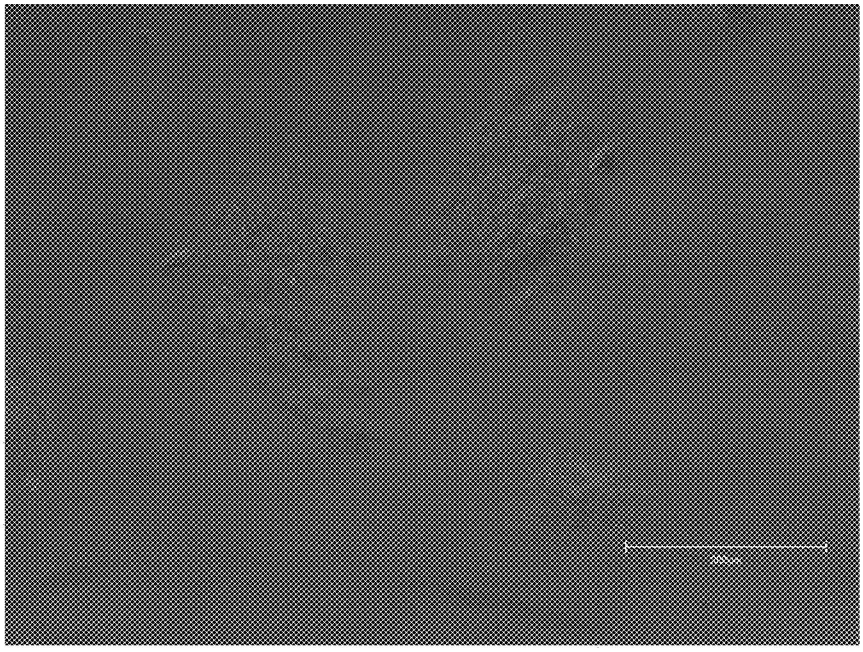
FIG. 13H (Microscopic photo of cells cultured with basic medium BM)

CULTURE MEDIUM FOR ESOPHAGEAL SQUAMOUS CELL CARCINOMA EPITHELIAL CELLS, CULTURE METHOD, AND APPLICATION THEREOF

TECHNICAL FIELD

The invention relates to the field of medical technology, in particular to a culture medium and a culture method for culturing or expanding primary epithelial cells of esophageal squamous cell carcinoma in vitro, and also to a method and use of the cultured cells in the efficacy evaluation and screening of drugs.

BACKGROUND OF THE INVENTION

Esophageal cancer is one of the most common gastrointestinal malignancies in the world. According to the latest statistics from the National Cancer Center, among the top ten incidences of malignant tumors, esophageal cancer ranks sixth in men and ranks second in women. In many regions of the world, the local incidence rate has increased, while China is a high incidence region of esophageal cancer, with an annual incidence of 246,000 and an average annual death toll of about 150,000, accounting for 21.8% of the national cancer mortality, ranking the fourth among the cancers that cause the most deaths (data from the National Cancer Center, 2019). In recent years, although people have made some progress in the research of molecular typing and pathogenesis of esophageal cancer, due to the differences in molecular typing of esophageal cancer between China and foreign countries, the therapeutic tools for esophageal squamous cell carcinoma (ESCC), especially for patients at advanced stage, are still limited, and personalized guidance on precise medication is not available. In contrast with adenocarcinoma, ESCC does not have a relatively clear molecular target, and thus, it is difficult to actually predict the efficacy of clinical drugs only based on molecular or genetic diagnosis.

Functional testing refers to the method of detecting the sensitivity of antitumor drugs on cancer patient cells in vitro. The key to apply this method is to develop tumor cell models that have short growth cycle and can represent the biological characteristics of ESCC patients. In addition, the cell model should be easy to operate to quickly and efficiently predict the efficacy of clinical medication, so as to give precise medication guidance to cancer patients in a timely manner. However, the normally low success rates of in vitro establishment of cell models from the primary tumor cells of cancer patients, the long growth cycles, and the problems such as excessive proliferation of mesenchymal cells (such as fibroblasts, and the like), all restrict the development in this field. There are currently two technologies for culturing primary epithelial/stem cells that are relatively mature in the field of functional testing of tumor cells. One is the technology that uses irradiated feeder cells and ROCK kinase inhibitor Y27632 to promote the growth of primary epithelial cells to investigate the drug sensitivity of individual patients, that is, cell conditional reprogramming technology (Liu et al., Am J Pathol, 180: 599-607, 2012). Another technique is 3D culture of adult stem cells in vitro to obtain organoids similar to tissues and organs (Hans Clevers et al., Cell, 11; 172(1-2): 373-386, 2018).

However, both techniques have certain limitations. Cell reprogramming is a technique in which a patient's autologous primary epithelial cells are co-cultured with murine-derived feeder cells. The presence of these murine-derived cells may interfere with the drug sensitivity test results of the patient's autologous primary cells during drug sensitivity testing on the patient's primary cells; on the other hand, if murine-derived feeder cells are knocked out, the patient's autologous primary cells may be removed from the reprogramming environment, and the cell proliferation rate and the intracellular signaling pathway may be significantly changed (Liu et al., Am J Pathol, 183(6): 1862-1870, 2013; Liu et al., Cell Death Dis., 9(7): 750, 2018), which leads to a result that the response of the patient's autologous primary cells to the drug is greatly affected. The organoid technology is a technology that embeds the patient's autologous primary epithelial cells into the extracellular matrix for 3D in vitro culture, which does not require feeder cells, and thus, there is no interference problem of murine-derived feeder cells. However, the culture medium of the organoid technology needs to be added with a variety of specific growth factors (such as Wnt proteins and R-spondin family proteins), which is expensive and unsuitable for extensive use in clinical. In addition, the organoid needs to be embedded in the extracellular matrix gel during the entire culture process, and the plating steps of cell inoculation, passage, and drug sensitivity test are cumbersome and time-consuming as compared to 2D culture operations. Additionally, the size of the organoid formed by this technology is difficult to control, and some organoids may grow too large and cause an internal necrosis. Therefore, the organoid technology has poorer operability and applicability than the 2D culture technology. It requires professional technicians to operate, and thus, is not suitable for extensive and wide use in clinical for in vitro drug sensitivity testing (Nick Barker, Nat Cell Biol, 18(3): 246-54, 2016).

In view of the limitations of the above technologies, it is necessary to develop a culture technology for primary ESCC epithelial cells in clinic, which may provide short culture period, controllable cost, and convenient operation, without interference from exogenous cells. When the technology is applied to construct a primary ESCC tumor cell model, the cultured ESCC tumor cells can represent the biological characteristics of the ESCC patients. By evaluating in vitro the sensitivity of anti-tumor drugs in the cell models derived from individual cancer patients, the response rate of the anti-tumor drug can be improved in clinic, and the pains caused by inappropriate drugs to the patients and the wastes of medical resources can be reduced.

SUMMARY OF THE INVENTION

In view of the deficiencies of the prior art, the invention intends to provide a culture medium for culturing primary ESCC epithelial cells and a method for culturing primary ESCC epithelial cells using the culture medium. The primary ESCC epithelial cell culture medium and the culture method of the invention can achieve the goal of short in vitro culture period, controllable cost, convenient operation and no interference from exogenous cells. When the technology is applied to construct a primary ESCC tumor cell model, the primary ESCC tumor cells with the biological characteristics of the ESCC patients can be obtained, which can be applied in new drug screening and in vitro drug sensitivity test.

One aspect of the invention is to provide a primary cell culture medium for culturing primary ESCC epithelial cells, comprising an MST1/2 kinase inhibitor and a ROCK kinase inhibitor, wherein the MST1/2 kinase inhibitor comprises a compound of Formula (I) or a pharmaceutically acceptable salt, or a solvate thereof, and the ROCK kinase inhibitor is at least one selected from the group consisting of Y27632, Fasudil, and H-1152.

Formula (I)

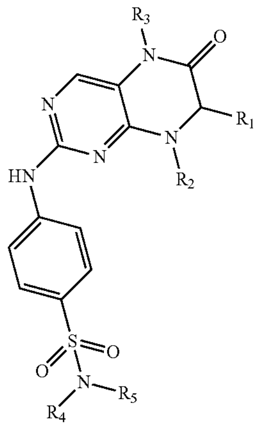

Wherein, $R_1$ is selected from C1-C6 alkyl, C3-C6 cycloalkyl, C4-C8 cycloalkylalkyl, C2-C6 spirocycloalkyl, and aryl (e.g., phenyl and naphthyl, etc.) optionally independently substituted with 1-2 $R_6$, aryl C1-C6 alkyl (e.g., phenylmethyl, etc.) optionally independently substituted with 1-2 $R_6$ and heteroaryl (e.g., thienyl, etc.) optionally independently substituted with 1-2 $R_6$;

$R_2$ and $R_3$ are each independently selected from C1-C6 alkyl, preferably C1-C3 alkyl, more preferably methyl;

$R_4$ and $R_5$ are each independently selected from hydrogen, C1-C6 alkyl, C3-C6 cycloalkyl, C4-C8 cycloalkylalkyl, hydroxyl C1-C6 alkyl, C1-C6 haloalkyl, C1-C6 alkylamino C1-C6 alkyl, C1-C6 alkoxy C1-C6 alkyl, and C3-C6 heterocyclyl C1-C6 alkyl (the heterocyclyl is selected from e.g., piperidyl, tetrahydropyranyl, etc.);

$R_6$ is selected from halogen (preferably fluoro and chloro, more preferably fluoro), C1-C6 alkyl (preferably methyl), C1-C6 alkoxy (preferably methoxy), and C1-C6 haloalkyl (preferably trifluoromethyl).

In a preferable embodiment, the MST1/2 kinase inhibitor comprises a compound of Formula (Ia) or a pharmaceutically acceptable salt, or a solvate thereof, Formula (Ia)

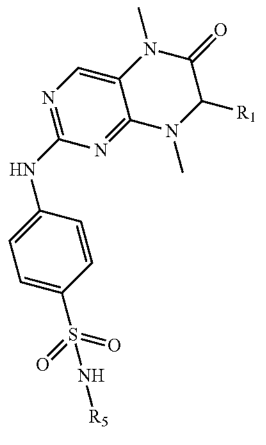

Wherein, $R_1$ is selected from C1-C6 alkyl, phenyl optionally independently substituted with 1-2 $R_6$, thienyl optionally independently substituted with 1-2 $R_6$, and phenylmethyl optionally independently substituted with 1-2 $R_6$; more preferably, $R_1$ is phenyl optionally independently substituted with 1-2 $R_6$;

$R_5$ is selected from hydrogen, C1-C6 alkyl, and C3-C6 cycloalkyl; more preferably, $R_5$ is hydrogen;

$R_6$ is independently selected from halogen, C1-C6 alkyl, and C1-C6 haloalkyl; more preferably, $R_6$ is fluoro, methyl or trifluoromethyl.

Preferably, the MST1/2 kinase inhibitor is at least one selected from the following compounds or a pharmaceutically acceptable salt, or a solvate thereof.

1

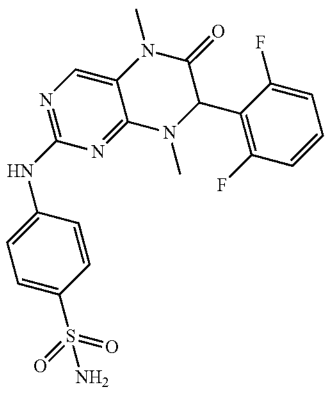

2

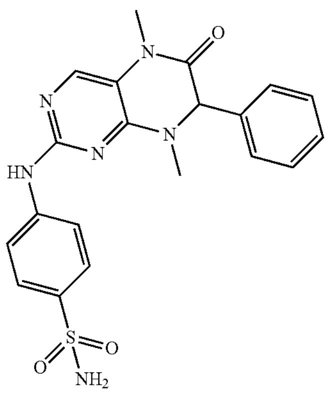

3

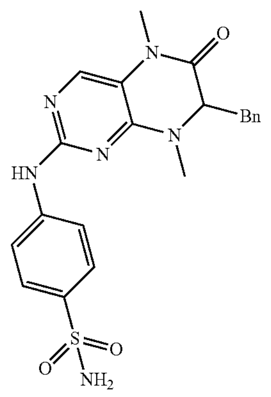 [SMILES: CN1C(=O)C(Cc2ccccc2)N(C)c2nc(Nc3ccc(S(N)(=O)=O)cc3)ncc21]

-continued
4
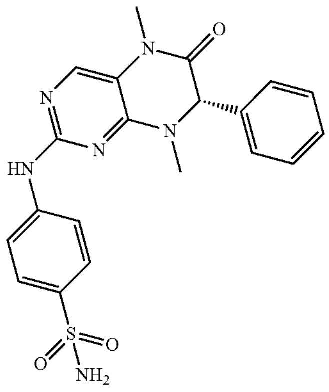 [SMILES: CN1C(=O)[C@H](c2ccccc2)N(C)c2nc(Nc3ccc(S(N)(=O)=O)cc3)ncc21]
5
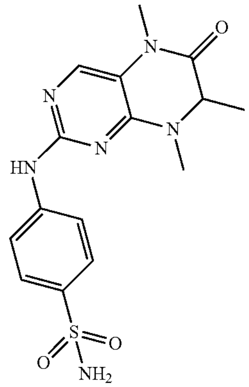 [SMILES: CC1C(=O)N(C)c2cnc(Nc3ccc(S(N)(=O)=O)cc3)nc2N1C]
6
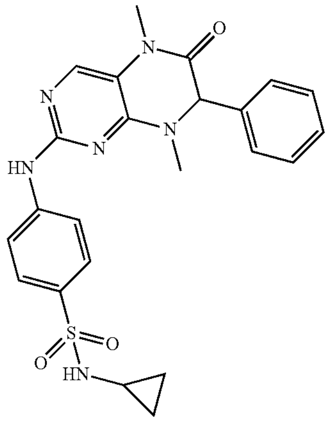 [SMILES: CN1C(=O)C(c2ccccc2)N(C)c2nc(Nc3ccc(S(=O)(=O)NC4CC4)cc3)ncc21]
7
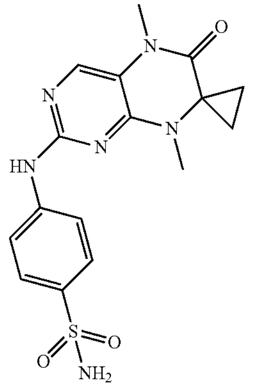 [SMILES: CN1C(=O)C2(CC2)N(C)c2nc(Nc3ccc(S(N)(=O)=O)cc3)ncc21]
-continued
8
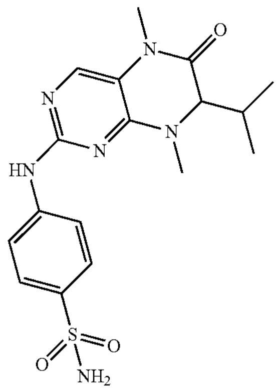 [SMILES: CC(C)C1C(=O)N(C)c2cnc(Nc3ccc(S(N)(=O)=O)cc3)nc2N1C]
9
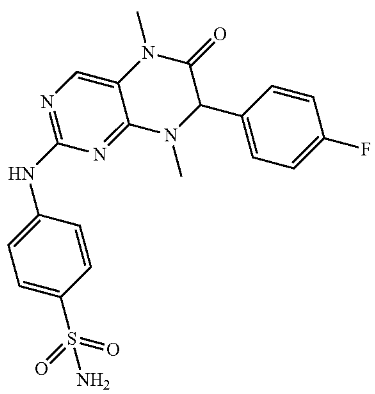 [SMILES: CN1C(=O)C(c2ccc(F)cc2)N(C)c2nc(Nc3ccc(S(N)(=O)=O)cc3)ncc21]
10
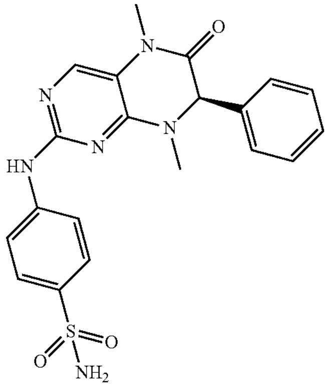
11
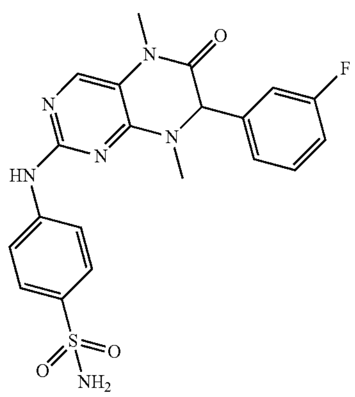 [SMILES: CN1C(=O)C(c2cccc(F)c2)N(C)c2nc(Nc3ccc(S(N)(=O)=O)cc3)ncc21]

-continued
12
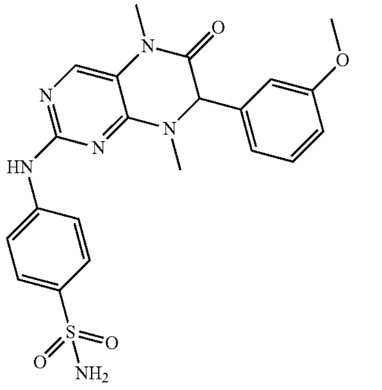 [SMILES: COc1cccc(C2C(=O)N(C)c3cnc(Nc4ccc(S(N)(=O)=O)cc4)nc3N2C)c1]
13
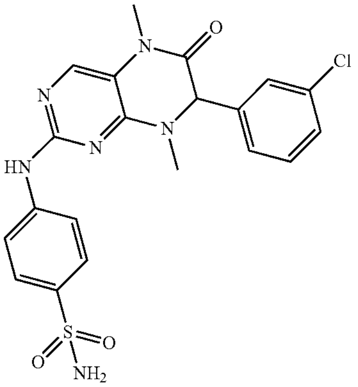 [SMILES: CN1C(=O)C(c2cccc(Cl)c2)N(C)c2nc(Nc3ccc(S(N)(=O)=O)cc3)ncc21]
14
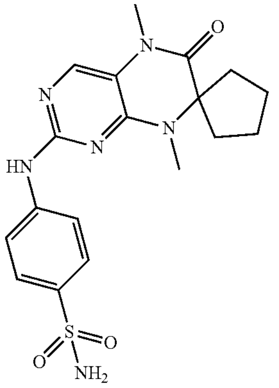 [SMILES: CN1C(=O)C2(CCCC2)N(C)c2nc(Nc3ccc(S(N)(=O)=O)cc3)ncc21]
15
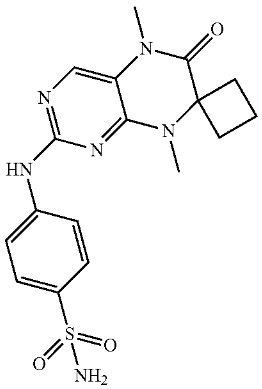 [SMILES: CN1C(=O)C2(CCC2)N(C)c2nc(Nc3ccc(S(N)(=O)=O)cc3)ncc21]
-continued
16
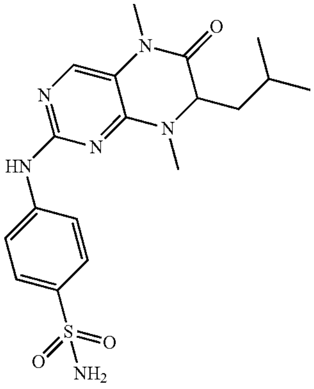 [SMILES: CC(C)CC1C(=O)N(C)c2cnc(Nc3ccc(S(N)(=O)=O)cc3)nc2N1C]
17
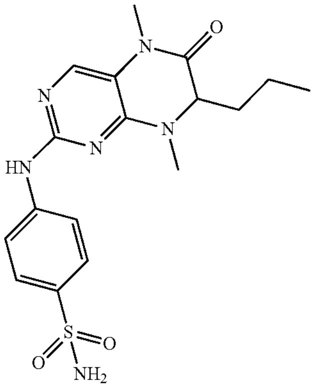
18
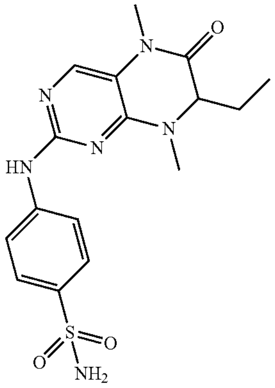 [SMILES: CCC1C(=O)N(C)c2cnc(Nc3ccc(S(N)(=O)=O)cc3)nc2N1C]
19
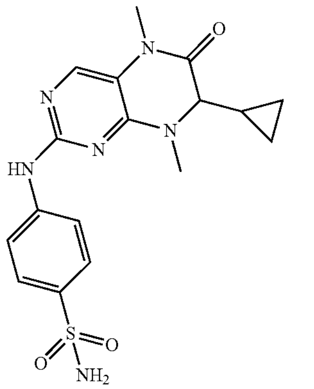 [SMILES: CN1C(=O)C(C2CC2)N(C)c2nc(Nc3ccc(S(N)(=O)=O)cc3)ncc21]

-continued
20
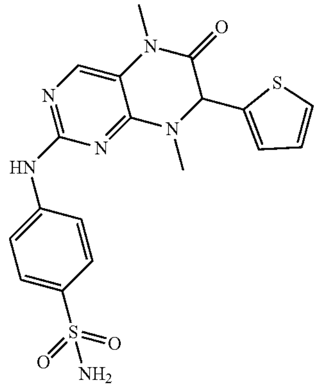 [SMILES: CN1C(=O)C(c2cccs2)N(C)c2nc(Nc3ccc(S(N)(=O)=O)cc3)ncc21]
21
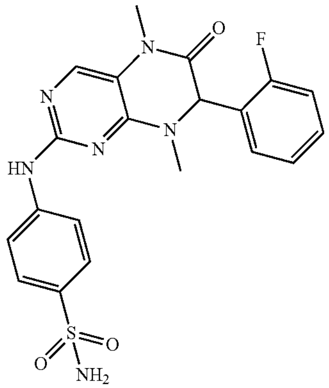
22
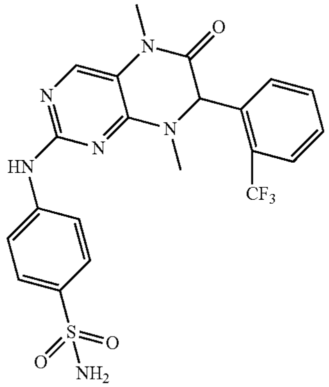 [SMILES: CN1C(=O)C(c2ccccc2C(F)(F)F)N(C)c2nc(Nc3ccc(S(N)(=O)=O)cc3)ncc21]
23
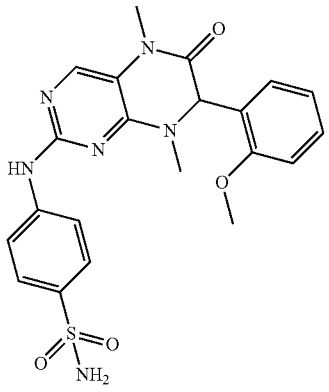 [SMILES: COc1ccccc1C1C(=O)N(C)c2cnc(Nc3ccc(S(N)(=O)=O)cc3)nc2N1C]
-continued
24
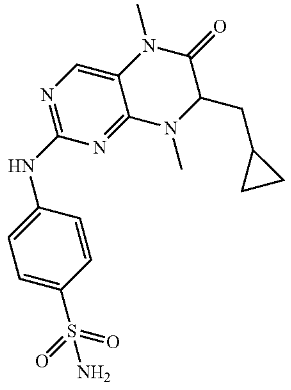 [SMILES: CN1C(=O)C(CC2CC2)N(C)c2nc(Nc3ccc(S(N)(=O)=O)cc3)ncc21]
25
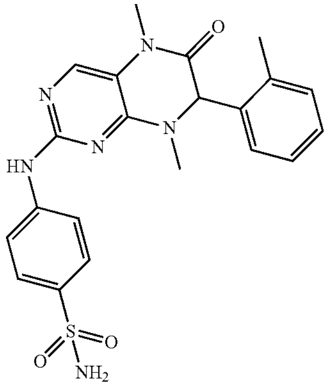 [SMILES: Cc1ccccc1C1C(=O)N(C)c2cnc(Nc3ccc(S(N)(=O)=O)cc3)nc2N1C]
26
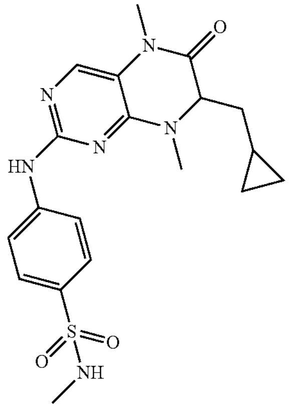 [SMILES: CNS(=O)(=O)c1ccc(Nc2ncc3c(n2)N(C)C(CC2CC2)C(=O)N3C)cc1]
27
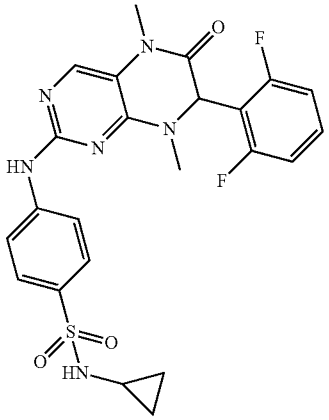 [SMILES: CN1C(=O)C(c2c(F)cccc2F)N(C)c2nc(Nc3ccc(S(=O)(=O)NC4CC4)cc3)ncc21]

-continued
28
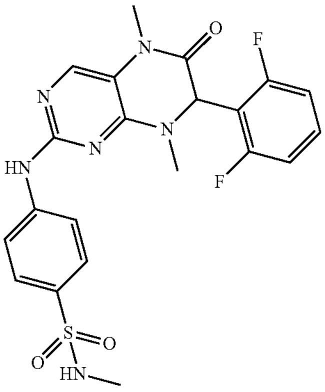 [SMILES: CNS(=O)(=O)c1ccc(Nc2ncc3c(n2)N(C)C(c2c(F)cccc2F)C(=O)N3C)cc1]
29
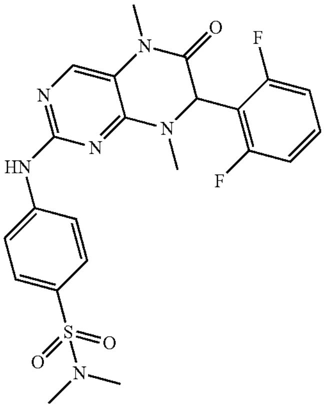 [SMILES: CN1C(=O)C(c2c(F)cccc2F)N(C)c2nc(Nc3ccc(S(=O)(=O)N(C)C)cc3)ncc21]
30
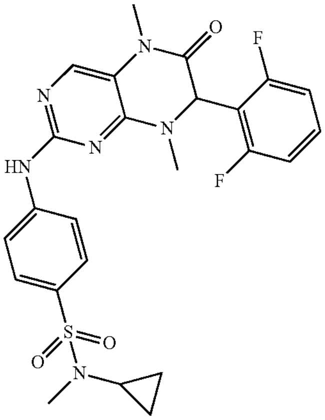 [SMILES: CN1C(=O)C(c2c(F)cccc2F)N(C)c2nc(Nc3ccc(S(=O)(=O)N(C)C4CC4)cc3)ncc21]
31
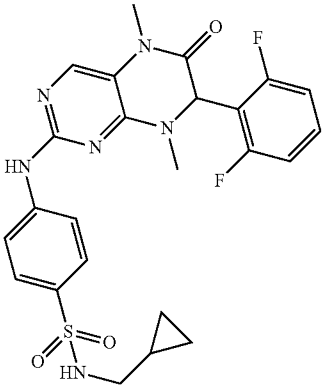 [SMILES: CN1C(=O)C(c2c(F)cccc2F)N(C)c2nc(Nc3ccc(S(=O)(=O)NCC4CC4)cc3)ncc21]
-continued
32
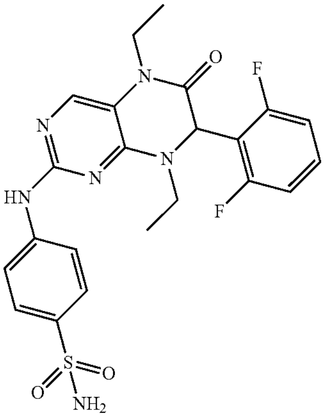 [SMILES: CCN1C(=O)C(c2c(F)cccc2F)N(CC)c2nc(Nc3ccc(S(N)(=O)=O)cc3)ncc21]
33
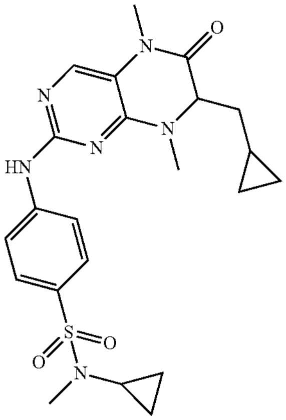 [SMILES: CN1C(=O)C(CC2CC2)N(C)c2nc(Nc3ccc(S(=O)(=O)N(C)C4CC4)cc3)ncc21]
34
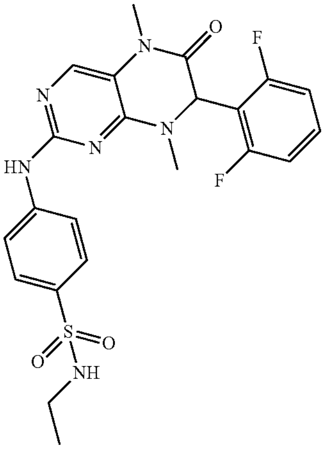 [SMILES: CCNS(=O)(=O)c1ccc(Nc2ncc3c(n2)N(C)C(c2c(F)cccc2F)C(=O)N3C)cc1]

-continued
35
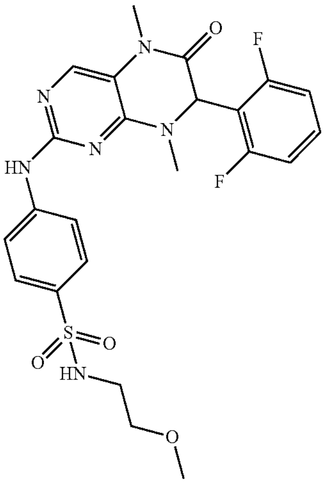 [SMILES: COCCNS(=O)(=O)c1ccc(Nc2ncc3c(n2)N(C)C(c2c(F)cccc2F)C(=O)N3C)cc1]
36
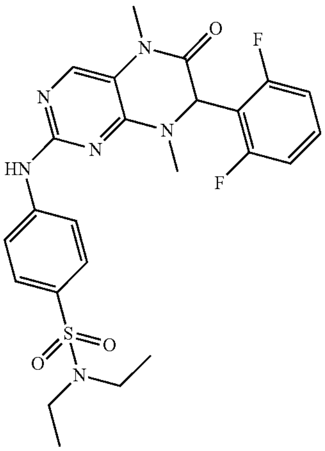 [SMILES: CCN(CC)S(=O)(=O)c1ccc(Nc2ncc3c(n2)N(C)C(c2c(F)cccc2F)C(=O)N3C)cc1]
37
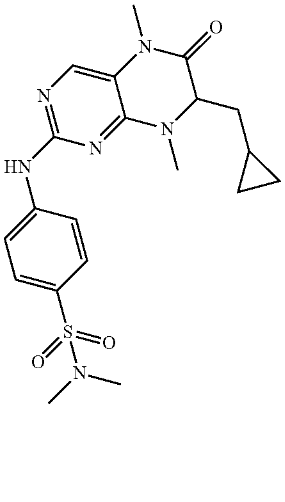 [SMILES: CN1C(=O)C(CC2CC2)N(C)c2nc(Nc3ccc(S(=O)(=O)N(C)C)cc3)ncc21]
-continued
38
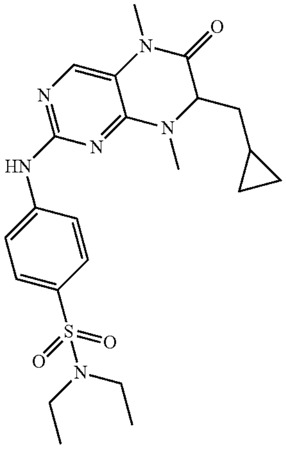 [SMILES: CCN(CC)S(=O)(=O)c1ccc(Nc2ncc3c(n2)N(C)C(CC2CC2)C(=O)N3C)cc1]
39
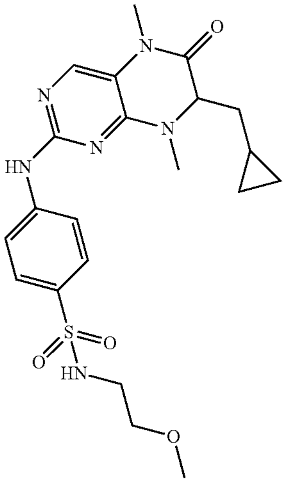 [SMILES: COCCNS(=O)(=O)c1ccc(Nc2ncc3c(n2)N(C)C(CC2CC2)C(=O)N3C)cc1]
40
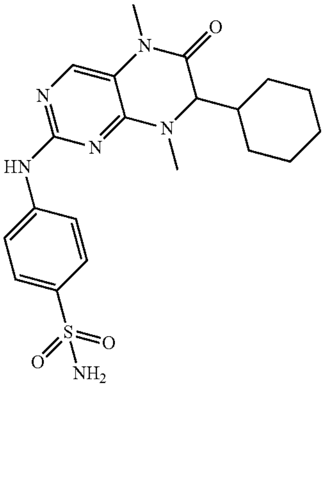 [SMILES: CN1C(=O)C(C2CCCCC2)N(C)c2nc(Nc3ccc(S(N)(=O)=O)cc3)ncc21]

-continued
41
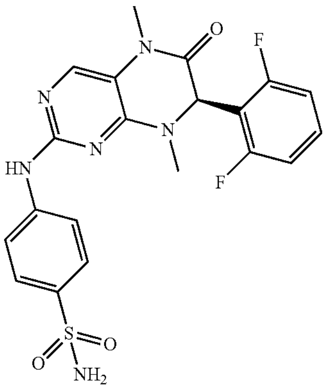 [SMILES: CN1C(=O)[C@@H](c2c(F)cccc2F)N(C)c2nc(Nc3ccc(S(N)(=O)=O)cc3)ncc21]
42
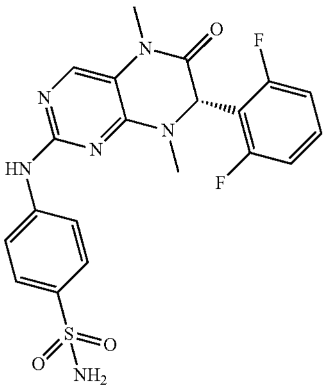 [SMILES: CN1C(=O)[C@H](c2c(F)cccc2F)N(C)c2nc(Nc3ccc(S(N)(=O)=O)cc3)ncc21]
43
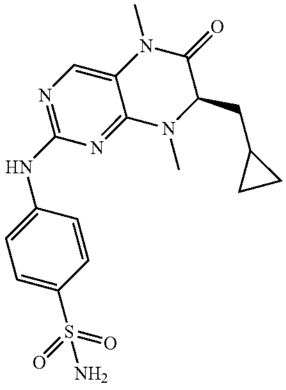 [SMILES: CN1C(=O)[C@@H](CC2CC2)N(C)c2nc(Nc3ccc(S(N)(=O)=O)cc3)ncc21]
44
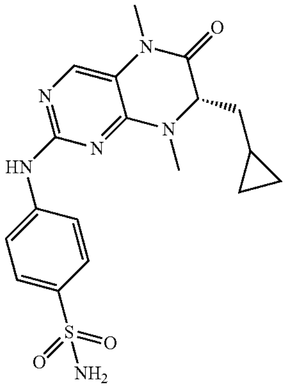 [SMILES: CN1C(=O)[C@H](CC2CC2)N(C)c2nc(Nc3ccc(S(N)(=O)=O)cc3)ncc21]
-continued
45
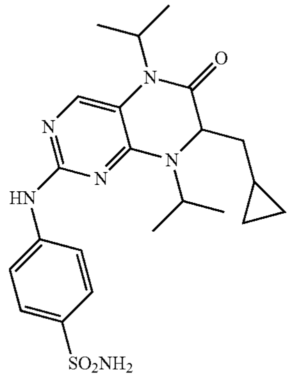 [SMILES: CC(C)N1C(=O)C(CC2CC2)N(C(C)C)c2nc(Nc3ccc(S(N)(=O)=O)cc3)ncc21]
46
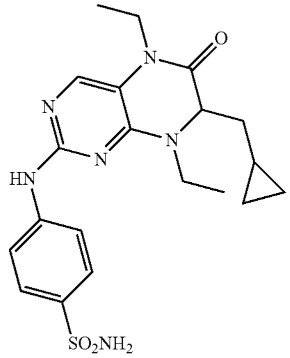 [SMILES: CCN1C(=O)C(CC2CC2)N(CC)c2nc(Nc3ccc(S(N)(=O)=O)cc3)ncc21]
47
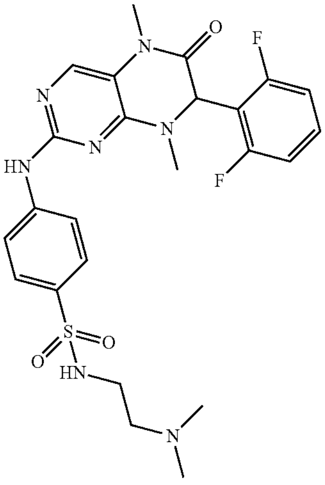 [SMILES: CN(C)CCNS(=O)(=O)c1ccc(Nc2ncc3c(n2)N(C)C(c2c(F)cccc2F)C(=O)N3C)cc1]

-continued
48
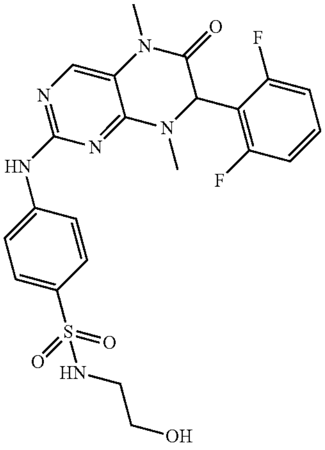 [SMILES: CN1C(=O)C(c2c(F)cccc2F)N(C)c2nc(Nc3ccc(S(=O)(=O)NCCO)cc3)ncc21]
49
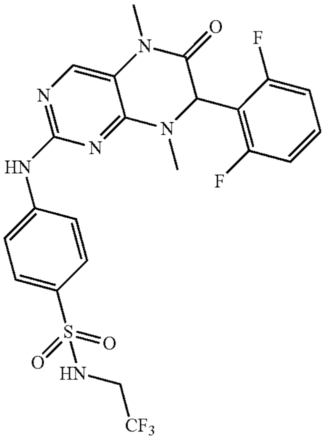 [SMILES: CN1C(=O)C(c2c(F)cccc2F)N(C)c2nc(Nc3ccc(S(=O)(=O)NCC(F)(F)F)cc3)ncc21]
50
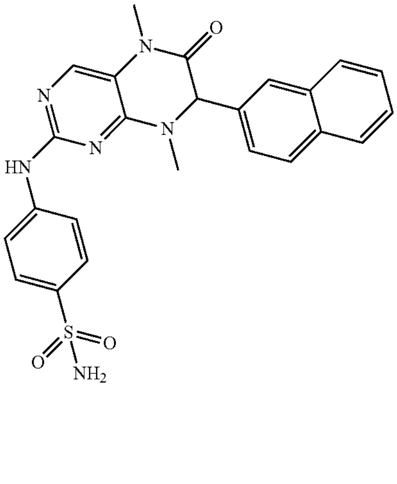 [SMILES: CN1C(=O)C(c2ccc3ccccc3c2)N(C)c2nc(Nc3ccc(S(N)(=O)=O)cc3)ncc21]
-continued
51
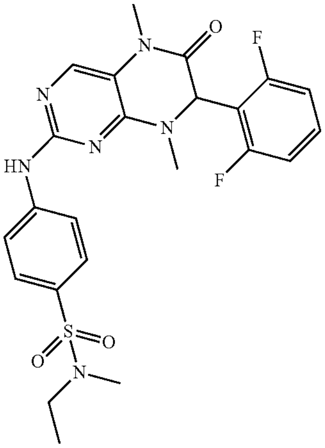 [SMILES: CCN(C)S(=O)(=O)c1ccc(Nc2ncc3c(n2)N(C)C(c2c(F)cccc2F)C(=O)N3C)cc1]
52
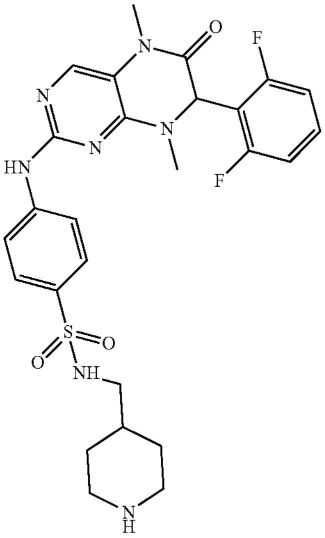
53
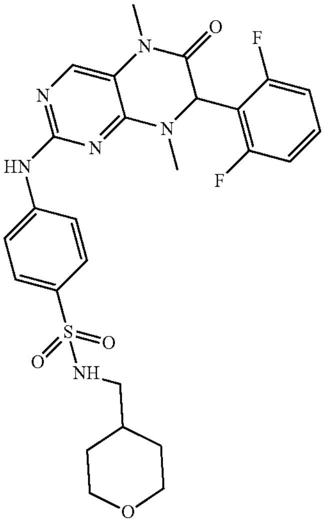

-continued

54

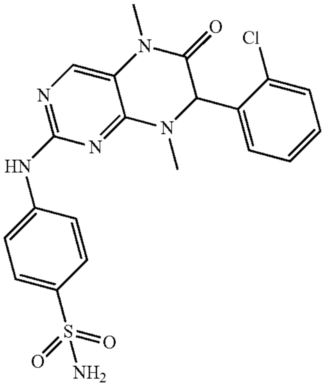

55

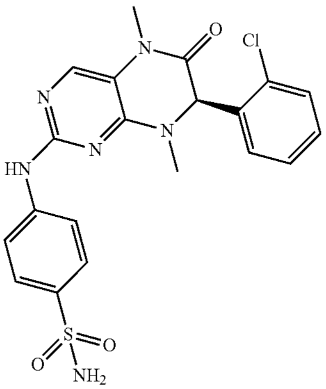

56

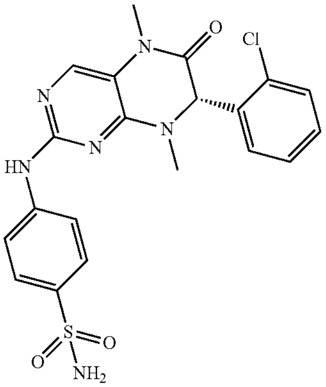

57

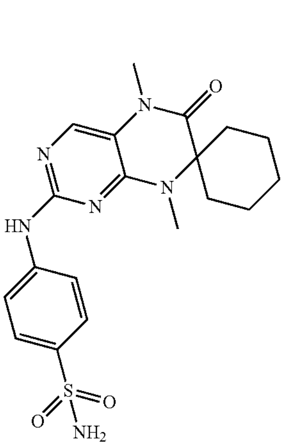

-continued

58

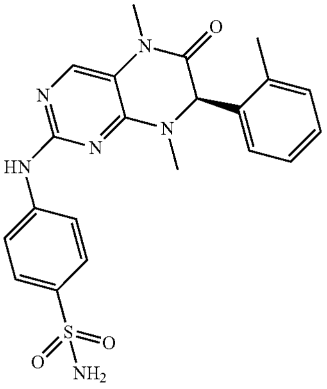

59

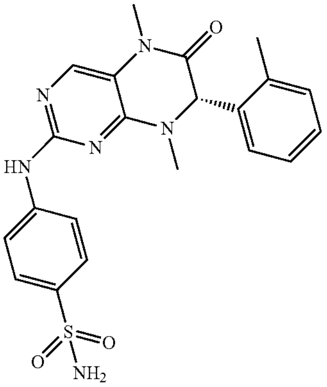

Most preferably, the MST1/2 kinase inhibitor of the invention is Compound 1, and the ROCK kinase inhibitor of the invention is preferably Y27632.

In the embodiment of the invention, the amount of MST1/2 kinase inhibitor in the culture medium is usually 0.3 μM-10 μM, preferably 0.75 μM-6 μM, more preferably 2 μM-6 μM. In addition, the amount of ROCK kinase inhibitor in the culture medium is usually 0.3 μM-20 μM, preferably 2.5 μM-15 μM, more preferably 7.5 μM-12.5 μM.

Preferably, the primary cell culture medium of the invention further contains one or more of the following factors: epidermal growth factor (EGF); insulin-transferrin-selenium complex; B27 additive or N2 additive; hepatocyte growth factor (HGF); a TGFβ type I receptor inhibitor selected from at least one of A83-01, SB431542, Repsox, SB505124, SB525334, SD208, LY36494, and SJN2511; and a P38/MAPK inhibitor selected from at least one of SB202190, SB203580, VX-702, VX-745, PD169316, RO4402247, and BIRB796.

In a preferred embodiment, the amount of EGF is 12.5 ng/ml-100 ng/ml, more preferably 50 ng/ml-100 ng/ml, the respective amounts of insulin/transferrin/sodium selenite in the insulin-transferrin-selenium complex are 2.5-20 μg/ml, 1.25-10 μg/ml, 1.25-10 ng/ml, respectively, and more preferably 5-20 μg/ml, 2.5-10 μg/ml, 2.5-10 ng/ml, respectively; the volume concentration of the B27 additive or N2 additive in the culture medium is 1:25-1:200, more preferably 1:25-1:50; the amount of HGF is 2.5 ng/ml-20 ng/ml, more preferably 10 ng/ml-20 ng/ml; the TGFβ type I receptor inhibitor is preferably A83-01 and the amount of the TGFβ type I receptor inhibitor is 125 nM-500 nM, preferably 250 nM-500 nM; the P38/MAPK inhibitor is preferably SB202190, and the amount of the P38/MAPK inhibitor is 125 nM-500 nM, preferably 250 nM-500 nM.

Compared to the cell conditional reprogramming medium and the ESCC epithelial cell organoid medium, the composition of this medium is supplemented with a combination of an MST1/2 kinase inhibitor and a ROCK kinase inhibitor (particularly preferred are Compound 1 and Y27632), but does not contain uncertain components such as serum, bovine pituitary extract or the like, niche factors that are necessary for organoid culture such as Wnt agonists, R-spondin family proteins, BMP inhibitors or the like, nor does it contain nicotinamide, and N-acetylcysteine, thereby greatly reducing the cost of the medium, simplifying the operation process of preparing the medium, and realizing the in vitro culture of the primary ESCC epithelial cells with controllable cost and convenient operation.

In the invention, the primary ESCC epithelial cells can be selected from ESCC tumor cells, normal ESCC epithelial cells, and ESCC epithelial stem cells.

One aspect of the invention is to provide a method for culturing the primary ESCC epithelial cells, comprising the following steps:

(1) Preparing the primary cell culture medium of the invention according to the above composition.

(2) Coating a culture vessel with extracellular matrix gel diluent.

Specifically, as the extracellular matrix gel, a low growth factor type extracellular matrix gel can be used, for example, the commercial Matrigel (purchased from Corning) or BME (purchased from Trevigen) can be used. More specifically, the extracellular matrix gel is diluted with a serum-free medium, which may be DMEM/F12 (purchased from Corning). The dilution ratio of the extracellular matrix gel is 1:50-1:400, preferably 1:100-1:200. The coating method comprises adding the diluted extracellular matrix gel into the culture vessel to cover the bottom of the culture vessel completely, and standing for 30 minutes or more, preferably standing and coating at 37° C. for 30-60 minutes. After the coating is completed, the excess extracellular matrix gel diluent is discarded, and the culture vessel is ready for later use.

(3) Isolating the primary ESCC epithelial cells from the ESCC tissue.

The primary ESCC epithelial cells can be derived, for example, from the ESCC tissue samples and paracancerous tissue samples. For example, the ESCC tissue samples are derived from the cancer tissue of the informed and consenting ESCC patient by surgical resection, and the paracancerous tissue samples are collected from the ESCC tissue at least 5 cm away from the esophageal tissue. Collection of the aforementioned tissue samples is performed within half an hour of the surgical excision or the biopsy. More specifically, in a sterile environment, the tissue sample from non-necrotic sites is cut, with its volume of more than 0.5 $mm^3$, and then the tissue sample is placed in pre-cooled 10-15 mL DMEM/F12 medium, which is contained in a plastic sterile centrifuge tube with a lid, and transported to the laboratory on ice. Wherein, the DMEM/F12 medium contains 1-2 vol % of penicillin, streptomycin, and/or 0.2-0.4 vol % of Primocin (hereinafter referred to as the tissue transport fluid). In case of using streptomycin/penicillin, the concentration range of streptomycin is 25-400 μg/mL, preferably 50-200 μg/mL, more preferably 200 μg/mL, the concentration range of penicillin is 25-400 U/mL, preferably 50-200 U/mL, more preferably 200 U/mL; and in case of using Primocin, the concentration range is 25-400 μg/mL, preferably 50-200 μg/mL, more preferably 100 μg/mL.

In a biological safety cabinet, the tissue sample is transferred to a cell culture dish, which is then rinsed with the transport fluid, and the blood cells on the surface of the tissue sample are washed away. The rinsed tissue sample is transferred to another new culture dish, with the addition of 1-3 mL of the transport fluid, and the tissue sample is divided into tissue fragments less than 3 $mm^3$ in volume using a sterile scalpel blade and a forceps.

The tissue sample fragments are transferred to a centrifuge tube, which is centrifuged at 1500 rpm for 3-5 minutes in a tabletop centrifuge (Sigma, 3-18K); after discarding the supernatant, the tissue transport fluid and the tissue digestive solution are added in a ratio of 1:1 (the dosage is about 5 mL of tissue digestive solution per 10 mg of tissue; the preparation method of the tissue digestive solution comprises: dissolving 1-2 mg/mL collagenase II, 1-2 mg/mL collagenase IV, 50-100 U/mL deoxyribonucleic acid I, 0.5-1 mg/mL hyaluronidase, 0.1-0.5 mg/mL calcium chloride, 5-10 mg/mL bovine serum albumin in HBSS and RPMI-1640 with a volume ratio of 1:1); then the sample is numbered and sealed with sealing film, and is then digested in a constant-temperature shaker (Zhichu Instrument ZQLY-180N) at 37° C., 200-300 revolutions; whether the digestion is completed is determined via observation every 1 hour; if no obvious tissue block is found, the digestion can be terminated; otherwise, it is continued for digestion until the digestion is sufficient, with the digestion time ranges from 4 to 8 hours. After digestion, undigested tissue blocks are filtered through a cell filter screen (the cell screen mesh size is, for example 70 μm); the tissue blocks on the filter screen are rinsed with the tissue transport fluid; the residual cells are rinsed into a centrifuge tube and centrifuged with a tabletop centrifuge at 1500 rpm for 3-5 minutes. After discarding the supernatant, the remaining cell clusters are observed to determine whether blood cells are remained; if there are blood cells, 3 mL blood cell lysate (purchased from Sigma) is added, which is then mixed well, lysed at 4° C. for 10-20 minutes, with shaking and mixing well once every 5 minutes; after lysis, the resultant is take out and centrifuged at 1500 rpm for 3-5 minutes. After discarding the supernatant, the primary cell culture medium of the invention is added for resuspension. The total number of cells is obtained by counting with a flow imaging counter (JIMBIO FIL, Jiangsu Jimbio Technology Co., Ltd.).

(4) Inoculating the primary ESCC epithelial cells isolated in step (3) in the coated culture vessel, and culturing by using the primary cell culture medium obtained in step (1).

More specifically, the primary ESCC tumor cells are inoculated at a density of $2\times10^4$ to $8\times10^4$ cells/$cm^2$ (e.g., $4\times10^4$ cells/$cm^2$) in one well of a 6-well plate; 2-3 mL of primary epithelial cell culture medium is added, and then is cultured in a cell incubator for 8-16 days, for example, under the conditions of 37° C., 5% $CO_2$; fresh primary cell culture medium is used for replacing every 4 days during the culture; digestion and passaging are performed when the primary ESCC epithelial cells grow to a cell density that accounts for about 80% to 90% of the bottom area of the 6-wll plate.

This inoculation step does not require the use of feeder cells, and compared to the cell conditional reprogramming technology, the operation steps of culturing and irradiating feeder cells are omitted. Compared to the organoid technology, this step does not need to mix the primary cells with the matrix gel uniformly on ice to form gel droplets and wait for the solidification of the gel droplets before adding the medium. The pre-coated culture vessel can be used directly for inoculation of the primary cells. In addition, only a small amount of diluted extracellular matrix gel is needed to coat culture vessels, which results to the saving of expensive extracellular matrix gel and simplification of the operation steps as compared with the organoid technology.

Optionally, after culturing the inoculated primary ESCC epithelial cells for 8-16 days, when the cell clones formed in the culture container converge to cover 80% of the bottom area, the supernatant is discarded, and 1-2 mL of 0.05% trypsin (purchased from Thermo Fisher) is added for cell digestion, which is then incubated at room temperature for 5-20 min. The digested cells are resuspended in 2-4 mL of culture liquid containing, for example, 5% (v/v) fetal bovine serum, 100 U/mL penicillin, and 100 μg/mL streptomycin, and are centrifuged at 1500 rpm for 3-5 minutes. The digested single cells are resuspended using the primary cell culture medium of the invention, and the obtained cell suspension is placed in a T25 cell culture flask coated with extracellular matrix gel for continuous culture. The coating operation of T25 cell culture flask is the same as that in step (2).

The expanded ESCC epithelial cells grow in 2D, avoiding the non-uniform size of organoids and internal necrosis in overgrown organoids that may occur in the expansion using organoid technology.

In another aspect, the ESCC epithelial cells, especially the ESCC tumor cells, cultured by the culturing method for primary ESCC epithelial cells of the invention, can be used for drug efficacy evaluation and drug screening, which comprises the following steps:

(1) Obtaining the primary ESCC epithelial cells, more preferably, obtaining the cancer tissue samples or the biopsy cancer tissue samples derived from the ESCC patients; isolating the primary ESCC epithelial cells, and culturing and expanding the primary ESCC epithelial cells (particularly the primary ESCC tumor cells) according to the method for culturing the primary ESCC epithelial cells described above to a cell number of at least the magnitudes of $10^5$, preferably at least the magnitudes of $10^6$.

(2) Selecting the drug for testing.

(3) Based on the maximum plasma concentration of the drug $C_{max}$ as a reference, taking 2-5 times of $C_{max}$ as the initial concentration, and diluting the drug into different drug concentration gradients, such as 5-10 drug concentration gradients, preferably 6-8 drug concentration gradients.

(4) Digesting the ESCC epithelium cells cultured in step (1) into a single cell suspension, counting the cell number with a flow imaging counter, diluting the single cell suspension with the primary cell culture medium of the invention, adding the diluted cell suspension evenly to the multi-well plate at a density of 2000-4000 cells per well, e.g., 50 μL of cell dilution per well, and adhering overnight.

This step avoids the problem of the cell reprogramming technique that the presence of feeder cells may interfere with the primary cell counting and the subsequent primary cell viability assay, and eliminates the need of the tedious step of mixing, embedding and then plating the cell suspension with matrix gel on ice as that in the organoid technique, which greatly simplifies the operation process and enhances the operability and practicality of the technology. Since the inoculated cells are single-cell suspensions rather than 3D structures like organoid, this technique may result in a more uniform number of plating cells and less variation in cell numbers between wells when compared to the organoid technique, making it more suitable for subsequent high-throughput drug screening operations.

(5) Adding the selected candidate drugs such as traditional chemotherapeutic drugs, targeted drugs, antibody drugs, or combination thereof with gradient dilutions, to the adherent cells obtained in step (4), using a high-throughput automated workstation.

(6) After a few hours of drug addition, for example, 72 hours, detecting the survival rate of the ESCC epithelial cells using the Cell-Titer Glo luminescence cell viability detection kit (purchased from Promega) to screen for drug activity.

Specifically, each well is added with, for example, 10 μL of Cell Titer-Glo reagent (purchased from Promega), and after uniformly shaking, the chemiluminescence intensity of each well is measured with a fluorescence microplate reader. Taking the drug concentration as the abscissa and the fluorescence intensity as the ordinate, GraphPad Prism software is used to draw the drug dose-effect curve based on the measured values, and the inhibitory intensity of the drugs on the proliferation of the tested cells are calculated.

When using the primary ESCC tumor cells of the invention in drug screening and in vitro drug sensitivity test, since it is not a cell co-culture system, the phenomenon that feeder cells in the cell reprogramming technology interfere with the test results will not occur. Due to the 2D growth of the cells, the interaction with the drug is also quicker than the drug test time in the organoid technology (the average administration time in the organoid technology is 6 days).

The beneficial effects of the invention also include:

(1) the success rate for culturing the primary ESCC epithelial cell can be improved, with a success rate of more than 80%;

(2) the ESCC epithelial cells primary cultured in vitro can be ensured to reproduce the pathological phenotype and the heterogeneity of the owner patient of the primary cells;

(3) the primary ESCC epithelial cells cultured are pure ESCC epithelial cells which are not interfered by fibroblasts;

(4) the composition of the medium does not contain serum, and thus, it is not affected by the quality and the quantity of the serum from different batches;

(5) the ESCC epithelial cells can be expanded with high efficiency, with a magnitude of $10^6$ of ESCC epithelial cells being successfully expanded within about two weeks from the starting of $10^4$-level cell count, and the expanded ESCC epithelial cells have the ability of continuous passage;

(6) there is no need to operate on ice and to dissociate the matrix gel in the passage step, and the digestion and passage of cells can be completed within 10-15 minutes;

(7) the cost for culture is controllable, as the primary ESCC culture medium does not require expensive Wnt agonists, R-spondin family proteins, BMP inhibitors and the like factors, and thus, it is a simplification and improvement of the existing organoid culture medium for primary ESCC epithelial cells; and the cell inoculation does not need to use a higher concentration of extracellular matrix for mixing with the primary cells to form gel droplets, but instead, only a small amount of extracellular matrix gel dilution is required, which saves the amount of costly extracellular matrix;

(8) the operations are convenient: compared with the conditional reprogramming technology, this technology does not need to cultivate or irradiate the feeder cells, which avoids the problem that the quality and the quantity of feeder cells from different batches may affect the efficiency of primary cell culture, and the plating and testing objects in the drug screen are only primary ESCC epithelial cells, without the interference of feeder cells in the co-culture system as described in the cell conditional reprogramming technology; compared with the organoid technology, in the method for coating extracellular matrix gel adopted in the invention, the culture vessel can be prepared in advance, and there is no need to embed cells in the matrix gel as in the organoid technology, and the operation steps are simple and easy;

(9) this technology can culture and provide the ESCC epithelial cells with large quantity and high uniformity, which is suitable for high-throughput screening of new candidate compounds and high-throughput drug sensitivity functional tests in vitro for patients.

Using the cell culture medium of this embodiment, the ESCC epithelial cells derived from humans or other mammals, including ESCC tumor cells, normal esophageal epithelial cells, ESCC epithelial stem cells, or tissues comprising at least any of these cells, can be cultured. At the same time, the culture medium of the invention can also be used to develop a kit for expansion and culture of primary ESCC cells in vitro.

Furthermore, the cells obtained by the culture method of this embodiment can be used in regenerative medicine, basic medical research of ESCC epithelial cells, screening of drug responses, and development of new drugs for ESCC diseases, and the like.

DESCRIPTION OF DRAWINGS

The patent or application file contains at least one drawing executed in color. Copies of this paper or patent application publication with color drawing(s) will be provided by the Office upon request and payment of the necessary fee.

FIGS. 4A and 4B are photographs of ESCC tumor cells taken under an inverted microscope, which were cultured from the cells isolated from one clinical ESCC tissue sample (No. 0F0062), by using the culture medium FEM of the invention, to Day 4 and Day 12, respectively.

FIGS. 5A and 5B are microscopic photographs of cells which were cultured from the primary ESCC tumor cells originated from one ESCC tissue (No. 0F0065) to Day 11, under conditions of coating with extracellular matrix gel Matrigel and without coating with Matrigel, respectively.

FIGS. 6A-6E are photographs of cells taken under an inverted microscope, which were cultured from the cells isolated from one surgically resected ESCC sample (No. 0F0060) for 14 days under five different culture mediums.

FIG. 7 is a comparative diagram of cell proliferation effects obtained by culturing the cells isolated from six surgically resected ESCC samples (No. 0F0056, 0F0060, 0F0061, 0F0062, 0F0071, 0F0075) for 16 days under the conditions of five different culture mediums.

FIG. 8 is a comparative diagram of cell growth curves obtained by culturing the cells isolated from one clinical ESCC tissue sample (No. 0F0075) under the conditions of five different culture mediums.

FIGS. 9A-9D are microscopic photographs of cells cultured from the cells isolated from one clinical ESCC tissue sample (No. 0E0075) to the 1st and the 9th passages under FEM and EPI culture conditions, respectively.

FIGS. 10A and 10B are comparison of immunohistochemical results of one surgically resected ESCC sample (No. 0F0053) and the ESCC tumor cells obtained by culturing the cells isolated from the sample (No. 0F0053) with the culture medium FEM of the invention, respectively.

FIGS. 11A-11D are comparison of copy number variation analysis results of one surgically resected ESCC sample (No. 0F0025) and the ESCC tumor cells of different passages obtained by culturing the cells isolated from the sample (No. 0F0025) with the culture medium FEM of the invention, respectively.

FIGS. 13A-13H are microscopic photographs of cells obtained by culturing the cells isolated from one clinical ESCC tissue sample (No. 0F0061) to the third passage, under the conditions of the culture medium FEM of the invention and the culture mediums obtained by subtracting different components, respectively.

DETAILED DESCRIPTION OF THE INVENTION

Figure 1A:
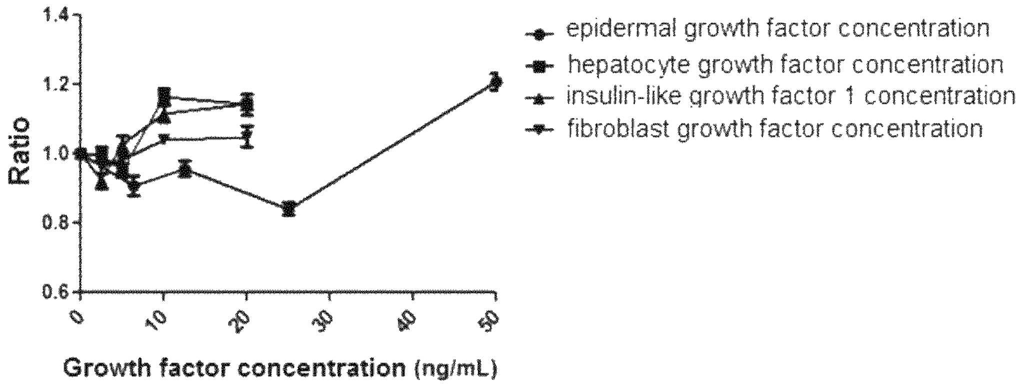
FIGS. 1A-1E show the effects of different factors in the culture medium on the proliferation of primary ESCC cells.
Figure 1B:
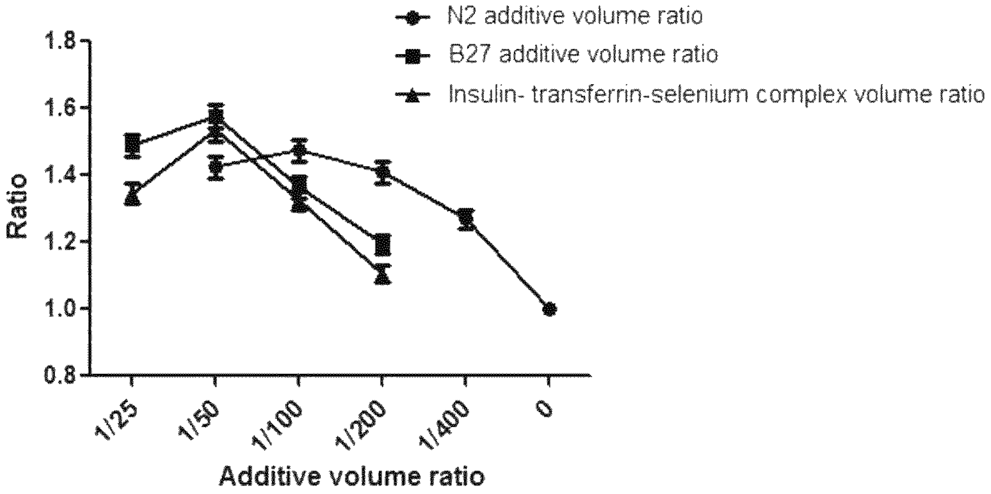
Figure 1C:
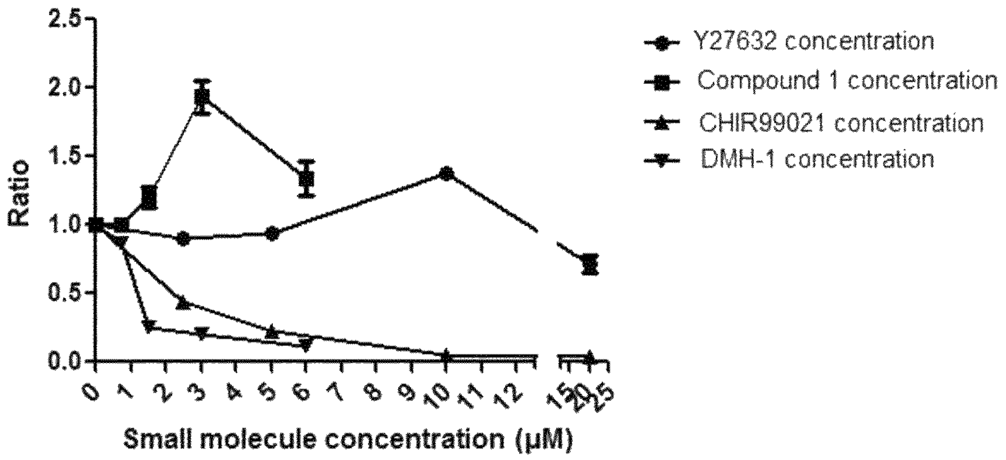
Figure 1D:
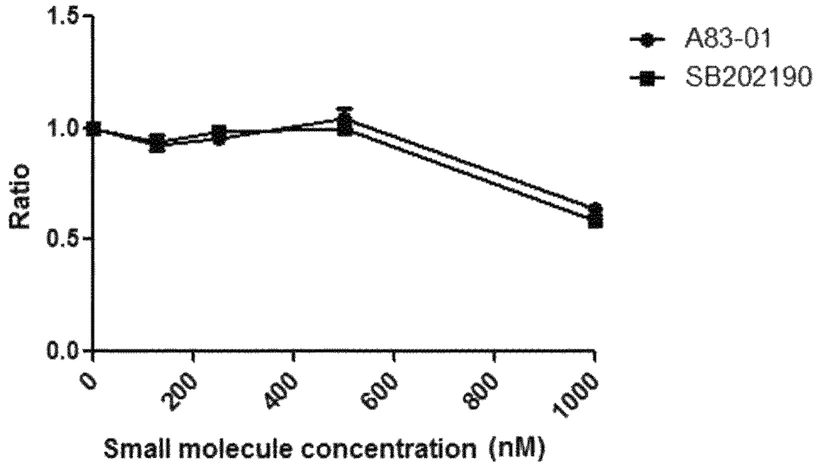
Figure 1E:
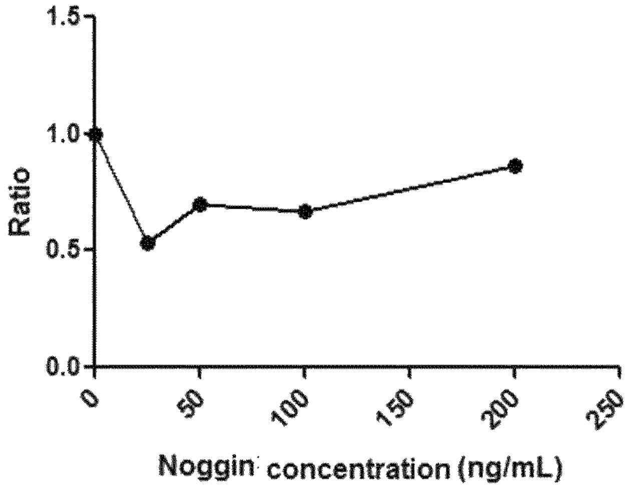

In the specification, the epithelial cells include differentiated epithelial cells and epithelial stem cells obtained from epithelial tissues. "Epithelial stem cells" refer to the cells with long-term self-renewal ability that may differentiate into epithelial cells, and the stem cells originated from epithelial tissues. Examples of epithelial tissues include cornea, oral mucosa, skin, conjunctiva, bladder, renal tubule, kidney, digestive organs (esophagus, stomach, duodenum, small intestine (including jejunum and ileum), large intestine (including colon)), liver, pancreas, mammary gland, salivary gland, lacrimal gland, prostate, hair root, trachea, lung, etc. Among others, the cell culture medium of the embodiment is preferably the culture medium for epithelial cells derived from esophagus.

In addition, in this specification, "epithelial tumor cells" refer to the cells obtained by tumorigenesis of cells originated from the aforementioned epithelial tissues.

In the specification, "organoid" refers to a three-dimensional, organ-like cellular tissue formed by spontaneously organizing and aggregating cells within a controlled space in high density.

Preparation Examples of MST1/2 Kinase Inhibitors

In the specification, MST1/2 kinase inhibitor refers to any inhibitor that directly or indirectly negatively regulates MST1/2 signaling. Generally, MST1/2 kinase inhibitors reduce the activity of MST1/2 kinase by, for example, binding to the same. Since MST1 and MST2 have similar structures, MST1/2 kinase inhibitors may be, for example, compounds that bind to MST1 or MST2 and reduce the activity thereof.

1. Preparation of MST1/2 Kinase Inhibitor Compound 1 4-((7-(2,6-difluorophenyl)-5,8-dimethyl-6-oxo-5,6,7,8-tetrahydropteridin-2-yl) amino)benzsulfamide 1

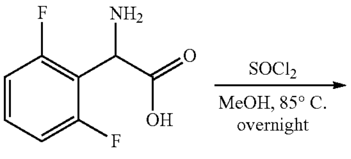

A1

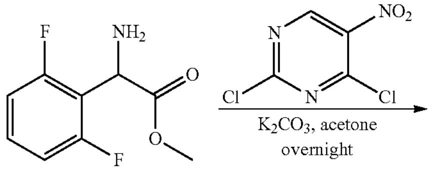

A2

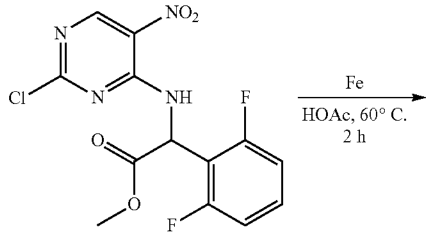

A3

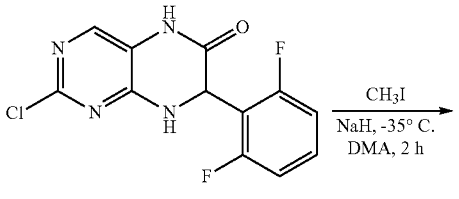

A4

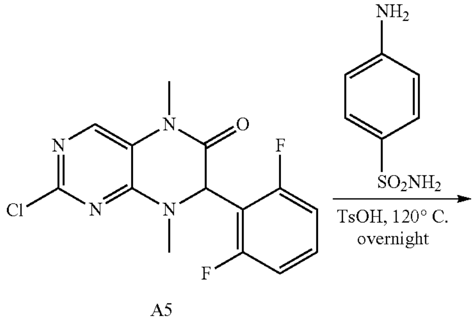

A5

-continued

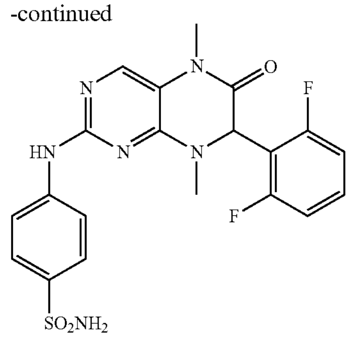

1

Methyl 2-amino-2-(2,6-difluorophenyl)acetate (A2): 2-amino-2-(2,6-difluorophenyl)acetic acid (2.0 g) and then methanol (30 ml) were added into a round bottom flask, followed by addition of thionyl chloride (1.2 ml) dropwise under an ice bath. The reaction system was reacted overnight at 85° C. After the completion of the reaction, the system was evaporated under reduced pressure to dry the solvent, and the obtained white solid was directly used in the next step.

Methyl 2-((2-chloro-5-nitropyrimidin-4-yl)amino)-2-(2,6-difluorophenyl) acetate (A3): methyl 2-amino-2-(2,6-difluorophenyl)acetate (2 g) and then acetone (30 ml) and potassium carbonate (2.2 g) were added into a round bottom flask, and then the system was cooled to −10° C. with an ice salt bath, and then a solution of 2,4-dichloro-5-nitropyrimidine (3.1 g) in acetone was slowly added. The reaction system was stirred overnight at room temperature. After the completion of the reaction, the reaction mixture was filtered, the solvent was removed from the filtrate under reduced pressure, and the residue was purified by pressurized silica gel column chromatography to obtain compound A3. LC/MS: M+H 359.0.

2-chloro-7-(2,6-difluorophenyl)-7,8-dihydropteridin-6(5H)-one (A4): methyl 2-((2-chloro-5-nitropyrimidin-4-yl) amino)-2-(2,6-difluorophenyl)acetate (2.5 g) and then acetic acid (50 ml) and iron powder (3.9 g) were added into a round bottom flask. The reaction system was stirred at 60° C. for two hours. After the completion of the reaction, the reaction system was evaporated under reduced pressure to dry the solvent, and the resultant was neutralized to be alkaline with saturated sodium bicarbonate solution and was extracted with ethyl acetate. The organic phase was washed with water and saturated brine and dried with anhydrous sodium sulfate. The organic phase was filtered and evaporated to dryness under reduced pressure to obtain a crude product. The crude product was washed with diethyl ether to obtain compound A4. LC/MS: M+H 297.0.

2-chloro-7-(2,6-difluorophenyl)-5,8-dimethyl-7,8-dihydropteridin-6(5H)-one (A5): 2-chloro-7-(2,6-difluorophenyl)-7,8-dihydropteridin-6(5H)-one (2 g) and N,N-dimethylacetamide (10 ml) were added into a round bottom flask, and cooled to −35° C., followed by addition of iodomethane (0.9 ml) and then sodium hydride (615 mg), and the reaction system was stirred for two hours. After the completion of the reaction, the reaction mixture was quenched with water, and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was washed with diethyl ether to obtain compound A5. LC/MS: M+H 325.0.

4-((7-(2,6-difluorophenyl)-5,8-dimethyl-6-oxo-5,6,7,8-tetrahydropteridin-2-yl)amino)benzsulfamide (1): 2-chloro-7-(2,6-difluorophenyl)-5,8-dimethyl-7,8-dihydropteridin-6(5H)-one (100 mg), sulfanilamide (53 mg), p-toluenesulfonic acid (53 mg) and sec-butanol (5 ml) were added into a round bottom flask. The reaction system was stirred at 120° C. overnight. After the completion of the reaction, the reaction mixture was filtered, and washed with methanol and diethyl ether to obtain compound 1. LC/MS: M+H 461.1.

2. Preparation of Other MST1/2 Inhibitor Compounds of the Invention

Other MST1/2 inhibitor compounds of the invention were synthesized via the method similar to that of Compound 1, and their structures and mass spectrum data are shown in the following table.

| No. | Compound | MS(ESI) m/z (M + 1)+ |
|---|---|---|
| 1 | 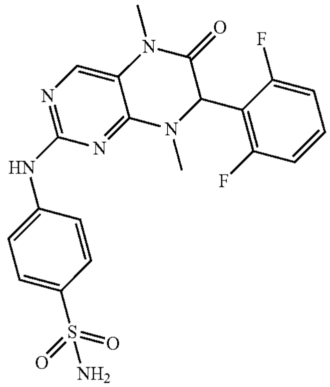 | 461.1 |
| 2 | 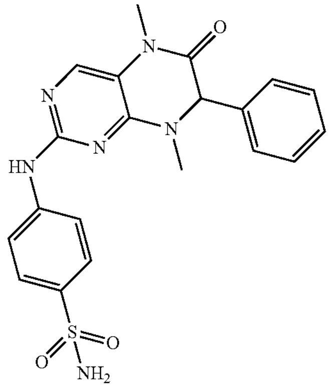 | 425.14 |
| 3 | 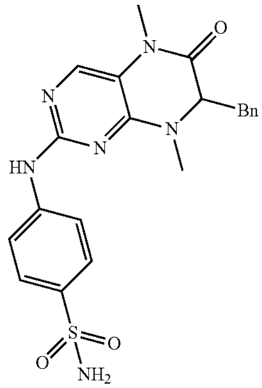 | 439.15 |

-continued

| No. | Compound | MS(ESI) m/z (M + 1)+ |
|---|---|---|
| 4 | 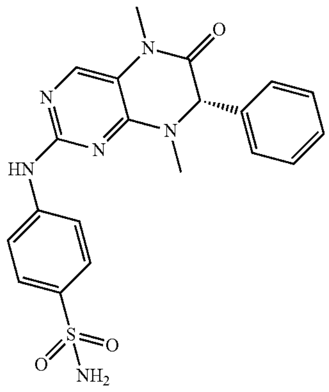 | 425.14 |
| 5 | 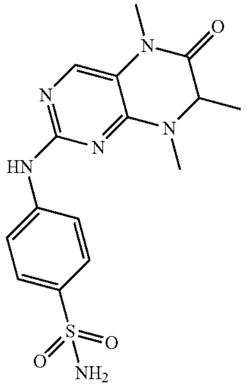 | 363.12 |
| 6 | 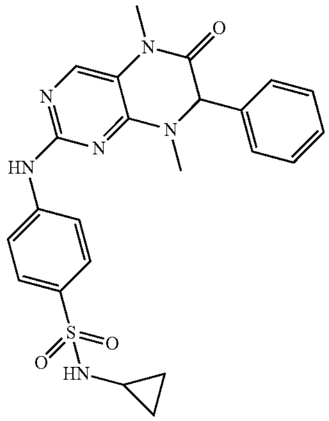 | 465.17 |

-continued
| No. | Compound | MS(ESI) m/z (M + 1)+ |
|---|---|---|
| 7 | 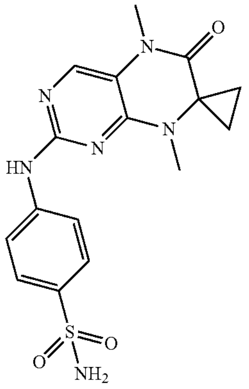 | 375.12 |
| 8 | 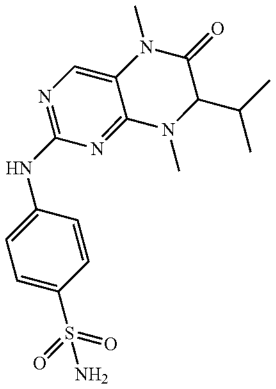 | 391.16 |
| 9 | 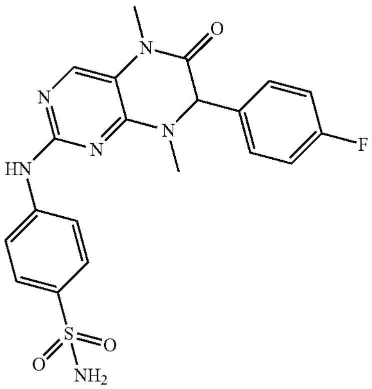 | 443.13 |
| 10 | 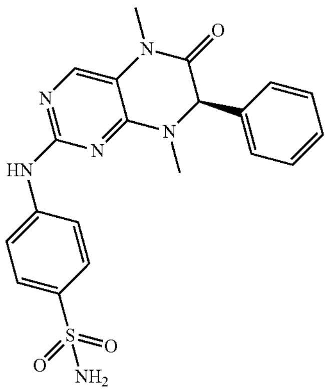 | 425.14 |
| 11 | 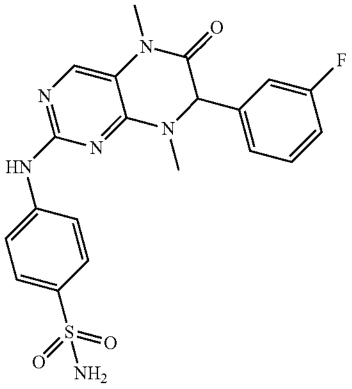 | 443.13 |
| 12 | 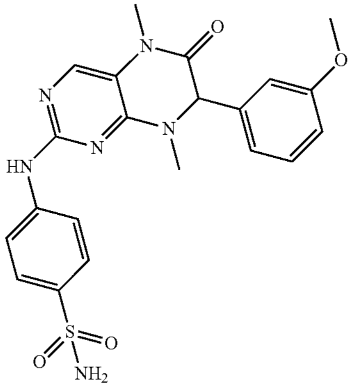 | 455.15 |
| 13 | 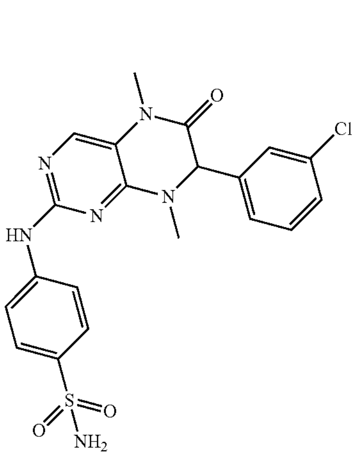 | 459.10 |

-continued
| No. | Compound | MS(ESI) m/z (M + 1)+ |
|---|---|---|
| 14 | 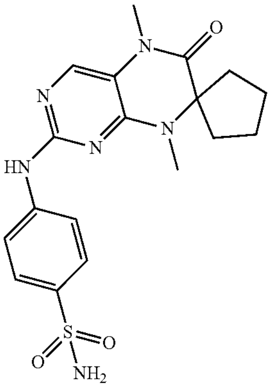 | 403.15 |
| 15 | 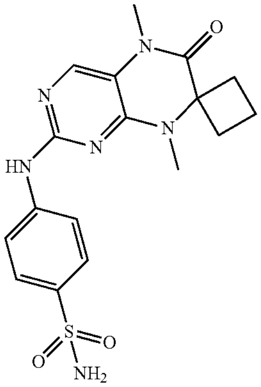 | 389.14 |
| 16 | 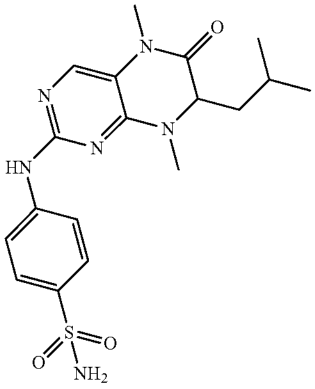 | 405.17 |
| 17 | 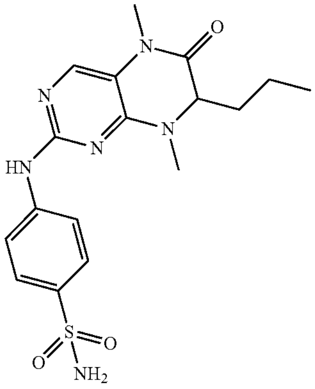 | 391.15 |
-continued
| No. | Compound | MS(ESI) m/z (M + 1)+ |
|---|---|---|
| 18 | 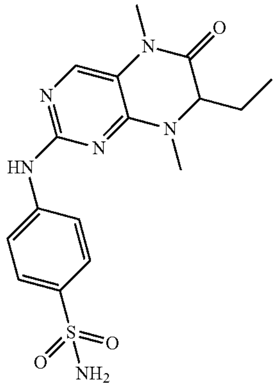 | 377.14 |
| 19 | 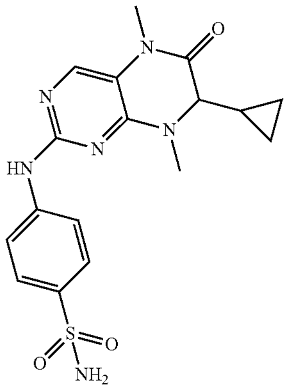 | 389.14 |
| 20 | 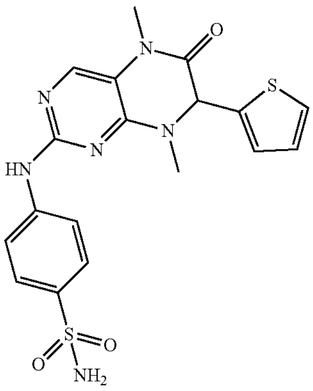 | 431.09 |

-continued
| No. | Compound | MS(ESI) m/z (M + 1)+ |
|---|---|---|
| 21 | 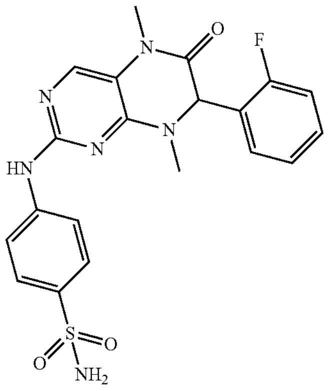 | 443.13 |
| 22 | 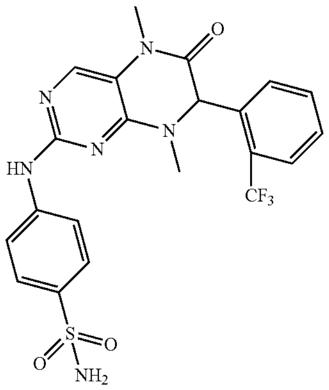 | 493.12 |
| 23 | 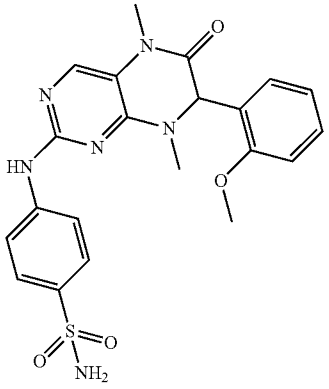 | 455.15 |
| 24 | 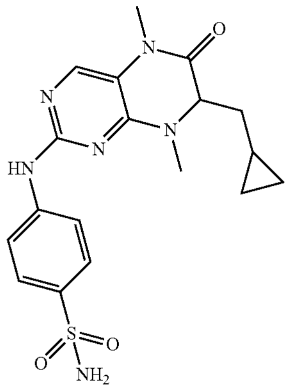 | 403.15 |
-continued
| No. | Compound | MS(ESI) m/z (M + 1)+ |
|---|---|---|
| 25 | 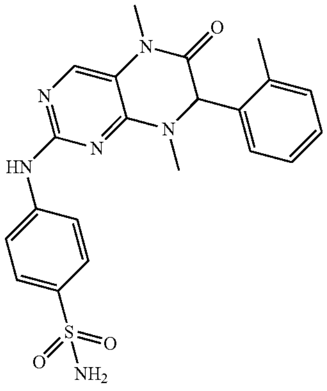 | 439.15 |
| 26 | 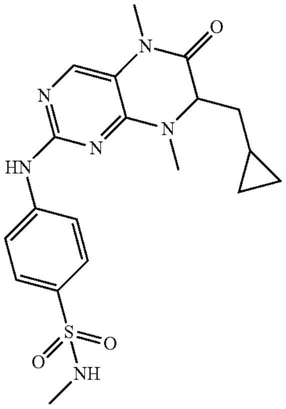 | 417.17 |
| 27 | 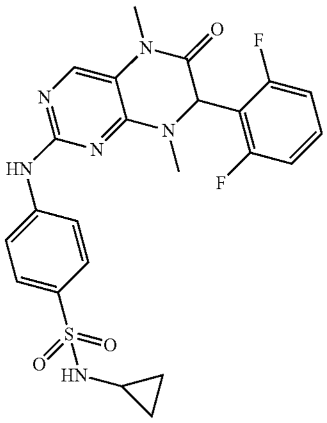 | 501.15 |

-continued
| No. | Compound | MS(ESI) m/z (M + 1)+ |
|---|---|---|
| 28 | 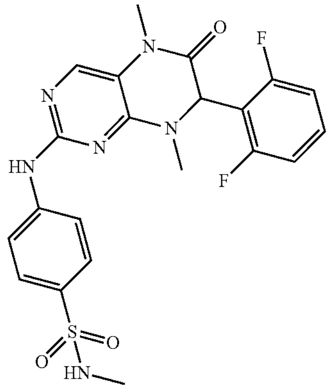 | 475.13 |
| 29 | 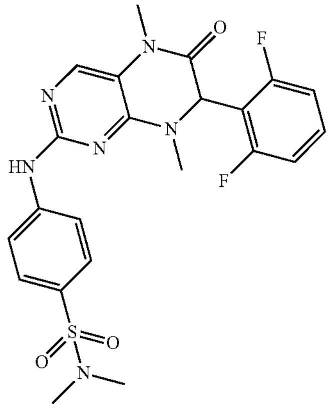 | 489.15 |
| 30 | 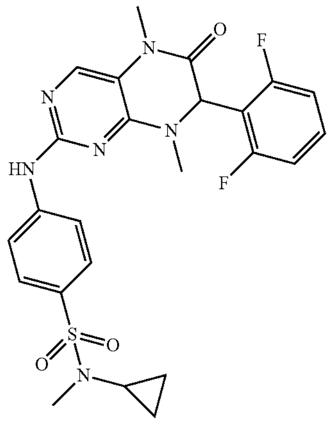 | 515.16 |
| 31 | 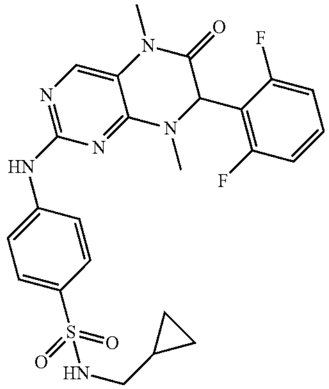 | 515.16 |
| 32 | 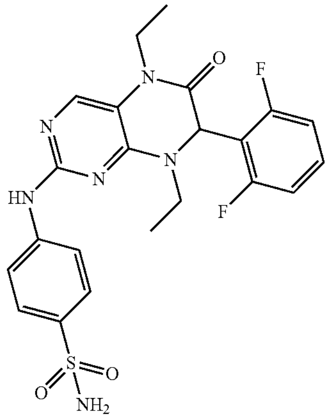 | 489.15 |
| 33 | 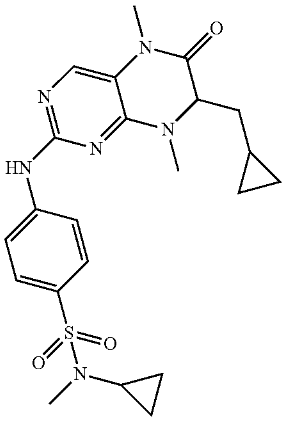 | 457.20 |

-continued
| No. | Compound | MS(ESI) m/z (M + 1)+ |
|---|---|---|
| 34 | 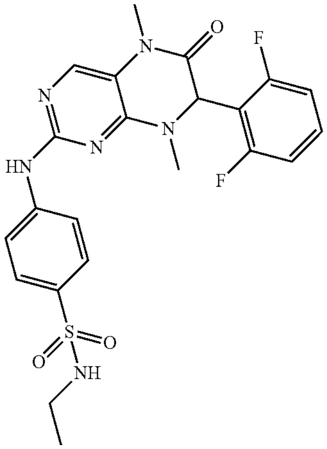 | 489.15 |
| 35 | 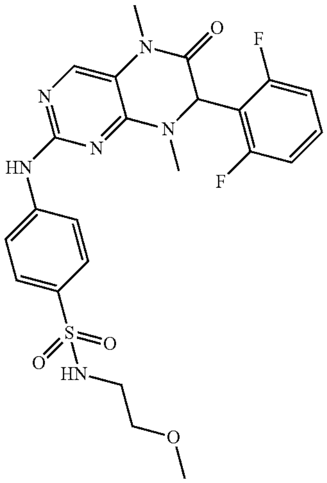 | 519.16 |
| 36 | 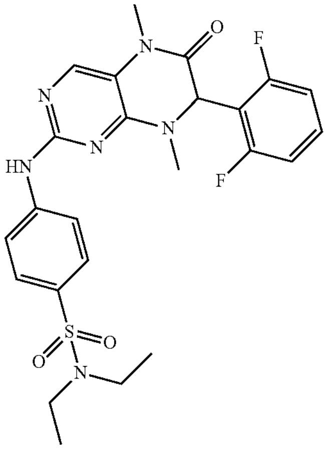 | 517.18 |
-continued
| No. | Compound | MS(ESI) m/z (M + 1)+ |
|---|---|---|
| 37 | 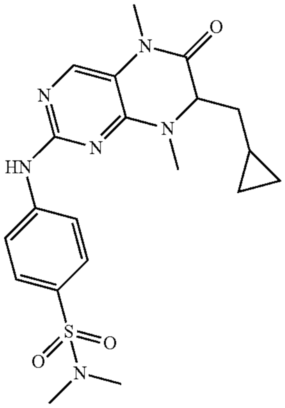 | 431.18 |
| 38 | 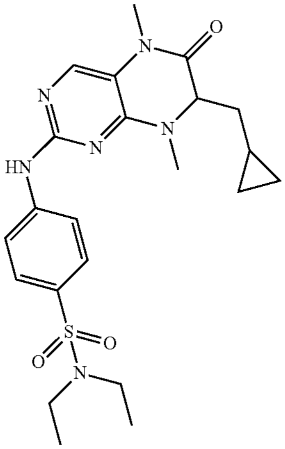 | 459.21 |
| 39 | 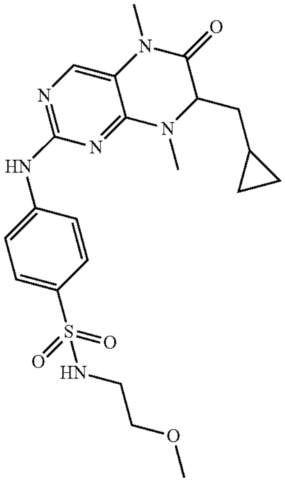 | 461.19 |

-continued
| No. | Compound | MS(ESI) m/z (M + 1)+ |
|---|---|---|
| 40 | 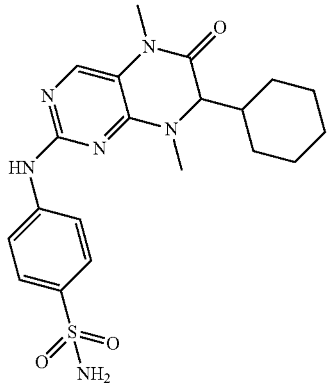 | 431.19 |
| 41 | 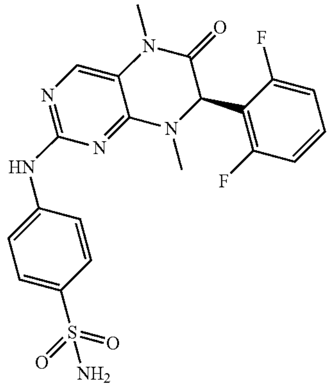 | 461.12 |
| 42 | 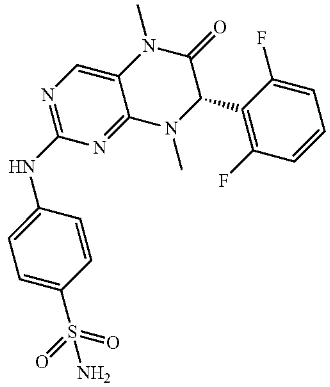 | 461.12 |
| 43 | 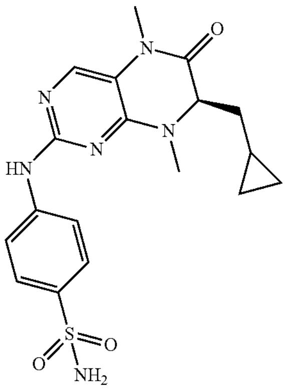 | 403.15 |
-continued
| No. | Compound | MS(ESI) m/z (M + 1)+ |
|---|---|---|
| 44 | 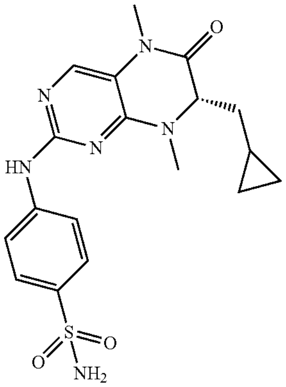 | 403.15 |
| 45 | 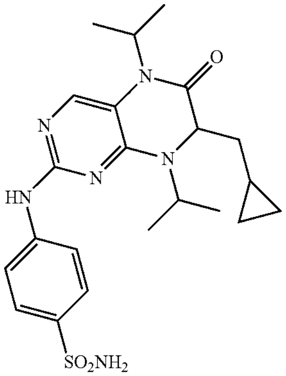 | 459.21 |
| 46 | 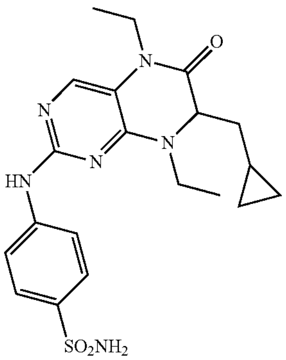 | 431.18 |

| No. | Compound | MS(ESI) m/z (M + 1)+ |
|---|---|---|
| 47 | 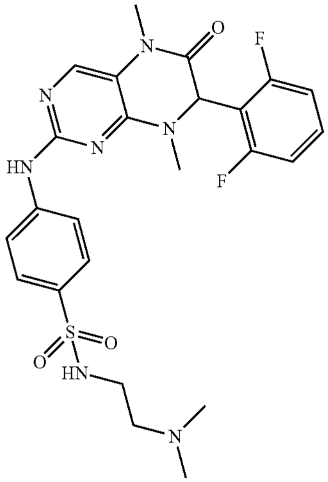 | 532.19 |
| 48 | 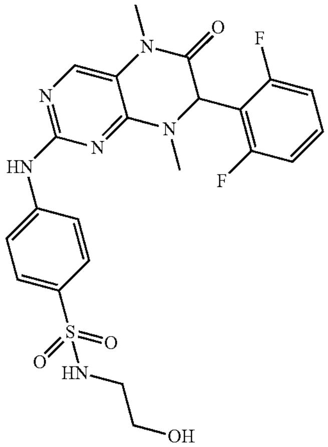 | 505.14 |
| 49 | 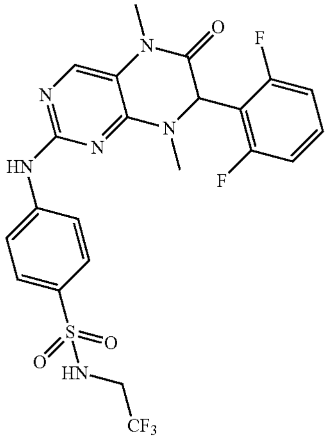 | 543.12 |
| No. | Compound | MS(ESI) m/z (M + 1)+ |
|---|---|---|
| 50 | 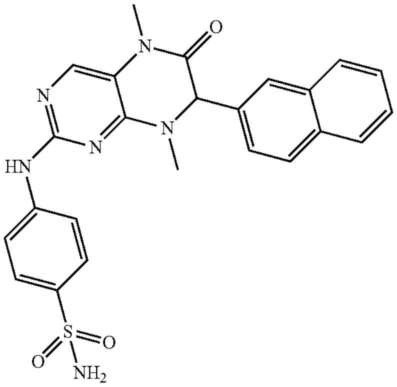 | 475.16 |
| 51 | 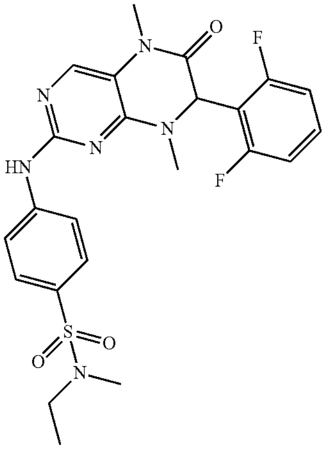 | 503.17 |
| 52 | 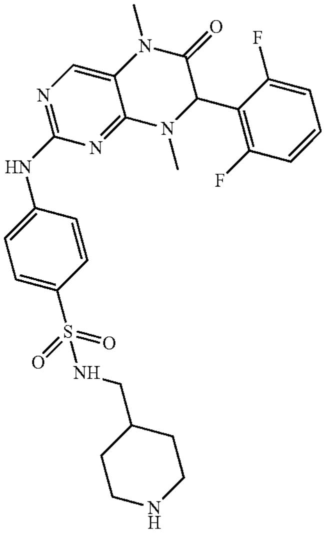 [SMILES: CN1C(=O)C(c2c(F)cccc2F)N(C)c2nc(Nc3ccc(S(=O)(=O)NCC4CCNCC4)cc3)ncc21] | 558.21 |

-continued
| No. | Compound | MS(ESI) m/z (M + 1)+ |
|---|---|---|
| 53 | 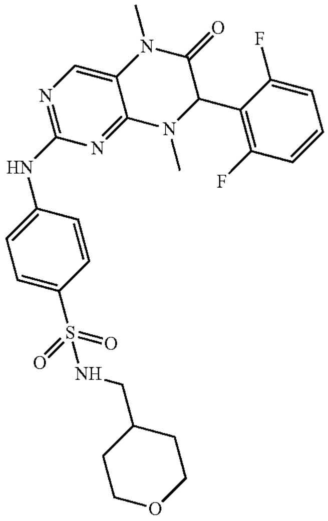 [SMILES: CN1C(=O)C(c2c(F)cccc2F)N(C)c2nc(Nc3ccc(S(=O)(=O)NCC4CCOCC4)cc3)ncc21] | 559.19 |
| 54 | 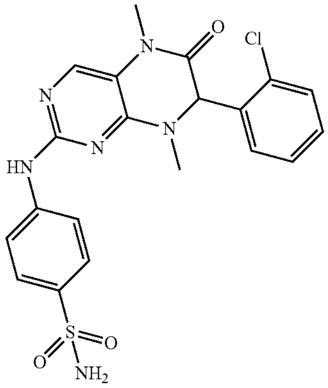 | 459.10 |
| 55 | 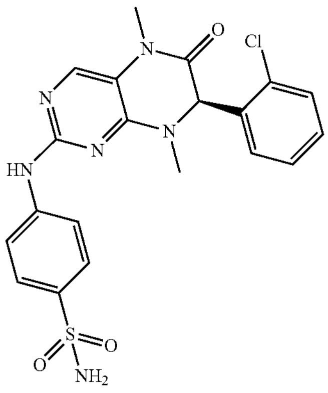 [SMILES: CN1C(=O)[C@@H](c2ccccc2Cl)N(C)c2nc(Nc3ccc(S(N)(=O)=O)cc3)ncc21] | 459.10 |
-continued
| No. | Compound | MS(ESI) m/z (M + 1)+ |
|---|---|---|
| 56 | 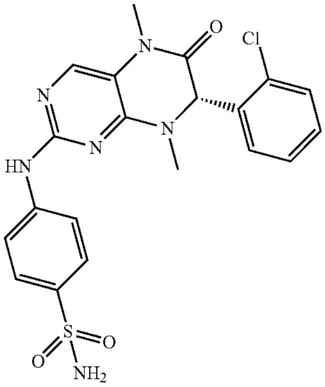 | 459.10 |
| 57 | 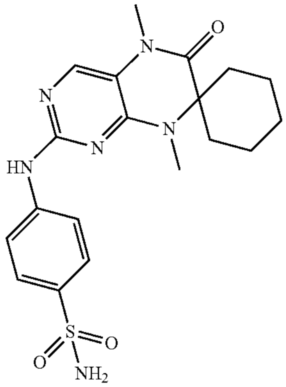 [SMILES: CN1C(=O)C2(CCCCC2)N(C)c2nc(Nc3ccc(S(N)(=O)=O)cc3)ncc21] | 417.17 |
| 58 | 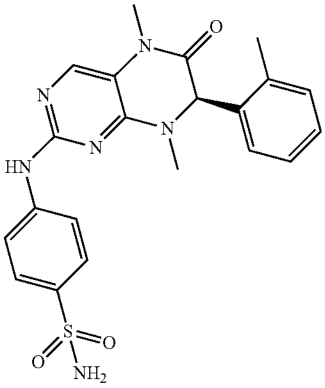 [SMILES: Cc1ccccc1[C@@H]1C(=O)N(C)c2cnc(Nc3ccc(S(N)(=O)=O)cc3)nc2N1C] | 439.16 |
| 59 | 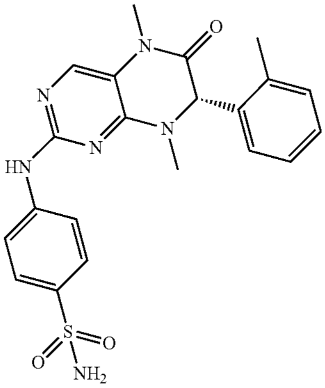 | 439.16 |

Example 1

Isolation of Human Primary ESCC Epithelial Cells

ESCC tissue samples were obtained from the cancer tissues of three informed and consenting ESCC cancer patients by surgical resection, namely Sample Nos. 0F0060, 0F0061, and 0F0062. One of the samples (No. 0F0060) will be described below.

The aforementioned tissue samples were collected within half an hour after the surgical excision or the biopsy. More specifically, in a sterile environment, tissue samples from non-necrotic sites were cut with a volume of more than 0.5 $cm^3$ and were placed in 4 mL of pre-cooled tissue transport fluid (specific formulation shown in Table 1). The transport fluid was placed in a 5 mL plastic sterile cryopreservation tube with a lid (purchased from Guangzhou Jet Bio-Filtration Co., Ltd.) and cold chain (0-10° C.) transported to the laboratory.

TABLE 1

Formulation of tissue transport fluid

| Components of tissue transport fluid | Supplier | Final concentration |
|---|---|---|
| DMEM/F12 | Corning | 97.8 vol. % |
| Primocin | Invivogen | 0.2 vol. % (concentration of commercial product: 50 mg/ml) |
| penicillin/streptomycin solution double antibody | Corning | 2 vol. % (concentration of commercial product: 10000 U/ml penicillin, 10 mg/ml streptomycin) |

TABLE 2

Fumulation of tissue digestive solution

| Components of tissue digestive solution | Supplier | Final concentration |
|---|---|---|
| HBSS | Gibco | 50 vol. % |
| RPMI-1640 | Corning | 50 vol. % |
| collagenase II | Sigma | 2 mg/mL |
| collagenase IV | Sigma | 2 mg/mL |
| deoxyribonucleic acid I | Sigma | 50 U/mL |
| hyaluronidase | Sigma | 0.5 mg/mL |
| calcium chloride | Sangon Biotech | 0.33 mg/mL |
| bovine serum albumin | Sangon Biotech | 10 mg/mL |

In the biological safety cabinet, the tissue sample (No. 0F0060) was transferred to a 100 mm cell culture dish (purchased from NEST). The tissue sample was rinsed with the tissue transport fluid. The residual blood on the surface of the tissue sample was washed away. Excess tissues such as fat on the surface of the tissue sample were removed. The rinsed tissue sample was transferred to another new 100 mm culture dish; 2 mL of transport fluid was added, and a sterile scalpel blade and a forceps were used to divide the tissue sample into tissue fragments less than 3 $mm^3$ in volume.

The tissue sample fragments were transferred to a 15 mL centrifuge tube, and centrifuged at 1500 rpm for 4 minutes in a tabletop centrifuge (Sigma, 3-18K); after discarding the supernatant, the tissue transport fluid and the tissue digestive solution were added in a ratio of 1:1 (the dosage is about 5 mL of tissue digestive solution per 10 mg of tissue; specific formulation was shown in Table 2); then the sample was numbered and sealed with sealing film, and was then digested in a constant-temperature shaker (Zhichu Instrument ZQLY-180N) at 37° C., 300 revolutions; whether the digestion was completed was determined via observation every 1 hour.

After digestion, undigested tissue blocks were filtered through a 70 μm filter screen; the tissue blocks on the filter screen were rinsed with the tissue transport fluid; the residual cells were rinsed into a centrifuge tube and centrifuged at 1500 rpm for 4 minutes.

After discarding the supernatant, the remaining cell clusters were observed to determine whether blood cells were remained; if there were blood cells, 3 mL blood cell lysate (purchased from Sigma) was added, which was then mixed well, lysed at 4° C. for 15 minutes, with shaking and mixing well once every 5 minutes; after lysis, the resultant was take out and centrifuged at 1500 rpm for 4 minutes. The supernatant was discarded to provide digested and isolated primary ESCC cells, which were added with basic medium (BM) for resuspension. The basic medium was prepared by adding 0.2 vol. % of Primocin (purchased from Invivogen, with a concentration of 50 mg/mL) to the commercial DMEM/F-12 medium to provide a final concentration of 100 μg/mL. The total number of cells was 2,280,000, which was obtained by counting with a flow imaging counter (JIMBIO FIL, Jiangsu Jimbio Technology Co., Ltd.).

Other two ESCC tumor tissue samples were isolated according to the same method above, and the total number of cells were 1,470,000 (0F0061) and 2,680,000 (0F0062), respectively.

Example 2

Optimization of Culture Medium for Primary ESCC Epithelial Cell (1) Effects of Different Factors Extracellular matrix gel (Matrigel®) (manufactured by BD Biosciences) was diluted at 1:100 in serum-free DMEM/F12 medium to prepare an extracellular matrix dilution, which was added to a 48-well culture plate with 500 μl/well to completely cover the bottom of the wells of the culture plate. The resultant was let stand for 1 hour in a 37° C. incubator. After 1 hour, the extracellular matrix dilution was removed to provide a Matrigel-coated plate.

Preparation of basic medium (abbreviated as BM): BM was prepared by adding 0.2 vol. % of Primocin (purchased from Invivogen, with a concentration of 50 mg/mL) to the commercial DMEM/F-12 medium to provide a final concentration of 100 μg/mL.

Next, different kinds and concentrations of additive factors (Table 3) were added to the basic medium (BM), so as to prepare culture mediums for ESCC epithelial cells containing different additive components.

TABLE 3

Preparation of culture mediums containing different components (final concentrations are shown)

| Culture medium | Sources of additive factors | Composition |
|---|---|---|
| Basic medium/BM | | DMEM/F12 + 100 μg/mL Primocin |
| BM + epidermal growth factor (EGF) | Sino Biological | BM + 50, 25, 12.5, 7.5 ng/ml EGF |
| BM + hepatocyte growth factor (HGF) | Sino Biological | BM + 20, 10, 5, 2.5 ng/ml HGF |
| BM + insulin-like growth factor 1 (IGF-1) | Sino Biological | BM + 20, 10, 5, 2.5 ng/ml IGF-1 |
| BM + fibroblast growth factor (FGF) | Sino Biological | BM + 20, 10, 5, 2.5 ng/ml FGF |
| BM + N2 additive | Gibco | BM + 1/50, 1/100, 1/200, 1/400 diluting ratio of N2 |
| BM + B27 additive | Gibco | BM + 1/25, 1/50, 1/100, 1/200 diluting ratio of B27 |
| BM + insulin-transferrin-selenium complex (ITS) | Insulin, transferrin, sodium selenite all purchased from Sigma | BM + 1/25, 1/50, 1/100, 1/200 diluting ratio of insulin-transferrin-selenium complex stock solution (the stock solution contains 500 μg/ml insulin, 250 μg/ml transferrin, and 250 ng/ml sodium selenite in DMEM/F-12) |
| BM + Y27632 | MCE | BM + 20, 10, 5, 2.5 μM Y27632 |
| BM + Compound 1 | Preparation Example | BM + 6, 3, 1.5, 0.75 μM Compound 1 |
| BM + CHIR99021 | MCE | BM + 20, 10, 5, 2.5 μM CHIR99021 |
| BM + DMH-1 | MCE | BM + 6, 3, 1.5, 0.75 μM DMH-1 |
| BM + A83-01 | MCE | BM + 1000, 500, 250, 125 nM A83-01 |
| BM + SB202190 | MCE | BM + 1000, 500, 250, 125 nM SB202190 |
| BM + Noggin | Sino Biological | BM + 200, 100, 50, 25 ng/ml Noggin |

The culture mediums with different components were added at a volume of 500 μl/well to 48-well plates which were coated with extracellular matrix gel (Matrigel). ESCC tumor cells (No. 0F0064) isolated from ESCC tissue according to the same method described in Example 1 were inoculated in a Matrigel-coated 48-well culture plate at a cell density of $2\times10^4$ cells/$cm^2$. After surface disinfection, the plate was placed in a 37° C., 5% $CO_2$ incubator (purchased from Thermo Fisher), such that equal numbers of freshly isolated ESCC tumor cells (No. 0F0064) were cultured under different medium formulations. The culture mediums were renewed every 4 days after the start of the culture. After 12 days of culture, cell counts were performed. As an experiment control, the basis medium (BM) without any additive was used. The results were shown in FIGS. 1A-1E. The ordinate in each figure represents the ratio of the number of cells obtained after culture in different mediums to the number of cells obtained after culture in basic medium BM. As shown in the figures, the addition of different concentrations of different factors as shown in Table 3 to BM has different effects on cell proliferation. Among others, B27 additive, N2 additive, insulin-transferrin-selenium complex, epidermal growth factor, hepatocyte growth factor, insulin-like growth factor 1, Compound 1 and Y27632 have promoting effects on cell proliferation in certain concentration ranges.

(2) Effects of Combination of Y27632 and Compound 1

Extracellular matrix gel (Matrigel®) (purchased from BD Biosciences) was diluted at 1:100 in serum-free DMEM/F12 medium to prepare an extracellular matrix dilution, which was added to a 48-well culture plate with 500 μl/well to completely cover the bottom of the wells of the culture plate. The resultant was let stand for 1 hour in a 37° C. incubator. After 1 hour, the extracellular matrix dilution was removed to provide a Matrigel-coated plate.

Different concentrations of Y27632 and Compound 1 (Table 4) were added to the basic medium BM, so as to prepare culture mediums for ESCC epithelial cells containing different additive components.

TABLE 4

Preparation of culture mediums containing different components (final concentrations are shown)

| Medium NO. | Composition |
|---|---|
| NO. 1 | BM + 1 μM Compound 1 + 1 μM Y27632 |
| NO. 2 | BM + 1 μM Compound 1 + 3 μM Y27632 |
| NO. 3 | BM + 1 μM Compound 1 + 10 μM Y27632 |
| NO. 4 | BM + 2 μM Compound 1 + 1 μM Y27632 |
| NO. 5 | BM + 2 μM Compound 1 + 3 μM Y27632 |
| NO. 6 | BM + 2 μM Compound 1 + 10 μM Y27632 |
| NO. 7 | BM + 3 μM Compound 1 + 1 μM Y27632 |
| NO. 8 | BM + 3 μM Compound 1 + 3 μM Y27632 |
| NO. 9 | BM + 3 μM Compound 1 + 10 μM Y27632 |
| NO. 10 | BM + 4 μM Compound 1 + 1 μM Y27632 |
| NO. 11 | BM + 4 μM Compound 1 + 3 μM Y27632 |
| NO. 12 | BM + 4 μM Compound 1 + 10 μM Y27632 |
| NO. 13 | BM + 6 μM Compound 1 + 1 μM Y27632 |
| NO. 14 | BM + 6 μM Compound 1 + 3 μM Y27632 |
| NO. 15 | BM + 6 μM Compound 1 + 10 μM Y27632 |
| NO. 16 | BM + 10 μM Compound 1 + 1 μM Y27632 |
| NO. 17 | BM + 10 μM Compound 1 + 3 μM Y27632 |
| NO. 18 | BM + 10 μM Compound 1 + 10 μM Y27632 |

Figure 1F:
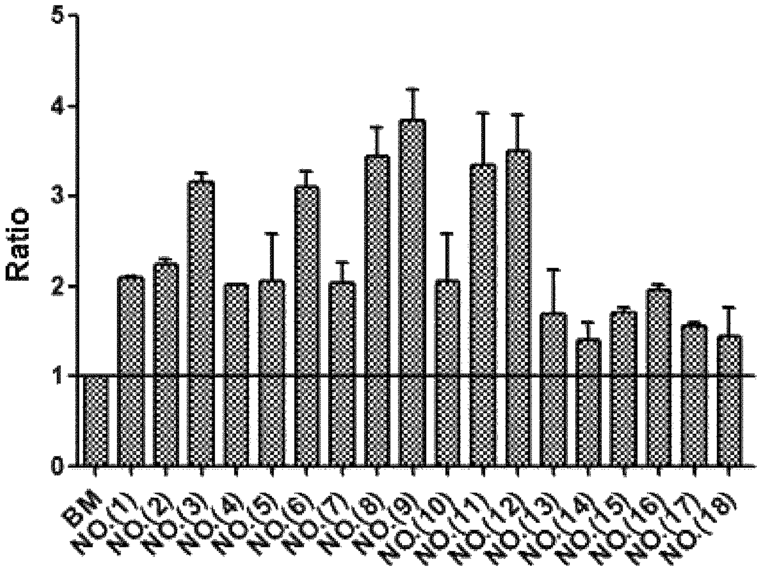
FIG. 1F shows the effect of the culture medium containing the combination of Compound 1 and Y27632 at different concentrations on the proliferation of primary ESCC cells.

The culture mediums with different components were added at a volume of 500 μl/well to 48-well plates which were coated with extracellular matrix gel (Matrigel). ESCC tumor cells (No. 0F0063) isolated from ESCC tissue according to the method described in Example 1 were inoculated in a Matrigel-coated 48-well culture plate at a cell density of $2\times10^4$ cells/$cm^2$. After surface disinfection, the plate was placed in a 37° C., 5% $CO_2$ incubator (purchased from Thermo Fisher), such that equal numbers of freshly isolated ESCC tumor cells (No. 0F0063) were cultured under different medium formulations. The culture mediums were renewed every 4 days after the start of the culture. After 12 days of culture, cell counts were performed. As an experiment control, the basis medium BM was used. The results were shown in FIG. 1F. As shown in the figure, the combinations of different concentrations of Y27632 and Compound 1 have certain synergistic effect on cell proliferation, wherein the concentration combination of 10 μM Y27632 and 3 μM Compound 1 has the most preferable effect.

(3) Effects of Increasing Factors in the Culture Mediums on the Proliferation of Primary ESCC Cells Obtained by the Method of the Invention Extracellular matrix gel (Matrigel®) (purchased from BD Biosciences) was diluted at 1:100 in serum-free DMEM/F12 medium to prepare an extracellular matrix dilution, which was added to a 48-well culture plate with 500 μl/well to completely cover the bottom of the wells of the culture plate. The resultant was let stand for 1 hour in a 37° C. incubator. After 1 hour, the extracellular matrix dilution was removed to provide a Matrigel-coated plate.

Different small molecules, additives and growth factors (Table 5) were sequentially added to the basic medium BM, respectively, so as to prepare culture mediums for ESCC epithelial cells containing different additive components.

TABLE 5

| Preparation of culture mediums containing different components (final concentrations are shown) | |
|---|---|
| Medium NO. | Composition |
| NO. 1 | BM + 3 μM Compound 1 |
| NO. 2 | NO. 1 + 10 μM Y27632 |
| NO. 3 | NO. 2 + 500 nM A83-01 |
| NO. 4 | NO. 3 + 500 nM SB202190 |
| NO. 5 | NO. 4 + 1:50 B27 additive |
| NO. 6 | NO. 5 + 10 ng/mL HGF |
| NO. 7 | NO. 6 + 50 ng/mL EGF |
| NO. 8 | NO. 7 + 1:50 insulin-transferrin-selenium complex stock solution (the stock solution contains 500 μg/ml insulin, 250 μg/ml transferrin, and 250 ng/ml sodium selenite in DMEM/F-12) |
| NO. 9 | NO. 8 + 100 ng/mL Noggin |
| NO. 10 | NO. 9 + 10 ng/mL FGF |
| NO. 11 | NO. 10 + 10 ng/m IGF-1 |
| NO. 12 | NO. 11 + 10 ng/mL FGF10 (purchased from Sino Biological) |
| NO. 13 | NO. 12 + 7 μg/mL bovine pituitary extract (purchased from M&C Gene Technology) |
| NO. 14 | NO. 13 + 0.4 μg/mL hydrocortisone (purchased from Sigma) |
| NO. 15 | NO. 14 + 400 μM non-essential amino acids (purchased from Gibco) |
| NO. 16 | NO. 15 + 1 mM glutamine (purchased from Gibco) |
| NO. 17 | NO. 16 + 10 mM HEPES balanced solution (purchased from Gibco) |
| NO. 18 | NO. 17 + 100 ng/mL RSPO1 (purchased from Sino Biological) |
| NO. 19 | NO. 18 + 5% fetal bovine serum (volume ratio) (purchased from ExCell Bio) |

Figure 2:
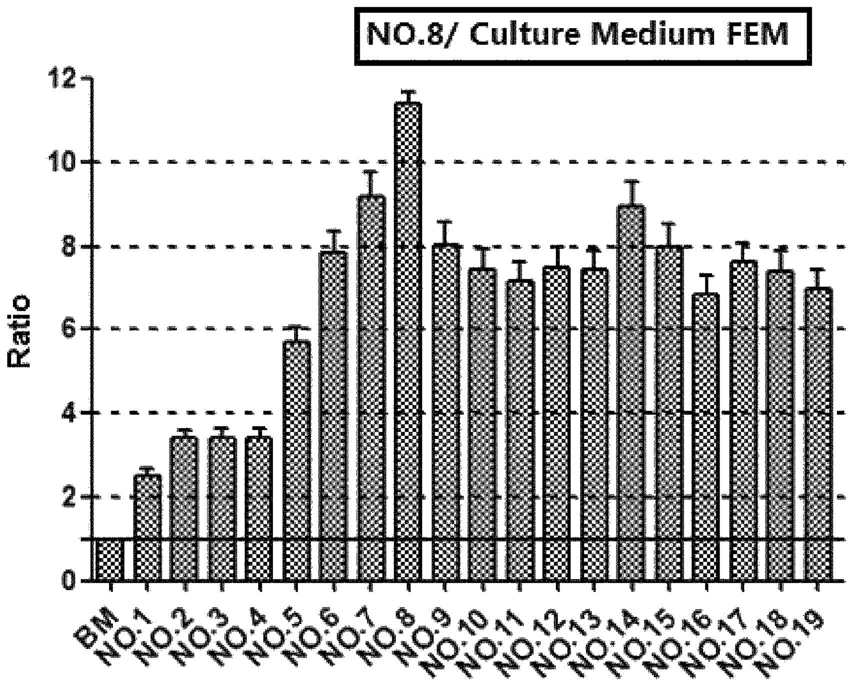
FIG. 2 shows the effect of increasing factors in the culture medium on the proliferation of primary ESCC cells.
Figure 3A:
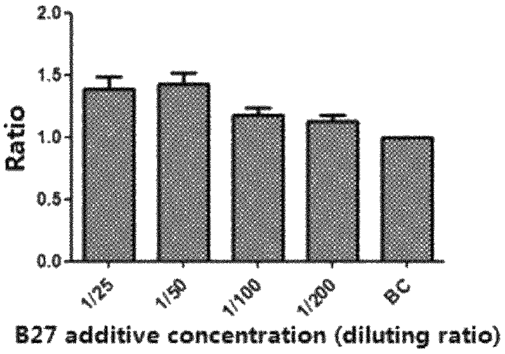
FIGS. 3A-3H show the effect of the concentration of each factor on the proliferation of primary ESCC cells.
Figure 3B:
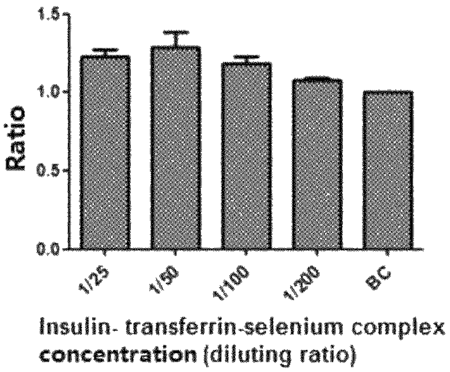
Figure 3C:
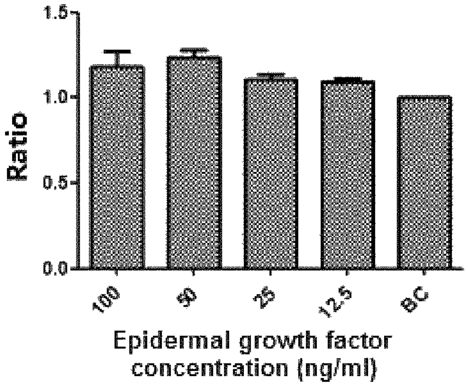
Figure 3D:
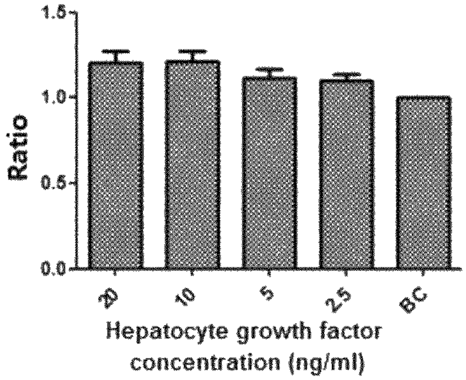
Figure 3E:
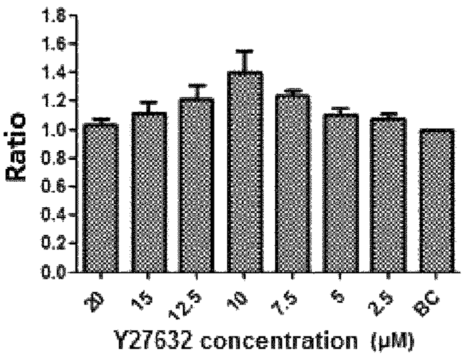
Figure 3F:
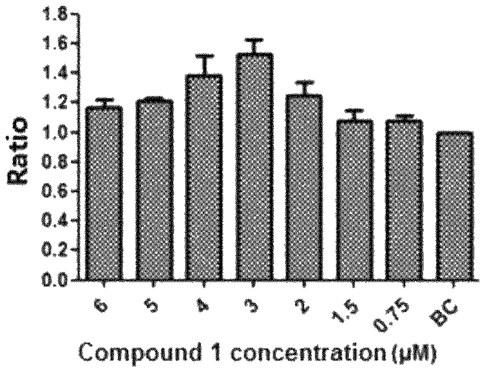
Figure 3G:
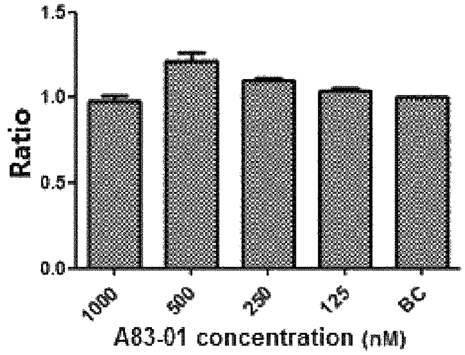
Figure 3H:
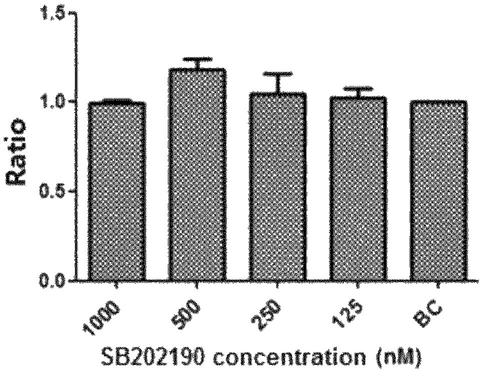
Figure 11C:
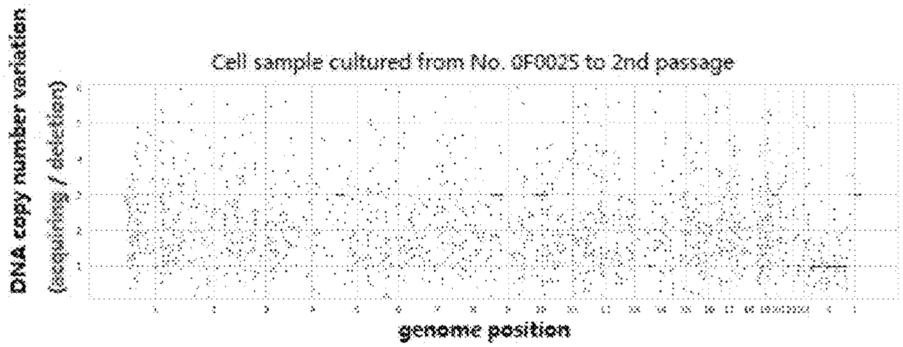
Figure 11D:
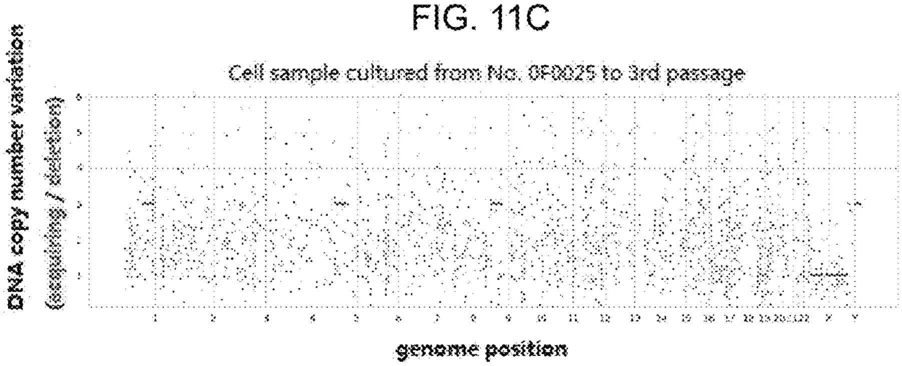

The culture mediums with different components were added at a volume of 500 μl/well to 48-well plates which were coated with extracellular matrix gel (Matrigel), and simultaneously, the BM medium was used as the experiment control. ESCC tumor cells (No. 0F0065) isolated from ESCC tissue according to the method described in Example 1 were inoculated in a Matrigel-coated 48-well culture plate at a cell density of $2\times10^4$ cells/cm$^2$. After surface disinfection, the plate was placed in a 37° C., 5% $CO_2$ incubator (purchased from Thermo Fisher), such that equal numbers of freshly isolated ESCC tumor cells (No. 0F0065) were cultured under different medium formulations. After 10 days of culture, cell counts were performed. The results were shown in FIG. 2. As shown in the figure, it was determined that No. 8 is the most preferred culture medium in this patent for culturing and expanding primary ESCC cells (hereinafter abbreviated as FEM). On this basis, further addition of some factors or small molecule inhibitors did not provide significant effect on promoting the cell proliferation.

(4) Effects of Different Concentrations of the Additive Factors on the Proliferation of Primary ESCC Cells Obtained in the Invention Extracellular matrix gel (Matrigel®) (manufactured by BD Biosciences) was diluted at 1:100 in serum-free DMEM/F12 medium to prepare an extracellular matrix dilution, which was added to a 48-well culture plate with 200 μl/well to completely cover the bottom of the wells of the culture plate. The resultant was let stand for 1 hour in a 37° C. incubator. After 1 hour, the extracellular matrix dilution was removed to provide a Matrigel-coated plate.

Preparation of the culture medium for primary ESCC epithelial cells of the invention (abbreviated as FEM): to the basic medium (BM), was added epidermal growth factor EGF at the final concentration of 50 ng/ml, hepatocyte growth factor HGF at the final concentration of 10 ng/ml, insulin-transferrin-selenium complex (ITS) stock solution at the diluting ratio of 1:50 (insulin at the final concentration of 10 μg/ml, transferrin at the final concentration of 5 μg/ml, and sodium selenite at the final concentration of 5 ng/ml in FEM medium), B27 additive at the diluting ratio of 1:50, Compound 1 at the final concentration of 3 μM, Y27632 at the final concentration of 10 μM, TGFβ1 inhibitor A83-01 at the final concentration of 500 nM, and P38/MAPK inhibitor SB202190 at the final concentration of 500 nM, to prepare the culture medium for primary ESCC epithelial cells.

ESCC epithelial cells originated from cancer tissue were isolated and obtained from the cancer tissue of an ESCC patient (Sample No. 0F0065) using the same method as in Example 1. Next, ESCC tumor cells originated from cancer tissue were counted with a flow imaging counter (JIMBIO FIL, Jiangsu Jimbio Technology Co., Ltd.) to obtain the total number of cells. Then, the cells were inoculated in a Matrigel® (purchased from BD Biosciences)-coated 12-well plate at a density of $4\times10^4$ cells/cm$^2$. 2 mL of the prepared culture medium for primary ESCC epithelial cells FEM was added to the 12-well plate, which was then placed in a 37° C., 5% $CO_2$ incubator (purchased from Thermo Fisher) for culture. When the cells in the culture plate grew to cover about 80% of the bottom area, the medium supernatant in the 12-well plate was discarded and 500 μL 0.05% trypsin (purchased from Gibco) was added for cell digestion; the cells were incubated at 37° C. for 10 minutes until the cells were completely digested as observed under the microscope (EVOS M500, Invitrogen); then the digestion was terminated by using 1 ml of DMEM/F12 culture solution containing 5% (v/v) fetal bovine serum, 100 U/mL penicillin, and 100 μg/mL penicillin; the resultant was collected into a 15 mL centrifuge tube and centrifuged at 1500 rpm for 4 minutes, and then the supernatant was discarded. The centrifuged cell sediments were resuspended in the basic medium BM and were counted with a flow imaging counter (JIMBIO FIL, Jiangsu Jimbio Technology Co., Ltd.) to obtain the total number of cells. The obtained cells were used in the following cultivation experiments.

Next, the following 8 culture mediums with different formulations were prepared for experiments:

Formulation 1: FEM medium composition without B27 additive;

Formulation 2: FEM medium composition without insulin-transferrin-selenium complex;

Formulation 3: FEM medium composition without epidermal growth factor;

Formulation 4: FEM medium composition without hepatocyte growth factor;

Formulation 5: FEM medium composition without Y27632;

Formulation 6: FEM medium composition without Compound 1;

Formulation 7: FEM medium composition without A83-01;

Formulation 8: FEM medium composition without SB202190.

The digested cell suspension was diluted with the above Formulations 1-8 respectively, and were seeded into a 48-well plate with 10,000 cells and 250 μL volume per well.

When using the medium of Formulation 1, to a 48-well plate inoculated with primary cells was added the prepared B27 additive, with 250 μL per well, such that the final concentrations of B27 additive were 1:200, 1:100, 1:50 and 1:25, respectively; the medium of Formulation 1 was used as the control well (BC).

When using the medium of Formulation 2, to a 48-well plate inoculated with primary cells was added the prepared insulin-transferrin-selenium complex, with 250 μL per well, such that the final concentrations of insulin-transferrin-selenium complex stock solution were 1:200, 1:100, 1:50 and 1:25, respectively (corresponding to the final concentrations of insulin/transferrin/sodium selenite of 2.5 μg/ml, 1.25 μg/ml, 1.25 ng/ml; 5 μg/ml, 2.5 μg/ml, 2.5 ng/ml; 10 μg/ml, 5 μg/ml, 5 ng/ml; and 20 μg/ml, 10 μg/ml, 10 ng/ml, respecrtively); the medium of Formulation 2 was used as the control well (BC).

When using the medium of Formulation 3, to a 48-well plate inoculated with primary cells was added the prepared epidermal growth factor, with 250 μL per well, such that the final concentrations of epidermal growth factor were 100 ng/mL, 50 ng/mL, 25 ng/mL, and 12.5 ng/mL, respectively; the medium of Formulation 3 was used as the control well (BC).

When using the medium of Formulation 4, to a 48-well plate inoculated with primary cells was added the prepared hepatocyte growth factor, with 250 μL per well, such that the final concentrations of hepatocyte growth factor were 20 ng/mL, 10 ng/mL, 5 ng/mL, and 2.5 ng/mL, respectively; the medium of Formulation 4 was used as the control well (BC).

When using the medium of Formulation 5, to a 48-well plate inoculated with primary cells was added the prepared Y27632, with 250 μL per well, such that the final concentrations of Y27632 were 20 μM, 15 μM, 12.5 μM, 10 μM, 7.5 μM, 5 μM, and 2.5 μM, respectively; the medium of Formulation 5 was used as the control well (BC).

When using the medium of Formulation 6, to a 48-well plate inoculated with primary cells was added the prepared Compound 1, with 250 μL per well, such that the final concentrations of Compound 1 were 6 μM, 5 μM, 4 μM, 3 μM, 2 μM, 1.5 μM, and 0.75 μM, respectively; the medium of Formulation 6 was used as the control well (BC).

When using the medium of Formulation 7, to a 48-well plate inoculated with primary cells was added the prepared A83-01, with 250 μL per well, such that the final concentrations of A83-01 were 1000 nM, 500 nM, 250 nM, and 125 nM, respectively; the medium of Formulation 7 was used as the control well (BC).

When using the medium of Formulation 8, to a 48-well plate inoculated with primary cells was added the prepared SB202190, with 250 μL per well, such that the final concentrations of SB202190 were 1000 nM, 500 nM, 250 nM, and 125 nM, respectively; the medium of Formulation 8 was used as the control well (BC).

After the cells were expanded to about 85% of the 48 wells, the cells were digested and counted, the ratios were calculated by referring to the cell numbers in the control well (BC), and the results were shown in FIGS. 3A-3H. In each of FIGS. 3A-3H, the ratio represents a ratio of the number of cells of the first passage cultured by using each culture medium to the number of cells of the first passage cultured by the corresponding control well. If the ratio is greater than 1, it indicates that the proliferation promoting effect of the prepared medium containing different concentrations of factors or small molecular compounds is preferable over that of the control well medium; if the ratio is less than 1, it indicates that the proliferation promoting effect of the prepared medium containing different concentrations of factors or small molecular compounds is poorer than that of the control well medium.

According to the results of FIGS. 3A-3H, the volume concentration of B27 additive in the culture medium is preferably 1:25-1:200, more preferably 1:25-1:50; the volume concentration of insulin-transferrin-selenium complex is preferably 1:25-1:200, more preferably 1:25-1:100 (corresponding to the final concentrations of insulin/transferrin/sodium selenite of 2.5-20 μg/ml, 1.25-10 μg/ml, 1.25-10 ng/ml, respectively, and more preferably 5-20 μg/ml, 2.5-10 μg/ml, 2.5-10 ng/ml, respectively); the amount of epidermal growth factor is preferably 12.5 ng/ml-100 ng/ml, more preferably 50 ng/ml-100 ng/ml; the amount of hepatocyte growth factor is preferably 2.5 ng/ml-20 ng/ml, more preferably 10 ng/ml-20 ng/ml; the amount of Y27632 is preferably 2.5 μM-15 μM, and more preferably 7.5 μM-12.5 μM; the amount of Compound 1 is preferably 0.75 μM-6 μM, and more preferably 2 μM-6 μM; the amount of A83-01 is preferably 125 nM-500 nM, and more preferably 250 nM-500 nM; the amount of SB202190 is preferably 125 nM-500 nM, and more preferably 250 nM-500 nM.

Example 3

Culture of Human Primary ESCC Epithelial Cells (1) Culture of Primary ESCC Tumor Cells Derived from ESCC Tissue ESCC epithelial cells originated from cancer tissue were isolated and obtained from the cancer tissue of an ESCC patient (Sample No. 0F0062) using the same method as in Example 1. Next, ESCC tumor cells orginated from cancer tissue were counted with a flow imaging counter (JIMBIO FIL, Jiangsu Jimbio Technology Co., Ltd.) to obtain the total number of cells. Then, the cells were inoculated in a Matrigel® (purchased from BD Biosciences)-coated 12-well plate at a density of $4\times10^4$ cells/cm$^2$. 2 mL of the prepared culture medium for primary ESCC epithelial cells FEM was added to the 12-well plate, which was then placed in a 37° C., 5% $CO_2$ incubator (purchased from Thermo Fisher) for culture.

FIG. 4A is a microscopy image (photographed by a 40× inverted phase contrast microscope) of the cells which were cultured to day 4 after inoculation at a density of $4\times10^4$ cells/cm$^2$ into a Matrigel-coated 12-well plate according to this Example. Microscopic observation shows that the cultured primary ESCC tumor cells derived from the cancer tissue were of high purity and did not contain fibroblasts. FIG. 4B is a microscopy image (photographed by a 40× inverted phase contrast microscope) of the cells which were cultured to day 12 after inoculation according to this Example. It can be seen from FIGS. 4A and 4B that the formation of obvious clone can be seen under microscope when the primary ESCC cells isolated were cultured in vitro for 4 days, and the number of cells was significantly expanded after 12 days of expansion, suggesting that the technology of the invention is a efficient technology for expanding ESCC epithelial cells in vitro.

(2) Comparison of the Culture Results of Primary ESCC Tumor Cells Derived from ESCC Tissue Under the Conditions of with and without Coating of Extracellular Matrix Gel The primary ESCC tumor cells (No. 0F0065) derived from cancer tissues were isolated from the cancer tissues of one ESCC patient, using the same method of Example 1. Next, equal numbers ($4\times10^4$ cells/cm$^2$) of the primary ESCC tumor cells 0F0065 were inoculated into a Matrigel® (purchased from BD Biosciences)-coated 12-well plate and a 12-well plate without any treatment, respectively. 2 mL of the prepared culture medium for primary ESCC epithelial cells FEM was added to the 12-well plates, which were then placed in a 37° C., 5% $CO_2$ incubator (purchased from Thermo Fisher) for culture after disinfection. FIGS. 5A and 5B are microscopy images (photographed by a 100× inverted phase contrast microscope) of the ESCC tissue-derived primary ESCC tumor cells 0F0065 which were cultured to day 11 under the conditions of Matrigel-coated and without Matrigel-coated, respectively. It can be seen from the figures that the cell density and the number of cells in FIG. 5A (Matrigel-coated) are higher than those in FIG. 5B (without Matrigel-coated). At the same time, there are a small number of aging cells (cells with bigger cell bodies) shown in FIG. 5B, while there is no cell aging in FIG. 5A. Therefore, it can be confirmed that the Matrigel-coated culture plate is more favorable for the proliferation of ESCC tumor cells than the culture plate without any treatment.

Example 4

Effect of Different Culture Mediums on Promoting Proliferation of ESCC Tissue-Derived Primary ESCC Tumor Cells (1) Comparison of the Influences of Different Culture Mediums on Clone Formation of Primary Cells and Proliferation Effects of Primary Cells Culture medium for primary ESCC epithelial cell FEM was prepared in the same method of Example 2, and basic medium BM was prepared as control. As another control, a culture medium for cell conditional reprogramming technology FM was prepared additionally. For the preparation steps, please refer to Liu et al., Nat Protoc., 12(2): 439-451, 2017. The formulation of the culture medium is shown in Table 6. Simultaneously, as a further control, a culture medium for primary esophageal carcinoma cells KM was prepared. For the preparation steps, see Karin J. Purdie et al., Cancer Cell Culture: Methods and Protocols, Second Edition, Methods in Molecular Biology, vol. 731, 151-159, 2011. The formulation of the culture medium is shown in Table 7. Moreover, as an additional control, a commercial medium EpiCult™ Plus Medium (hereinafter also referred to as "EPI medium") was purchased from Stemcell, and the formulation of the culture medium is shown in Table 8.

TABLE 6

Composition of culture medium for cell conditional reprogramming technology FM

| Medium composition | Supplier | Final concentration |
|---|---|---|
| DMEM medium | Corning | 65 vol. % |
| Fetal bovine serum | Gibico | 10 vol. % |
| Ham's F12 Nutrient Mixture | Gibico | 25 vol. % |
| Hydrocortisone | Sigma-Aldrich | 25 ng/ml |
| Epidermal growth factor | R&D | 0.125 ng/ml |
| Insulin | Sigma-Aldrich | 5 μg/ml |
| Amphotericin B | Sigma-Aldrich | 250 ng/ml |
| Gentamicin | Gibico | 10 μg/ml |
| Cholera Toxin | Sigma-Aldrich | 0.1 nM |
| Y27632 | Enzo | 10 μM |

TABLE 7

Composition of culture medium KM (Keratinocyte medium)

| Medium composition | Supplier | Final concentration |
|---|---|---|
| Epidermal growth factor | Sino Biological | 10 ng/ml |
| Liothyronine Triiodothyronin | MCE | 13 ng/ml |
| Transferrin | Sino Biological | 5 μg/ml |
| Cholera Toxin | Sigma-Aldrich | 8.4 ng/ml |
| Hydrocortisone | Sigma-Aldrich | 0.4 μg/ml |
| Insulin | Sigma-Aldrich | 5 μg/ml |
| Fetal bovine serum | Gibico | 10 vol. % |

TABLE 7-continued

Composition of culture medium KM (Keratinocyte medium)

| Medium composition | Supplier | Final concentration |
|---|---|---|
| DMEM medium | Corning | 65 vol. % |
| Ham's F12 Nutrient Mixture | Gibico | 25 vol. % |

TABLE 8

Composition of commercial medium EpiCult ™ Plus Medium (EPI)

| Medium composition | Supplier | Final concentration |
|---|---|---|
| EpiCult ™ Plus Basal Medium | Stemcell | 98 vol. % |
| EpiCult ™ Plus Supplement | Stemcell | 2 vol. % |
| Hydrocortisone | Stemcell | 480 ng/ml |

By using the same method of Example 1, the primary ESCC tumor cells (No. 0F0060) derived from ESCC tissues were obtained. Next, the cells were cultured at the same density ($4\times10^4$ cells/$cm^2$) under the following five culture conditions:

A. The technology of the invention: the primary ESCC tumor cells were inoculated into a 24-well plate coated with Matrigel® (manufactured by BD Biosciences) at a density of $4\times10^4$ cells/$cm^2$, cultured using 2 mL of the culture medium for primary ESCC epithelial cells FEM of the invention;

B. Cell conditional reprogramming technology: the primary ESCC tumor cells were inoculated onto γ-ray irradiated mouse fibroblast cell line J2 cells (purchased from Kerafast) at a density of $4\times10^4$ cells/$cm^2$, cultured in a 24-well plate using the cell conditional reprogramming medium FM (the detailed steps, see Liu et al., Am J Pathol, 183(6): 1862-1870, 2013);

C. The primary ESCC tumor cells were inoculated into a Matrigel® (manufactured by BD Biosciences)-coated 24-well plate at a density of $4\times10^4$ cells/$cm^2$, and cultured in the 24-well plate using 2 mL of the culture medium KM;

D. The primary ESCC tumor cells were inoculated into a Matrigel® (manufactured by BD Biosciences)-coated 24-well plate at a density of $4\times10^4$ cells/$cm^2$, and cultured in the 24-well plate using 2 mL of the commercial medium EPI;

E. The primary ESCC tumor cells were inoculated into a Matrigel® (manufactured by BD Biosciences)-coated 24-well plate at a density of $4\times10^4$ cells/$cm^2$, and cultured in the 24-well plate using 2 mL of the basic medium BM.

In the above five cultures, the cells cultured under the five culture conditions wherein the mediums were renewed every 4 days. At the same time, the cell clone formation and the cell proliferation status under the cultivation of each medium in the 24-well plate was observed, and the cell growth status was recorded by taking pictures with a microscope (EVOS M500, Invitrogen).

To the primary ESCC cancer cells (No. 0F0060) cultured with the technology of the invention, when the cells in the culture plate grew to cover about 80% of the bottom area, the medium supernatant in the 24-well plate was discarded and 500 μL 0.05% trypsin (purchased from Gibco) was added for cell digestion; the cells were incubated at 37° C. for 10 minutes until the cells were completely digested as observed under the microscope (EVOS M500, Invitrogen); then the digestion was terminated by using 1 ml of DMEM/F12 culture solution containing 5% (v/v) fetal bovine serum, 100 U/mL penicillin, and 100 μg/mL penicillin; the resultant was collected into a 15 mL centrifuge tube and centrifuged at 1500 rpm for 4 minutes, and then the supernatant was discarded. The centrifuged cell sediments were resuspended in the culture medium of the invention and were counted with a flow imaging counter (JIMBIO FIL, Jiangsu Jimbio Technology Co., Ltd.) to obtain the total number of cells, which was 364,000. The cells cultured under the other four culture conditions were digested and counted in the same operation process as above. The total number of cells cultured by using the mediums FM, KM, EPI and BM were 315000, 91000, 98000 and 84000, respectively.

The photos of cells in FIGS. 6A-6E are the microscopic photos (under a 40× inverted phase contrast microscope) of the Sample No. 0F0060 which were cultured to day 14 under five different culture conditions: wherein FIG. 6A is the microscopic photo of 0F0060 cultured to day 14 using the basic medium BM; FIG. 6B is the microscopic photo of 0F0060 cultured to day 14 using the culture medium FEM of the invention; FIG. 6C is the microscopic photo of 0F0060 cultured to day 14 using the culture medium KM; FIG. 6D is the microscopic photo of 0F0060 cultured to day 14 using the commercial medium EPI; and FIG. 6E is the microscopic photo of 0F0060 cultured to day 14 using the cell conditional reprogramming medium FM. It can be seen from the figures that Sample 0F0060 could not form cell clones after 14 days of culture with basic medium BM (6A); the cultivation under the culture mediums KM (6C) and EPI (6D) for 14 days only formed a few cell clones, with poor cell status; the cells cultured with conditional reprogramming medium FM (6E) for 14 days expanded to a certain extent, but the cell density and the cell number were not comparable with those obtained with the culture medium FEM of the invention.

FIG. 7 is a comparative diagram of cell proliferation effects obtained by culturing the primary ESCC cells isolated from six ESCC patient samples (No. 0F0056, 0F0060, 0F0061, 0F0062, 0F0071, 0F0075) according to Example 1 for 16 days under the conditions of five different culture mediums, where ✓ represents a moderate clone formation ability and proliferation promoting effect, ✓✓ represents a significant clone formation ability and proliferation promoting effect, × represents no clone formation, and NT represents not tested. It can be confirmed from the figure that the culture medium of the invention has significant superiority over the other four culture conditions in terms of clone formation ability and cell proliferation promoting effect in cultivation of the ESCC tissue originated primary cell.

(2) Continuous Cultivation and Growth Curve of Primary ESCC Tumor Cells in Different Culture Mediums The culture medium for primary ESCC epithelial cell FEM and the culture mediums BM, KM, FM, and EPI as controls were obtained by using the same method as in (1) of this Example.

The ESCC tissue originated primary ESCC tumor cells (No. 0F0075) were cultured in the following five culture mediums, and then digested, passaged and counted by using the same method as in (1) of this Example.

When the passaged cells grew in the culture plate to cover about 80% of the bottom area of the plate again, the cultured cells were digested, collected and counted according to the above operating method. The cells were inoculated at a density of $4\times10^4$ cells/well again and cultured continuously.

The following is the formula for calculating the cell population doubling number of primary ESCC epithelial cells under different culture conditions:

Population Doubling (PD)=$3.32*\log_{10}$ (total number of digested cells/the number of cells at initial inoculation), see Chapman et al., Stem Cell Research & Therapy 2014, 5: 60.

FIG. 8 shows the growth curves of 0F0075 cells under five different culture conditions drawn by Graphpad Prism software. The abscissa represents the days of cell culture, and the ordinate represents the multiple of cumulative cell proliferation, i.e., the multiple of cell expansion in the culture period. The larger the value, the more multiples the cell expands in certain period, that is, the more cells are expanded. The slope represents the rate of cell expansion. It can be confirmed from the figure that the proliferation rate of ESCC epithelial cells cultured with the culture medium FEM of the invention was superior to the other four culture conditions, and it can also be confirmed that the technology of the invention can continuously culture the primary ESCC epithelial cells, and the expansion rate remained unchanged after 30 days of amplification.

The photos of cells in FIGS. 9A and 9C are microscopic photos (under a 40× inverted phase contrast microscope) of 0F0075 cultured to the first passage under FEM and EPI culture conditions, respectively. The photos of cells in FIGS. 9B and 9D are microscopic photos (under a 40× inverted phase contrast microscope) of 0F0075 cultured to the ninth passage under FEM and EPI culture conditions, respectively. It can be confirmed from the figures that the technology of the invention can continuously culture the primary ESCC epithelial cells, and the morphology of cells after multiple passages and continuous culture did not change significantly compared with that before passage. However, when the cells were cultured with commercial medium EPI to the 9th passage, the morphology of cells had changed significantly, which could not meet the requirement of continuous culture for primary ESCC epithelial cells.

Example 5

Identification of Primary ESCC Tumor Cells Derived from Cancer Tissues (1) Immunohistochemical Identification of Primary ESCC Tissues and ESCC Cells after Passage Culture Cancer tissue (Sample No. 0F0053) about the size of a mung bean was taken from a surgical resection sample of an ESCC patient, and immersed in 1 mL of 4% paraformaldehyde. ESCC epithelial cells (Sample No. 0F0053) were obtained from the remaining cancer tissue in the same method of Example 1. Sample 0F0053 was continuously cultured to the sixth passage using the culture medium FEM of the invention according to the method of Example 3.

Immunohistochemistry assay was used to detect the expression of important ESCC-related biomarkers in the original tissue of Sample 0F0053 and the primary cells obtained by continuous culture to the sixth passage. The tissue was fixed with 4% paraformaldehyde, embedded in paraffin, and cut into tissue sections of 4 μm thickness with a microtome. Routine immunohistochemical detection was then performed (for detailed steps, see Li et al., Nature Communication, (2018) 9: 2983). The primary antibodies used were Cytokeratin (CK) (purchased from CST), p63 antibody (purchased from CST), p53 antibody (purchased from CST), and Ki67 antibody (purchased from R&D).

FIGS. 10A and 10B confirm that the expression of ESCC-related biomarkers on the cells that were cultured from the ESCC tumor cells (Sample No. 0F0053) by the technology of the invention to the 6th passage, was consistent with the expression of markers on the original tissue section from which the cells were derived. This suggests that the cells cultured by the technology of the invention maintain the original pathological characteristics of the cancer tissues of the ESCC patients.

(2) Copy Number Variation Analysis of ESCC Tissues and ESCC Cells Digested and Cultured from Cancer Tissues The ESCC tumor cells (No. 0F0025) were continuously cultured using the culture medium FEM of the invention according to the method of Example 3. For the ESCC tumor cells that were cultured and passaged in vitro for the first, second and third times (P1, P2 and P3, respectively) and the cancer tissues directly obtained from ESCC patients by surgery, the genomic DNA of the cells was extracted using the DNeasy blood & tissue Kit (manufactured by QIAGEN). Normal esophageal tissues from the same patient were collected, and the genomic DNA was extracted by the same method, which was used as background control. Next, whole exome sequencing was performed on the genomic DNA of cells and tissue samples (see Hans Clevers et al., Cell, 11; 172 (1-2): 373-386, 2018 for specific operation steps), and the sequencing results were compared with the reference genome. CNVkit software was used to analyze the comparison results. CBS segmentation (circular binary segmentation algorithm) was used to analyze the gene copy number of the whole genome, features of regions with similar position and copy number changes were extracted by rolling median software, and the results were plotted according to the chromosome order. It is confirmed from FIGS. 11A-11D that the copy number variation in the cancer tissue-originated ESCC tumor cells, which were cultured by the technology of the invention, was substantially consistent with that in the original cancer tissue of the patient.

Example 6

Effects of Removing Single Factor or Combination of Factors from Culture Medium on Continuous Expansion of Primary ESCC Cells The culture medium for primary ESCC epithelial cell FEM was prepared in the same method of Example 2. As a control, a basic medium (hereinafter also referred to as "BM") was prepared using the same method of Example 2. In addition, six other different culture mediums were prepared according to Table 9.

TABLE 9

Culture mediums with different compositions (final concentrations are shown)

| Culture medium | Composition |
|---|---|
| FEM without Compound 1 | DMEM/F12 + 100 μg/mL Primocin + 1:50 B27 additive + 50 ng/ml EGF + 10 ng/ml HGF + 1/50 diluting ratio ITS complex + 10 μM Y27632 + 500 nM A83-01 + 500 nM SB202190 |
| FEM without Y27632 | DMEM/F12 + 100 μg/mL Primocin + 1:50 B27 additive + 50 ng/ml EGF + 10 ng/ml HGF + 1/50 diluting ratio ITS complex + 3 μM Compound 1 + 500 nM A83-01 + 500 nM SB202190 |
| FEM without Compound 1 and Y27632 | DMEM/F12 + 100 μg/mL Primocin + 1:50 B27 additive + 50 ng/ml EGF + 10 ng/ml HGF + 1/50 diluting ratio ITS complex + 500 nM A83-01 + 500 nM SB202190 |
| FEM without A83-01 | DMEM/F12 + 100 μg/mL Primocin + 1:50 B27 additive + 50 ng/ml EGF + 10 ng/ml HGF + 1/50 diluting ratio ITS complex + 3 μM Compound 1 + 10 μM Y27632 + 500 nM SB202190 |
| FEM without SB202190 | DMEM/F12 + 100 μg/mL Primocin + 1:50 B27 additive + 50 ng/ml EGF + 10 ng/ml HGF + 1/50 diluting ratio ITS complex + 3 μM Compound 1 + 10 μM Y27632 + 500 nM A83-01 |
| FEM without A83-01 and SB202190 | DMEM/F12 + 100 μg/mL Primocin + 1:50 B27 additive + 50 ng/ml EGF + 10 ng/ml HGF + 1/50 diluting ratio ITS complex + 3 μM Compound 1 + 10 μM Y27632 |

ESCC tissue-originated primary ESCC tumor cells (No. 0F0061) were obtained by using the same method as in Example 1. Then, the primary ESCC tumor cells were inoculated in a Matrigel® (manufactured by BD Biosciences)-coated 24-well plate at a density of $4\times10^4$ cells/$cm^2$. 1 mL of the culture medium for primary ESCC epithelial cells (FEM) of the invention was used, which was then placed in a 37° C., 5% $CO_2$ incubator (purchased from Thermo Fisher) for culture.

When the cells in the culture plate grew to cover about 80% of the bottom area, the medium supernatant in the 24-well plate was discarded and 400 μL 0.05% trypsin (purchased from Gibco) was added for cell digestion; the cells were incubated at 37° C. for 10 minutes until the cells were completely digested as observed under the microscope (EVOS M500, Invitrogen); then the digestion was terminated by using 800 μL of DMEM/F12 culture solution containing 5% (v/v) fetal bovine serum, 100 U/mL penicillin, and 100 μg/mL penicillin; the resultant was collected into a 15 mL centrifuge tube and centrifuged at 1500 rpm for 4 minutes, and then the supernatant was discarded. The centrifuged cell sediments were resuspended in the culture medium of the invention and were counted with a flow imaging counter (JIMBIO FIL, Jiangsu Jimbio Technology Co., Ltd.) to obtain the total number of cells. The cells were incubated into another 24-well culture plate coated with extracellular matrix gel at a density of $2\times10^4$ cells/$cm^2$ for further culture. The cells were inoculated into the 24-well culture plate coated with extracellular matrix gel at the same density using other seven different mediums for culture.

When the passaged cells grew in the culture plate to cover about 80% of the bottom area of the plate again, the cultured cells were digested, collected and counted according to the above operating method. The cells were inoculated at a density of $2\times10^4$ cells/$cm^2$ again and cultured continuously using the respective culture mediums of different compositions.

The following is the formula for calculating the cell population doubling number of primary ESCC epithelial cells under different culture conditions:

Population Doubling (PD)=3.32*$\log_{10}$ (total number of digested cells/the number of cells at initial inoculation), see Chapman et al., Stem Cell Research & Therapy 2014, 5: 60.

Figure 12:
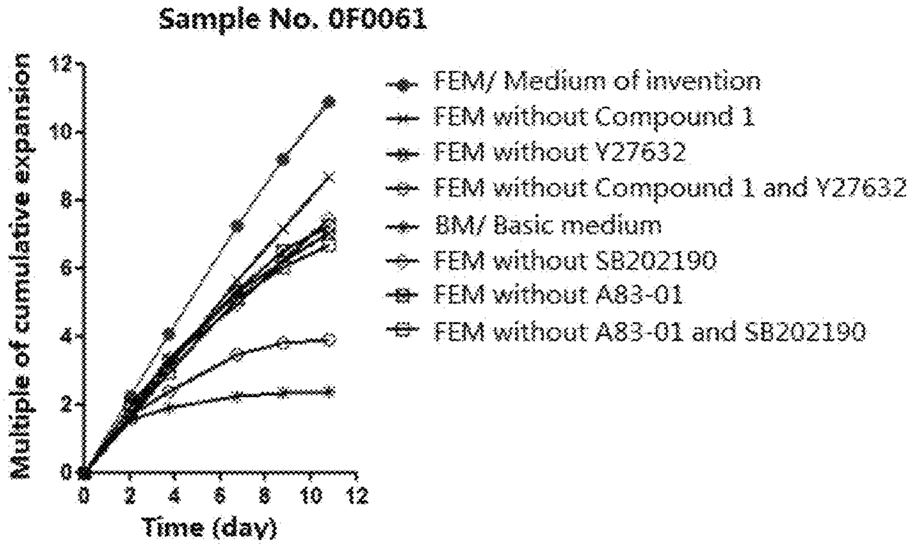
FIG. 12 is a comparative diagram of cell growth curves obtained by culturing the cells isolated from one clinical ESCC tissue sample (No. 0F0061), under the conditions of the culture medium FEM of the invention and the culture mediums obtained by subtracting different components, respectively.

FIG. 12 shows the growth curves of cells under eight different culture conditions drawn by Graphpad Prism software. The abscissa represents the days of cell culture, and the ordinate represents the multiple of cumulative cell proliferation, i.e., the multiple of cell expansion in the culture period. The larger the value, the more multiples the cell expands in certain period, that is, the more cells are expanded. The slope represents the rate of cell expansion.

The photos of cells in FIGS. 13A-13H are microscopic photos (under a 100× inverted phase contrast microscope) of 0F0061 cultured to the third passage under the above eight different culture conditions.

As can be seen from the results of FIG. 12 and FIG. 13, the proliferation effect of cells was significantly attenuated after the removal of Compound 1, Y27632, A83-01 or SB202190 alone, or the combination of Compound 1 and Y27632, or the combination of A83-01 and SB202190 from the culture medium of the invention. Among others, after removing the combined components of Compound 1 and Y27632, the proliferation rate of cells was significantly reduced, suggesting that the combined components of Compound 1 and Y27632 in the culture medium of the invention are necessary for cell proliferation and continuous culture.

Example 7

Xenograft Tumorigenesis Experiments of Cancer Tissue-Derived Primary ESCC Tumor Cells in Mice ESCC tumor cells (No. 0F0056) were isolated and obtained from the cancer tissues of one pathologically diagnosed ESCC patient by using the same method as in Example 1. 0F0065 was cultured using the culture medium FEM of the invention according to the method of Example 3, and when the number of ESCC tumor cells reached $1\times10^7$, the ESCC tumor cells were digested and collected by using the same method of Example 4. The culture medium for ESCC tumor cells of the invention FEM and Matrigel® (purchased from BD Biosciences) were mixed at a ratio of 1:1, and 100 μL of the culture medium mixed with Matrigel was used to resuspend $5\times10^6$ ESCC tumor cells, and the resultant was injected into the ESCC fat pad and the axilla of the right forelimb of 6-week-old female highly immunodeficient mice (NCG) (purchased from Nanjing Model Animal Research Center), respectively. The volume and growth rate of tumors in mice generated from the ESCC tumor cells were observed and photographed every three days.

Tumor formation can be observed in both of the two tumor cell inoculation sites of the mice on day 15 after tumor cell inoculation. From day 15 to day 30, the tumor proliferation in mice was obvious. This indicates that the cancer tissue-derived ESCC tumor cells cultured by the culture method of the invention have tumorigenicity in mice.

Example 8

Drug Sensitivity Functional Test of Cancer Tissue-Derived EACC Tumor Cells

Taking a surgical resection sample from an ESCC patient as an example, it is verified that the ESCC tumor cells cultured from the patient-derived ESCC tumor samples can be used to test the sensitivity of the tumor cells of the patient to different drugs.

1. Plating of primary ESCC tumor cells: Cell suspensions of isolated ESCC tumor cells (No. 0F0060 and No. 0F0062) obtained according to the method of Example 1, were inoculated in a Matrigel® (purchased from BD Biosciences)-coated 12-well plate at a density of $4\times10^4$ cells/$cm^2$. 2 mL of the prepared culture medium for primary ESCC epithelial cells FEM was added to the 12-well plate, which was then placed in a 37° C., 5% $CO_2$ incubator (purchased from Thermo Fisher) for culture. When the cells in the culture plate grew to cover about 80% of the bottom area, the medium supernatant in the 12-well plate was discarded and 500 μL 0.05% trypsin (purchased from Gibco) was added for cell digestion; the cells were incubated at 37° C. for 10 minutes until the cells were completely digested as observed under the microscope (EVOS M500, Invitrogen); then the digestion was terminated by using 1 mL of DMEM/F12 culture solution containing 5% (v/v) fetal bovine serum, 100 U/mL penicillin, and 100 μg/mL penicillin; the resultant was collected into a 15 mL centrifuge tube and centrifuged at 1500 rpm for 4 minutes, and then the supernatant was discarded. The centrifuged cell sediments were resuspended in the culture medium FEM and were counted with a flow imaging counter (JIMBIO FIL, Jiangsu Jimbio Technology Co., Ltd.) to obtain the total number of cells, which were 830,000 and 768,000, respectively. The cells were incubated into a 384-well plate at a density of 2,000-4,000 cells/well, and the cells were adhered overnight.
2. Drug Gradient Experiments:
   (1) The drug storage plates were prepared by gradient dilution method: 10 μL of the drug stock solutions to be tested (the concentration of the drug stock solution was determined based on 2 times of the maximum blood concentration Cmax of the drug in the human body) were respectively taken, and added to 0.5 mL EP tubes containing 20 μL of DMSO; 10 μL of solutions from the above EP tubes were pipetted into second 0.5 mL EP tubes loaded with 20 μL of DMSO, that is, diluting the drugs in a ratio of 1:3. The above method was repeated for gradually dilution and 7 concentrations required for dosing were obtained. Different concentrations of drugs were added to the 384-well drug storage plates. Equal volume of DMSO was added to each well of the solvent control group as a control. In this example, the drugs to be tested were Bortezomib (purchased from MCE), Mitomycin (purchased from MCE), Hydroxycamptothecin (purchased from MCE), and Erlotinib (purchased from MCE).
   (2) Using a high-throughput automated workstation (JANUS, Perkin Elmer), different concentrations of drugs and solvent controls in the 384-well drug storage plates were added to 384-well cell culture plates plated with the ESCC tumor cells. The drug groups and the solvent control groups were each arranged with 3 duplicate wells. The volume of drugs added to each well was 100 nL.
   (3) Test of cell viability: 72 hours after administration, Cell Titer-Glo assay kit (purchased from Promega) was used to detect the chemiluminescence value of the cultured cells after drug administration. The magnitude of the chemiluminescence value reflects the cell viability and the effect of the drug on the cell viability. 10 μL of the prepared Cell Titer-Glo detection solution was added to each well, and a microplate reader (Envision, Perkin Elmer) was used to detect the chemiluminescence value after mixing.
   (4) Test of cell viability: According to the formula, Cell survival rate (%)=Chemiluminescence value of drug well/Chemiluminescence value of control well*100%, the cell survival rates of cells treated with different drugs were calculated. Graphs were made by using Graphpad Prism software and the half-inhibition rates $IC_{50}$ were calculated.
   (5) The drug sensitivity testing results were shown in FIG. 14.

Figure 14A:
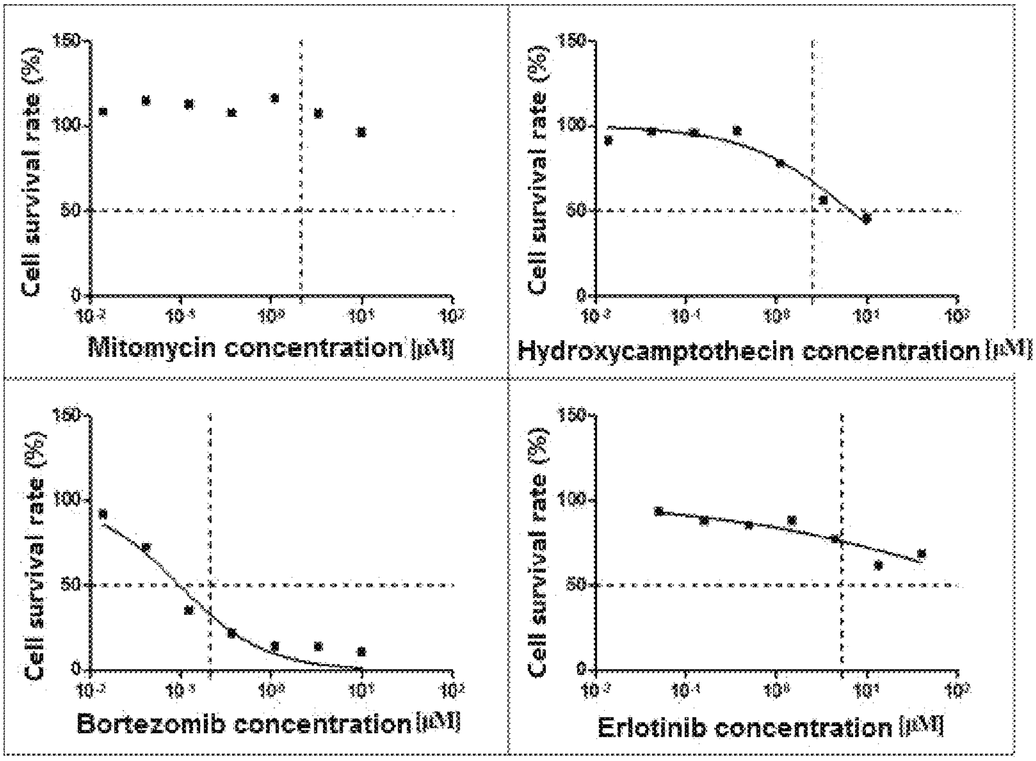
FIGS. 14A and 14B show the dose-response curves of primary ESCC tumor cells on different chemotherapeutic drugs and targeted drugs, wherein the primary ESCC tumor cells were obtained by culturing the surgically resected cancer tissue samples of two different ESCC patients (No. 0F0060 and No. 0F0062) with the culture medium FEM of the invention, respectively.
Figure 14B:
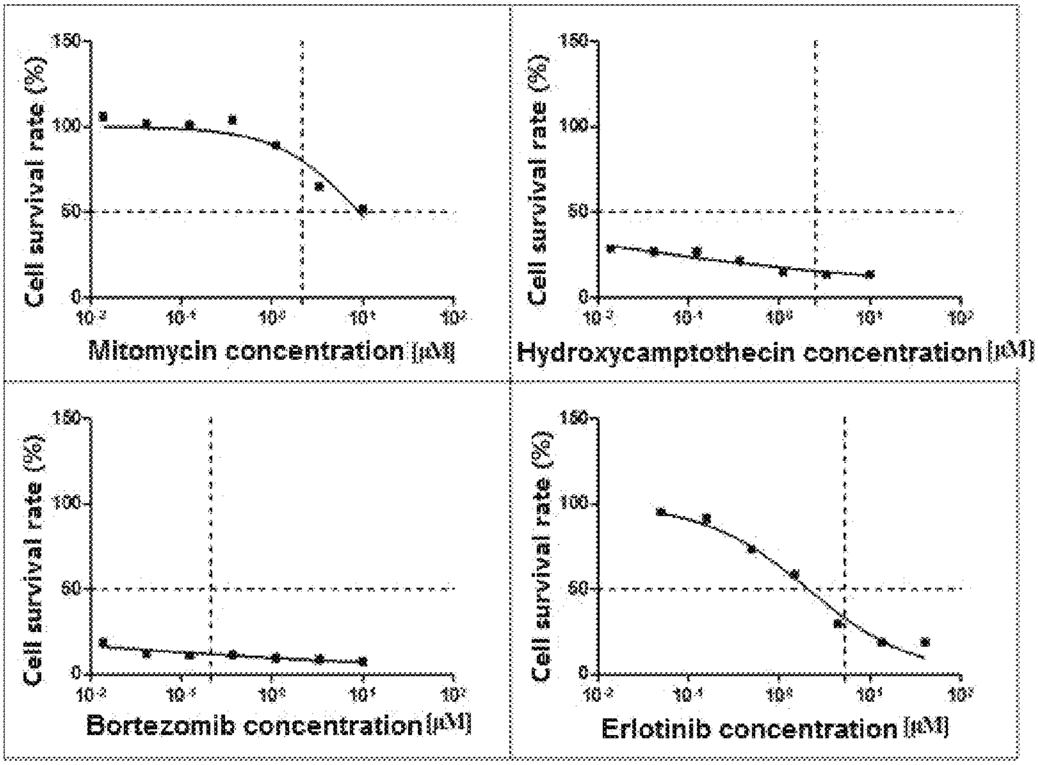

FIGS. 14A and 14B respectively represent the sensitivity of the ESCC tumor cells cultured from surgically resected cancer tissue samples of two different ESCC patients (Sample No. 0F0060 and Sample No. 0F0062) to two chemotherapeutic drugs Mitomycin and Hydroxycamptothecin, and to targeted drugs Bortezomib and Erlotinib. Specifically, FIG. 14A shows the sensitivity results of ESCC cells cultured from Sample No. 0F0060 on four drugs; FIG. 14B shows the sensitivity results of ESCC cells cultured from Sample No. 0F0062 on four drugs. The results show that the cells from the same patient have different sensitivities to different drugs, and the cells from different patients also have different sensitivities to the same drug.

INDUSTRIAL APPLICABILITY

The invention provides a culture medium and a culture method for culturing or expanding primary ESCC epithelial cells in vitro. The cultured cells can be used in the efficacy evaluation and screening of drug. Therefore, the invention is applicable in the industry.

Although the present invention has been described in details herein, the present invention is not limited thereto, and those skilled in the art can make modification according to the principle of the invention. Therefore, all modifications made according to the principle of the invention should be interpreted as falling within the protection scope of the invention.

The invention claimed is:

1. A primary cell culture medium for culturing primary esophageal squamous cell carcinoma (ESCC) epithelial cells, comprising a MST1/2 kinase inhibitor; a ROCK inhibitor; epidermal growth factor; insulin-transferrin-selenium complex; hepatocyte growth factor; a TGFβ type I receptor inhibitor selected from at least one of A83-01, SB431542, Repsox, SB505124, SB525334, SD208, LY36494, and SJN2511; and a P38/MAPK inhibitor selected from at least one of SB202190, SB203580, VX-702, VX-745, PD169316, RO4402247, and BIRB796;

wherein the MST1/2 kinase inhibitor comprises a compound of Formula (I) or a pharmaceutically acceptable salt, or a solvate thereof, and the ROCK inhibitor is at least one selected from the group consisting of Y27632, Fasudil, and H-1152, Formula (I)

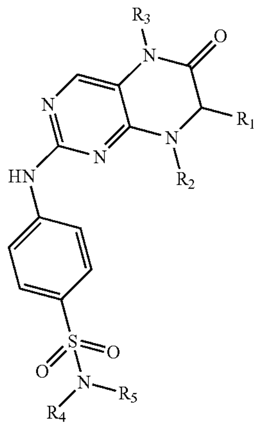

wherein, $R_1$ is selected from C1-C6 alkyl, C3-C6 cycloalkyl, C4-C8 cycloalkylalkyl, C2-C6 spirocycloalkyl, and aryl optionally independently substituted with 1-2 $R_6$, aryl C1-C6 alkyl optionally independently substituted with 1-2 $R_6$ and heteroaryl optionally independently substituted with 1-2 $R_6$;

$R_2$ and $R_3$ are each independently selected from C1-C6 alkyl;

$R_4$ and $R_5$ are each independently selected from hydrogen, C1-C6 alkyl, C3-C6 cycloalkyl, C4-C8 cycloalkylalkyl, hydroxyl C1-C6 alkyl, C1-C6 haloalkyl, C1-C6 alkylamino C1-C6 alkyl, C1-C6 alkoxy C1-C6 alkyl, and C3-C6 heterocyclyl C1-C6 alkyl; and $R_6$ is selected from halogen, C1-C6 alkyl, C1-C6 alkoxy, and C1-C6 haloalkyl.

2. The primary cell culture medium of claim 1, wherein, $R_1$ is selected from C1-C6 alkyl, C3-C6 cycloalkyl, C4-C8 cycloalkylalkyl, C2-C6 spirocycloalkyl, and phenyl optionally independently substituted with 1-2 $R_6$, naphthyl optionally independently substituted with 1-2 $R_6$, phenylmethyl optionally independently substituted with 1-2 $R_6$ and thienyl optionally independently substituted with 1-2 $R_6$;

$R_2$ and $R_3$ are each independently selected from C1-C3 alkyl;

$R_4$ and $R_5$ are each independently selected from hydrogen, C1-C6 alkyl, C3-C6 cycloalkyl, C4-C8 cycloalkylalkyl, hydroxyl C1-C6 alkyl, C1-C6 haloalkyl, C1-C6 alkylamino C1-C6 alkyl, C1-C6 alkoxy C1-C6 alkyl, piperidyl C1-C6 alkyl, and tetrahydropyranyl C1-C6 alkyl; and $R_6$ is selected from halogen, C1-C6 alkyl, C1-C6 alkoxy, and C1-C6 haloalkyl.

3. The primary cell culture medium of claim 1, wherein the MST1/2 kinase inhibitor comprises a compound of Formula (Ia) or a pharmaceutically acceptable salt, or a solvate thereof, Formula (Ia)

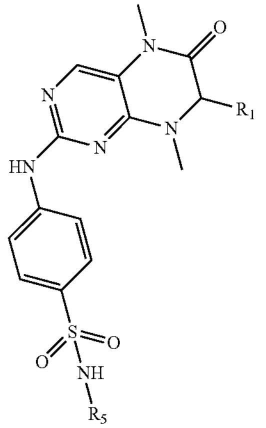

wherein, $R_1$ is selected from C1-C6 alkyl, phenyl optionally independently substituted with 1-2 $R_6$, thienyl optionally independently substituted with 1-2 $R_6$, and phenylmethyl optionally independently substituted with 1-2 $R_6$;

$R_5$ is selected from hydrogen, C1-C6 alkyl, and C3-C6 cycloalkyl; and $R_6$ is independently selected from halogen, C1-C6 alkyl, and C1-C6 haloalkyl.

4. The primary cell culture medium of claim 3, wherein $R_1$ is phenyl optionally independently substituted with 1-2 $R_6$;

$R_5$ is hydrogen; and
$R_6$ is fluoro, methyl or trifluoromethyl.
5. The primary cell culture medium of claim 1, wherein the MST1/2 kinase inhibitor is at least one selected from the following compounds or a pharmaceutically acceptable salt thereof:
1
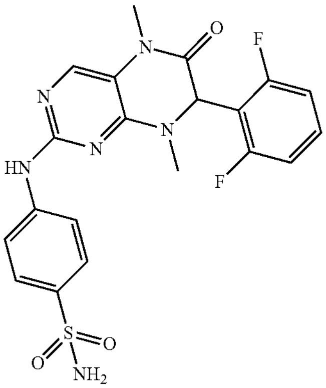
2
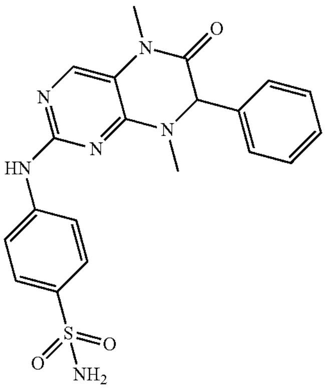
3
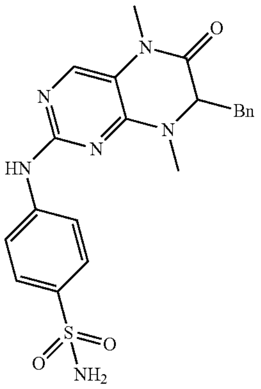
-continued
4
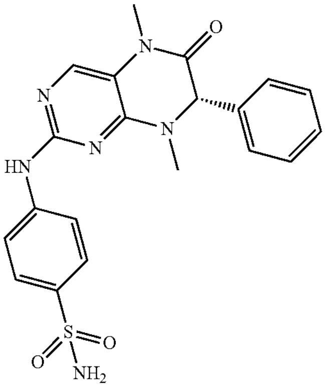
5
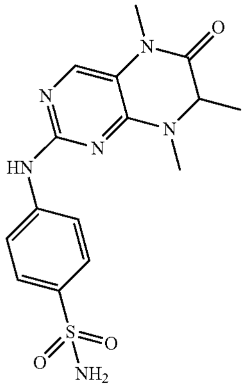
6
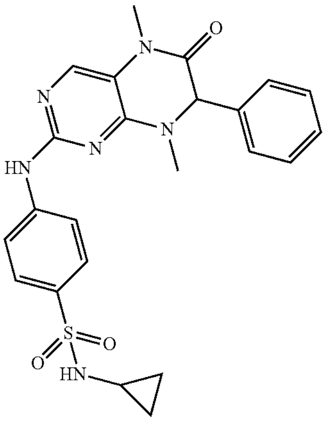
7
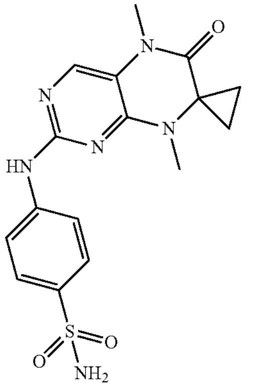

8
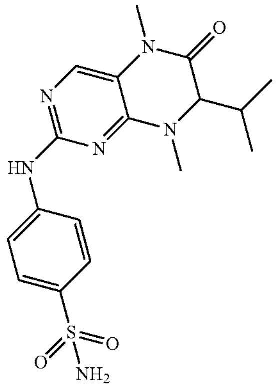
9
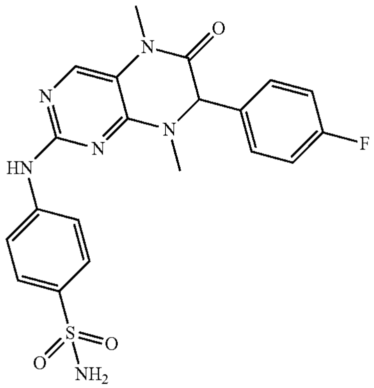
10
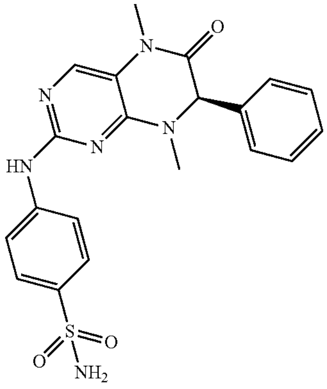
11
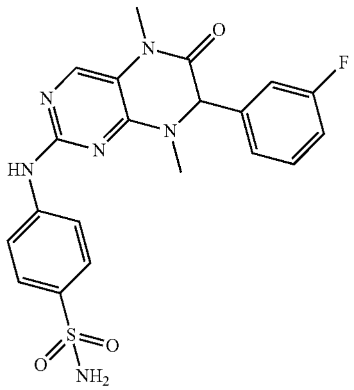
12
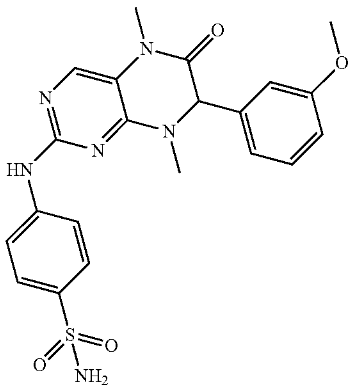
13
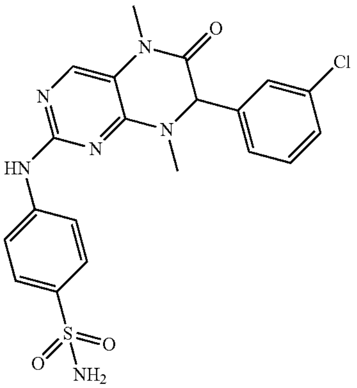
14
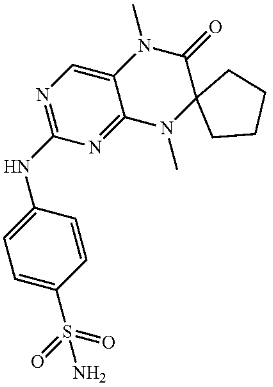
15
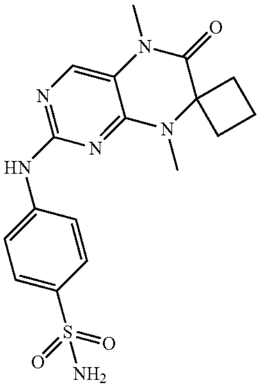

-continued
16
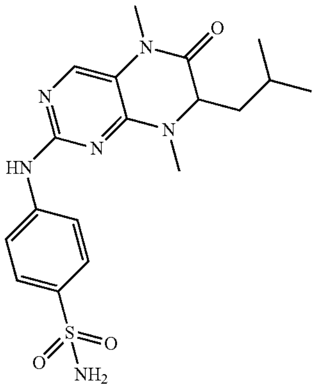
17
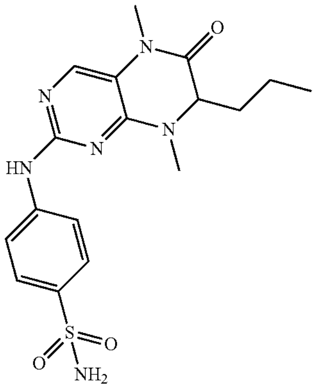
18
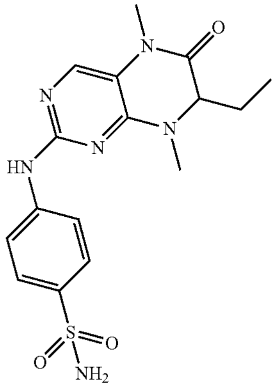
19
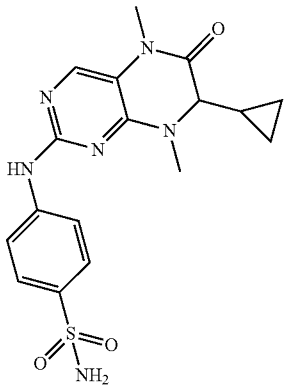
-continued
20
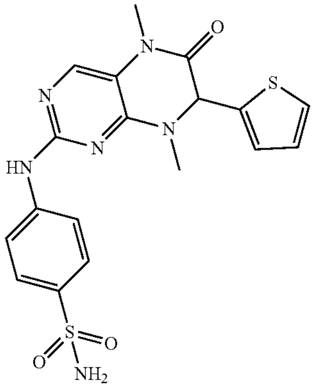
21
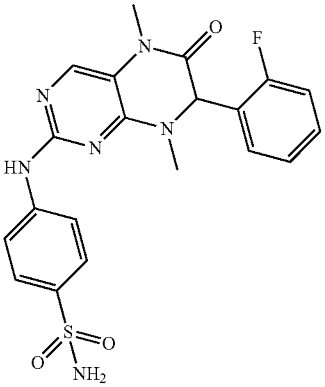
22
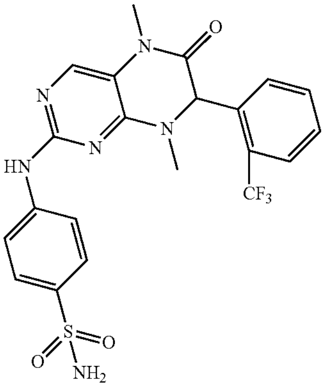
23
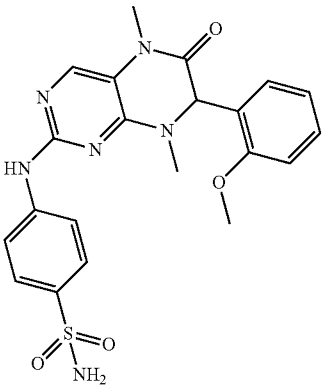

-continued
24
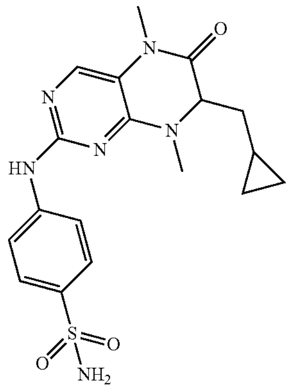
25
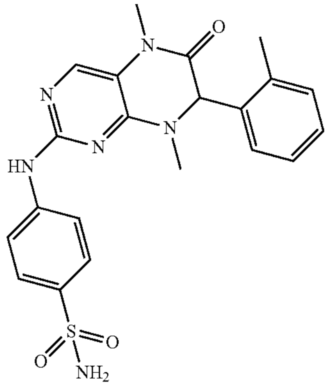
26
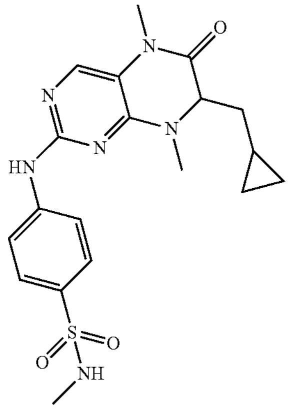
27
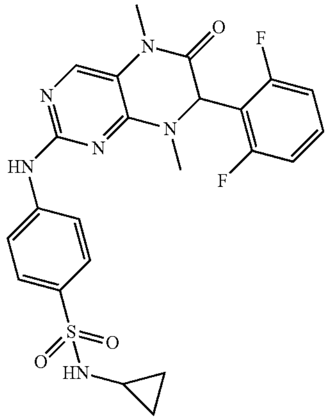
-continued
28
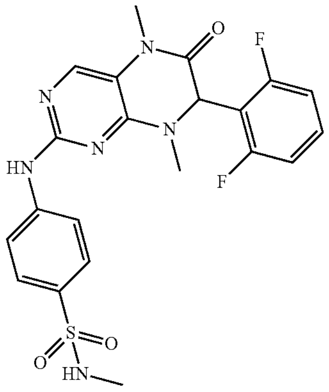
29
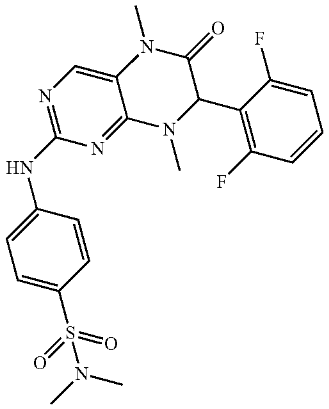
30
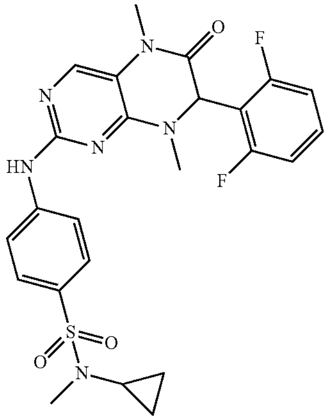
31
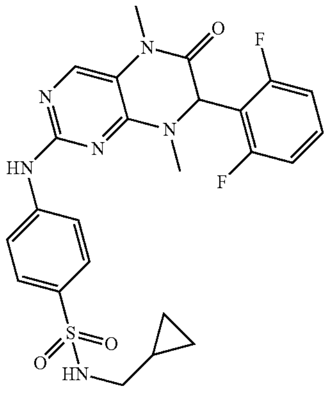

32
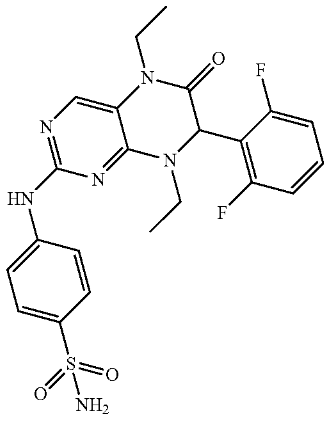
33
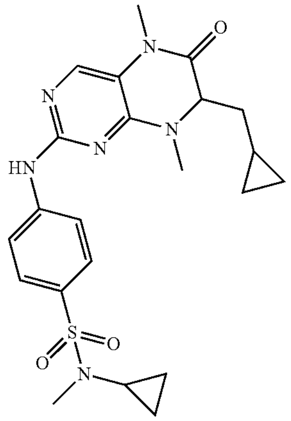
34
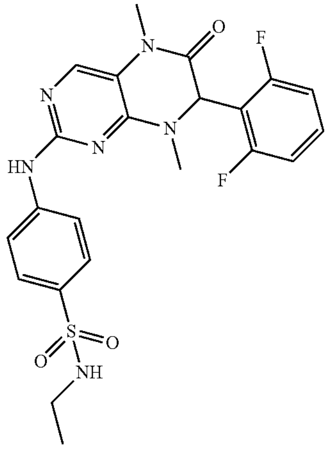
35
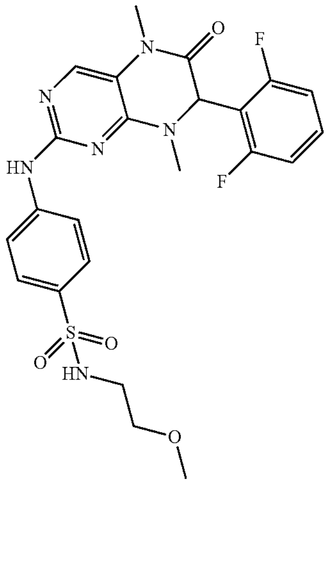
36
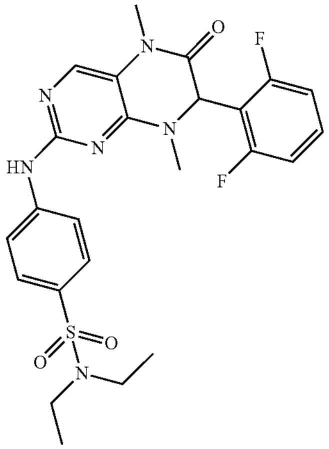
37
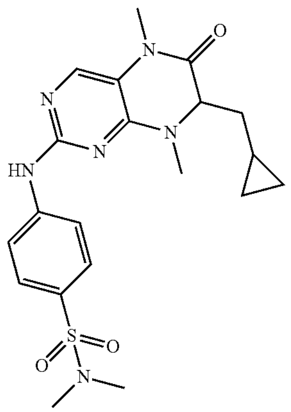

-continued
38
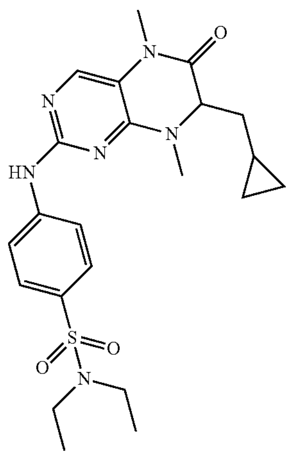
39
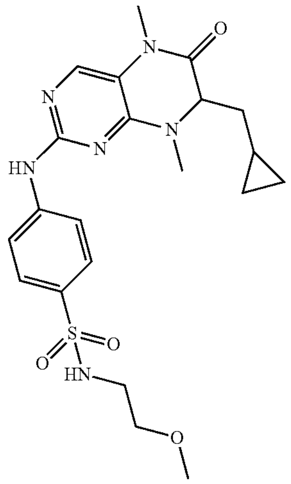
40
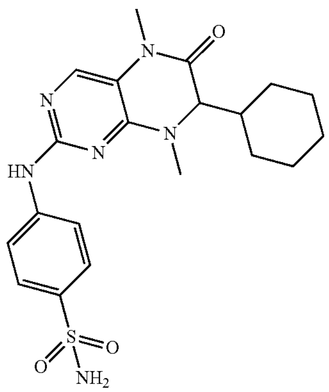
-continued
41
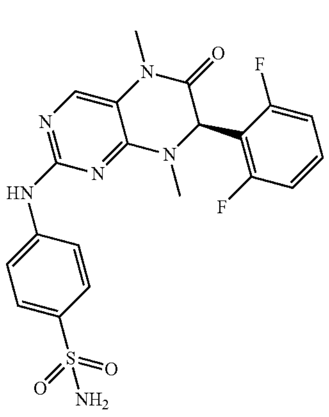
42
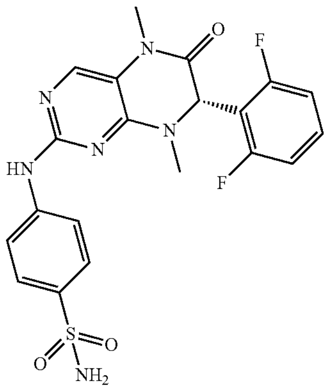
43
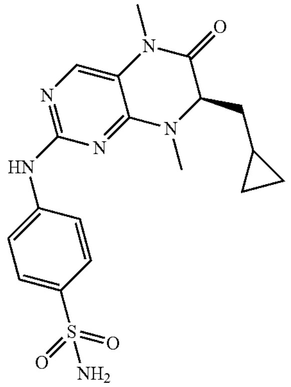
44
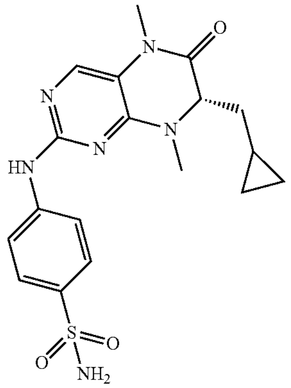

-continued
45
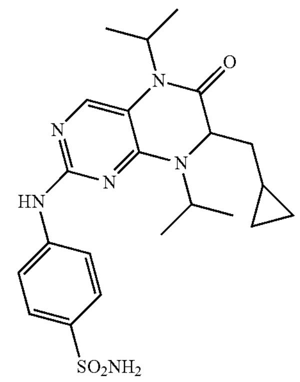
46
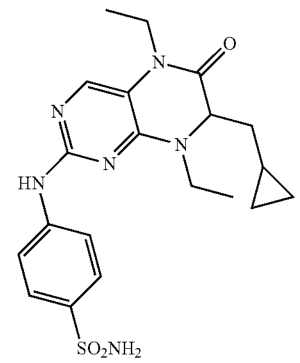
47
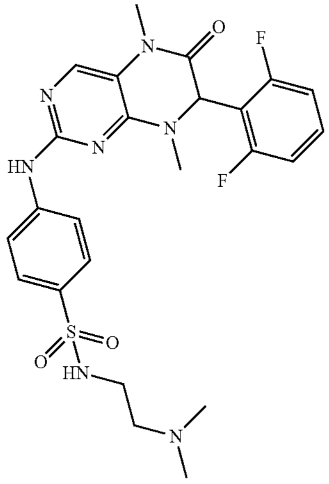
-continued
48
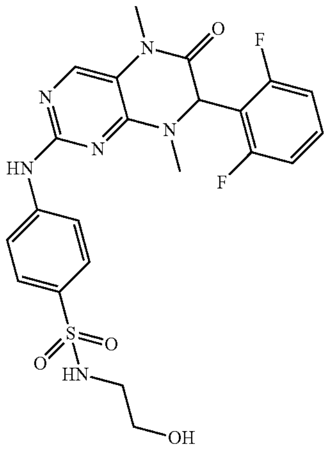
49
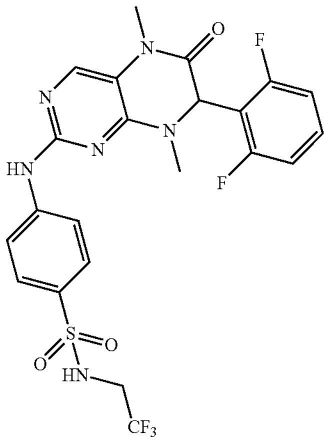
50
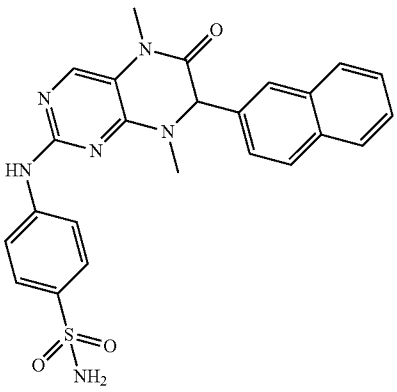

-continued
51
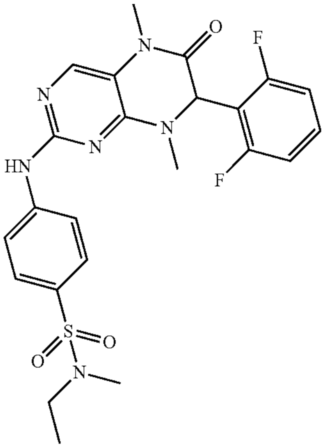
52
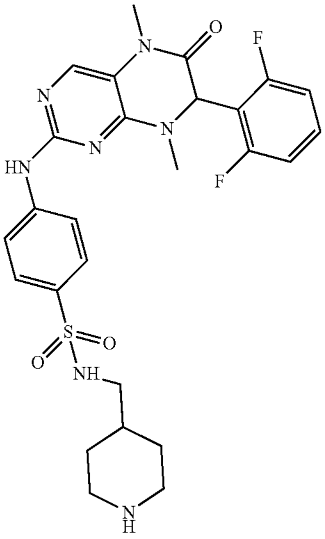
53
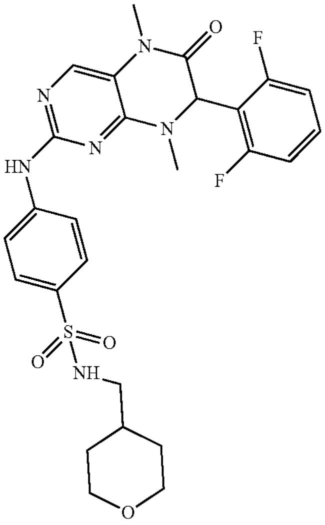
-continued
54
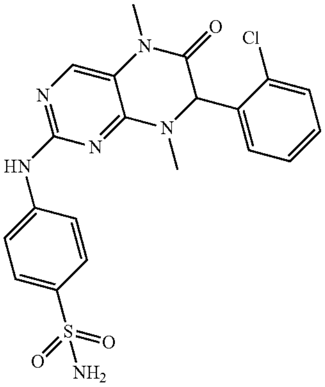
55
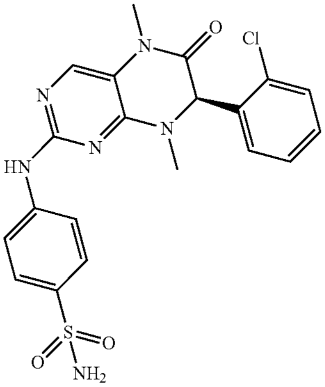
56
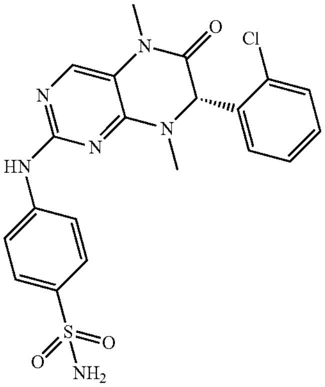
57
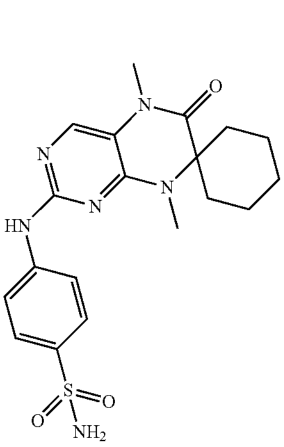

-continued

58

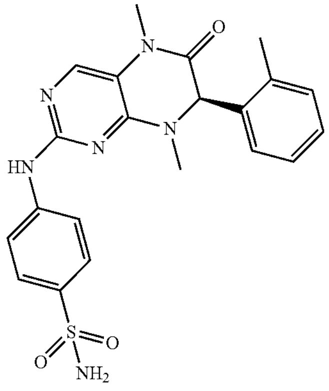

59

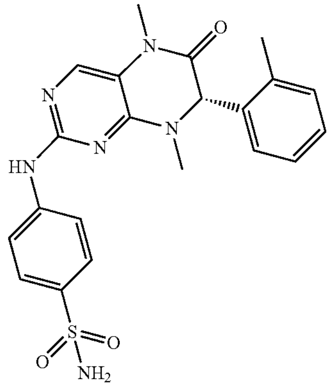

.

6. The primary cell culture medium of claim 1, wherein, the amount of the MST1/2 kinase inhibitor is 0.3 μM-10 μM.

7. The primary cell culture medium of claim 1, wherein, the amount of the ROCK inhibitor in the culture medium is 0.3 μM-20 μM.

8. The primary cell culture medium of claim 1, wherein, the amount of epidermal growth factor is 12.5 ng/ml-100 ng/ml;

the respective amounts of insulin/transferrin/sodium selenite in the insulin-transferrin-Selenium complex are 2.5-20 μg/ml, 1.25-10 μg/ml, and 1.25-10 ng/ml, respectively;

the amount of hepatocyte growth factor is 2.5 ng/ml-20 ng/ml;

the amount of the TGFβ type I receptor inhibitor is 125 nM-500 nM;

and the amount of the P38/MAPK inhibitor is 125 nM-500 nM.

9. The primary cell culture medium of claim 1, wherein the primary cell culture medium is free of serum, bovine pituitary extract, Wnt agonists, R-spondin family proteins, BMP inhibitors, nicotinamide, and N-acetylcysteine.

10. The primary cell culture medium of claim 1, wherein, the primary ESCC epithelial cells are selected from ESCC tumor cells, normal ESCC epithelial cells, and ESCC epithelial stem cells.

11. The primary cell culture medium of claim 1, wherein, the amount of the MST1/2 kinase inhibitor is 0.75 μM-6 μM;

the amount of the ROCK inhibitor in the culture medium is 2.5 μM-15 μM;

the amount of epidermal growth factor is 50 ng/ml-100 ng/ml;

the respective amounts of insulin/transferrin/sodium selenite in the insulin-transferrin-selenium complex are 5-20 μg/ml, 2.5-10 μg/ml, 2.5-10 ng/ml, respectively;

the amount of hepatocyte growth factor is 10 ng/ml-20 ng/ml;

the amount of the TGFβ type I receptor inhibitor is 250 nM-500 nM; and the amount of the P38/MAPK inhibitor is 250 nM-500 nM.

12. The primary cell culture medium of claim 11, wherein, the amount of the MST1/2 kinase inhibitor is 2 μM-6 μM; and the amount of the ROCK inhibitor in the culture medium is 7.5 μM-12.5 μM.

13. A method for culturing primary ESCC epithelial cells, characterized in comprising the following steps:

(1) preparing the primary cell culture medium according to claim 1;

(2) coating a culture vessel with extracellular matrix gel diluent;

(3) inoculating primary ESCC epithelial cells isolated from ESCC tissues in the coated culture vessel, and culturing with the primary cell culture medium of step (1).

* * * * *